US011295841B2

(12) United States Patent
Barber et al.

(10) Patent No.: US 11,295,841 B2
(45) Date of Patent: Apr. 5, 2022

(54) UNSUPERVISED LEARNING AND PREDICTION OF LINES OF THERAPY FROM HIGH-DIMENSIONAL LONGITUDINAL MEDICATIONS DATA

(71) Applicant: Tempus Labs, Inc., Chicago, IL (US)

(72) Inventors: Mathew Barber, Chicago, IL (US); Ryan Mork, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 0 days.

(21) Appl. No.: 17/001,673

(22) Filed: Aug. 24, 2020

(65) Prior Publication Data

US 2021/0057071 A1 Feb. 25, 2021

Related U.S. Application Data

(60) Provisional application No. 62/890,178, filed on Aug. 22, 2019.

(51) Int. Cl.
*G16H 20/10* (2018.01)
*G16H 10/60* (2018.01)
(Continued)

(52) U.S. Cl.
CPC ......... *G16H 20/10* (2018.01); *G06K 9/00456* (2013.01); *G06N 20/00* (2019.01);
(Continued)

(58) Field of Classification Search
CPC ........ G16H 20/10; G16H 10/60; G16H 50/30; G06N 20/00; G06K 9/00456; G06K 2209/01
See application file for complete search history.

(56) References Cited

U.S. PATENT DOCUMENTS 6,804,656 B1 10/2004 Rosenfeld
9,031,926 B2 5/2015 Milward
(Continued)

FOREIGN PATENT DOCUMENTS

WO 2020023420 A2 1/2020

OTHER PUBLICATIONS

Institute of Medicine of the National Academies. Clinical Trials in Cancer. Chapter 6 in Transforming Clinical Research in the United States: Challenges and Opportunities: Workshop Summary (ed. Institute of Medicine (US) Forum on Drug Discovery, Development, and T.) (National Academies Press, 2010).
(Continued)

*Primary Examiner* — John P Go
*Assistant Examiner* — Chad A Newton
(74) *Attorney, Agent, or Firm* — Quarles & Brady LLP

(57) ABSTRACT

In one aspect, the present disclosure provides a method for labeling one or more medications concurrently administered to a patient as a line of therapy. The method includes identifying medical records of the patient from a plurality of digital records, creating, from the subset of medical records, a plurality of treatment intervals including at least one medication administered to the patient and a time interval, associating medications of the one or more treatments with a respective treatment interval when the administration of the medication falls within the time interval, refining the time interval of a respective treatment interval when a treatment of the one or more treatments falls outside the time interval but within an extension period, identifying one or more potential lines of therapy from the plurality of treatment intervals, and labeling the potential line of therapy having the highest maximum likelihood estimation as the line of therapy.

30 Claims, 37 Drawing Sheets

(51) Int. Cl.
*G06N 20/00* (2019.01)
*G06K 9/00* (2022.01)
*G16H 50/30* (2018.01)

(52) U.S. Cl.
CPC ............. *G16H 10/60* (2018.01); *G16H 50/30* (2018.01); *G06K 2209/01* (2013.01)

(56) References Cited

U.S. PATENT DOCUMENTS

| | | | |
|---|---|---|---|
| 9,208,217 | B2 | 12/2015 | Milward |
| 9,424,532 | B1 | 8/2016 | Abedini |
| 2002/0173702 | A1 | 11/2002 | Lebel |
| 2004/0122790 | A1 | 6/2004 | Walker |
| 2007/0005621 | A1 | 1/2007 | Lesh |
| 2008/0162393 | A1 | 7/2008 | Illiff |
| 2008/0195600 | A1 | 8/2008 | Deakter |
| 2009/0319244 | A1 | 12/2009 | West |
| 2010/0029498 | A1 | 2/2010 | Gnirke |
| 2011/0255790 | A1* | 10/2011 | Duggan ............. G06K 9/00442 382/190 |
| 2011/0288877 | A1 | 11/2011 | Ofek |
| 2012/0110016 | A1 | 5/2012 | Phillips |
| 2012/0123184 | A1* | 5/2012 | Otto ..................... A61N 5/1067 600/1 |
| 2012/0265544 | A1 | 10/2012 | Hwang |
| 2013/0096947 | A1 | 4/2013 | Shah |
| 2013/0246049 | A1 | 9/2013 | Mirhaji |
| 2014/0122117 | A1 | 5/2014 | Masarie |
| 2014/0244625 | A1 | 8/2014 | Seghezzi |
| 2014/0249761 | A1 | 9/2014 | Carroll |
| 2014/0278461 | A1 | 9/2014 | Artz |
| 2014/0280353 | A1 | 9/2014 | Delany |
| 2014/0365242 | A1 | 12/2014 | Neff |
| 2015/0006558 | A1 | 1/2015 | Leighton |
| 2015/0106125 | A1 | 4/2015 | Farooq |
| 2015/0178386 | A1 | 6/2015 | Oberkampf |
| 2015/0213194 | A1 | 7/2015 | Wolf |
| 2015/0324527 | A1 | 11/2015 | Siegel |
| 2015/0331909 | A1 | 11/2015 | Sundquist |
| 2016/0019666 | A1 | 1/2016 | Amarasingham |
| 2017/0046425 | A1 | 2/2017 | Tonkin |
| 2017/0109502 | A1 | 4/2017 | Labkoff |
| 2017/0177597 | A1 | 6/2017 | Asimenos |
| 2017/0177822 | A1 | 6/2017 | Fogel |
| 2017/0199965 | A1 | 7/2017 | Dekel |
| 2017/0237805 | A1 | 8/2017 | Worley |
| 2018/0046764 | A1 | 2/2018 | Katwala |
| 2018/0060523 | A1 | 3/2018 | Farh |
| 2018/0068083 | A1* | 3/2018 | Cohen ................... G16H 10/60 |
| 2018/0085015 | A1* | 3/2018 | Crowder ............. A61B 5/0484 |
| 2018/0121618 | A1 | 5/2018 | Smith |
| 2018/0144003 | A1 | 5/2018 | Formoso |
| 2018/0311224 | A1* | 11/2018 | Hedley ................. A61K 31/454 |
| 2018/0373844 | A1 | 12/2018 | Ferrandez-Escamez |
| 2019/0050530 | A1 | 2/2019 | De La Vega |
| 2019/0057774 | A1 | 2/2019 | Velez |
| 2019/0108912 | A1 | 4/2019 | Spurlock, III |
| 2019/0206524 | A1 | 7/2019 | Baldwin |
| 2020/0005461 | A1 | 1/2020 | Yip |
| 2020/0118644 | A1 | 4/2020 | Khan |
| 2020/0176098 | A1* | 6/2020 | Lucas ..................... G16H 10/20 |
| 2020/0219619 | A1 | 7/2020 | Feczko |

OTHER PUBLICATIONS

International Searching Authority, International Search Report and Written Opinion for application PCT/US2019/056713, dated Feb. 27, 2020.
International Searching Authority, International Search Report and Written Opinion for application PCT/US2019/064329, dated Apr. 1, 2020.
Kavasidis, I. et al. "A Saliency-based Convolutional Neural Network for Table and Chart Detection in Digitized Documents," Submitted to IEEE Transactions on Multimedia, Apr. 17, 2018, pp. 1-13.
Kim, Youngjun et al. "A Study of Concept Extraction Across Different Types of Clinical Notes," AMIA Annu Symp Proc. 2015; Nov. 5, 2015, pp. 737-746.
Lafferty, John et al. "Conditional Random Fields: Probabilistic Models for Segmenting and Labeling Sequence Data," Proceedings of the 18th International Conference on Machine Learning 2001 (ICML 2001), Jun. 28, 2001, pp. 282-289.
Lample, Guillaume et al. "Neural Architectures for Named Entity Recognition," Association for Computational Linguistics, Proceedings of NAACL-HLT 2016, San Diego, California, Jun. 12-17, 2016, pp. 260-270.
Lang, Francois-Michel et al. "Increasing UMLS Coverage and Reducing Ambiguity via Automated Creation of Synonymous Terms: First Steps toward Filling UMLS Synonymy Gaps," Semantic Scholar, 2017, pp. 1-26.
Laserson, Jonathan et al. "TextRay: Mining Clinical Reports to Gain a Broad Understanding of Chest X-rays," arXiv:1806.02121 [cs.CV], Jun. 6, 2018, 13 pages.
Lau, D., et al. RNA Sequencing of the Tumor Microenvironment in Precision Cancer Immunotherapy. Trends in Cancer 5, 149-156 (2019).
Lawrence, M. S. et al. Mutational heterogeneity in cancer and the search for new cancer-associated genes. Nature 499, 214-218 (2013).
Layer, R. M., et al. LUMPY: a probabilistic framework for structural variant discovery. Genome Biol. 15, R84 (2014).
Le, D. T. et al. Mismatch repair deficiency predicts response of solid tumors to PD-1 blockade. Science 357, 409-413 (2017).
Lee, Kenton et al. "End-to-end Neural Coreference Resolution," arXiv:1707.07045 [cs.CL], Dec. 15, 2017, 10 pages.
Lei, Tao et al. "Rationalizing Neural Predictions," arXiv:1606.04155 [cs.CL], Nov. 2, 2016, 11 pages.
Lek, M. et al. Analysis of protein-coding genetic variation in 60,706 humans. Nature 536, 285-291 (2016).
Li, H. et al. Fast and accurate short read alignment with Burrows-Wheeler transform. Bioinformatics 25, 1754-1760 (2009).
Li, M. M. et al. Standards and Guidelines for the Interpretation and Reporting of Sequence Variants in Cancer. J. Mol. Diagnostics 19, 4-23 (2017).
Liao, Y., et al. featureCounts: an efficient general purpose program for assigning sequence reads to genomic features. Bioinformatics 30, 923-930 (2014).
Ling, Yuan et al. "Learning to Diagnose: Assimilating Clinical Narratives using Deep Reinforcement Learning," Proceedings of the the 8th International Joint Conference on Natural Language Processing, Taipei, Taiwan, Nov. 27-Dec. 1, 2017, pp. 895-905.
Lipton, Zachary et al. "Learning to Diagnose With LSTM Recurrent Neural Networks," ICLR 2016, arXiv:1511.03677 [cs.LG], pp. 1-18.
Lonsdale, J. et al. The Genotype-Tissue Expression (GTEx) project. Nat. Genet. 45, 580-585 (2013).
Luraghi, P. et al. A Molecularly Annotated Model of Patient-Derived Colon Cancer Stem-Like Cells to Assess Genetic and Nongenetic Mechanisms of Resistance to Anti-EGFR Therapy. Clin. Cancer Res. 24, 807-820 (2018).
Ma, Xuezhe et al. "End-to-end Sequence Labeling via Bi-directional LSTM-CNNs-CRF," arXiv:1603.01354v5 [cs.LG], May 29, 2016, 12 pages.
MacKenzie, Andrei (andrei-m/levenshtein.js) "Levenshtein distance between two given strings implemented in JavaScript and usable as a Node.js module," GitHub, Inc., latest comment dated on Feb. 2, 2018, 9 pages. Retrieved from Internet. URL: https://gist.github.com/andrei-m/982927.
Madhavan, S. et al. ClinGen Cancer Somatic Working Group—standardizing and democratizing access to cancer molecular diagnostic data to drive translational research. Pac. Symp. Biocomput. 23, 247-258 (2018).
Maxwell, K. N. et al. BRCA locus-specific loss of heterozygosity in germline BRCA1 and BRCA2 carriers. Nat. Commun. 8, 319 (2017).

(56) References Cited

OTHER PUBLICATIONS

Mendell, J. et al. Clinical Translation and Validation of a Predictive Biomarker for Patritumab, an Anti-human Epidermal Growth Factor Receptor 3 (HER3) Monoclonal Antibody, in Patients With Advanced Non-small Cell Lung Cancer. EBioMedicine 2, 264-271 (2015).
Mihalcea, Rada et al. "Part IV Graph-Based Natural Language Processing" excerpted from a book "Graph-Based Natural Language Processing and Information Retrieval," Cambridge University Press, First published 2011 (Reprinted 2012), 63 pages.
Miller, A. et al. High somatic mutation and neoantigen burden are correlated with decreased progression-free survival in multiple myeloma. Blood Cancer J. 7, e612 (2017).
Mysore, Sheshera S. "Segmentation of Non-text Objects with Connected Operators" Msheshera, May 21, 2017, 2 pages. Retrieved from Internet. URL: http://msheshera.github.io/non-text-segment-connected-operators.html.
Narasimhan, Karthik et al. "Improving Information Extraction by Acquiring External Evidence with Reinforcement Learning," arXiv:1603.07954v3 [cs.CL], Sep. 27, 2016, 12 pages.
Neelakantan, Arvind et al. "Learning Dictionaries for Named Entity Recognition using Minimal Supervision," Proceedings of the 14th Conference of the European Chapter of the Association for Computational Linguistics, Gothenburg, Sweden, Apr. 26-30, 2014, pp. 452-461.
Newman, A. M. et al. Robust enumeration of cell subsets from tissue expression profiles. Nat. Methods 12, 453-7 (2015).
Newton, Y. et al. TumorMap: Exploring the Molecular Similarities of Cancer Samples in an Interactive Portal. Cancer Res. 77, e111-e114 (2017).
Peng, L. et al. Large-scale RNA-Seq Transcriptome Analysis of 4043 Cancers and 548 Normal Tissue Controls across 12 TCGA Cancer Types. Sci. Rep. 5, 13413 (2015).
Peters, Matthew. E. et al. "Semi-supervised sequence tagging with bidirectional language models," arXiv:1705.00108v1 [cs.CL], Apr. 29, 2017, 10 pages.
Prakash, Aaditya et al. "Condensed Memory Networks for Clinical Diagnostic Inferencing," arXiv:1612.01848v2 [cs.CL], Jan. 3, 2017, 8 pages.
Radovich, M. et al. Clinical benefit of a precision medicine based approach for guiding treatment of refractory cancers. Oncotarget 7, 56491-56500 (2016).
Reiman, D. et al. Integrating RNA expression and visual features for immune infiltrate prediction. Biocomputing 2019, 284-295 (2018).
Richards, S. et al. Standards and guidelines for the interpretation of sequence variants: a joint consensus recommendation of the American College of Medical Genetics and Genomics and the Association for Molecular Pathology. Genet. Med. 17, 405-24 (2015).
Robinson, D. R. et al. Integrative clinical genomics of metastatic cancer. Nature 548, 297-303 (2017).
Rooney, M. S. et al. Molecular and Genetic Properties of Tumors Associated with Local Immune Cytolytic Activity. Cell 160, 48-61 (2015).
Rosenthal, R., et al. deconstructSigs: delineating mutational processes in single tumors distinguishes DNA repair deficiencies and patterns of carcinoma evolution. Genome Biol. 17, (2016).
Roufas, C. et al. The Expression and Prognostic Impact of Immune Cytolytic Activity-Related Markers in Human Malignancies: A Comprehensive Meta-analysis. Front. Oncol. 8, 27 (2018).
Sager, Naomi et al. "Natural Language Processing and the Representation of Clinical Data," Journal of the American Medical Informatics Association, vol. 1, No. 2, Mar./Apr. 1994, pp. 142-160.
Sambyal, Nitigya et al. "Automatic Text Extraction and Character Segmentation Using Maximally Stable Extremal Regions," arXiv:1608.03374 [cs.CV], Aug. 11, 2016, 6 pages.
Savova, et al., "Mayo clinical Text Analysis and Knowledge Extraction System (cTAKES): architecture, component evaluation and applications", J Am Med Inform Assoc 2010;17: 507-513., retrieved from the internet at: https://academic.oup.com/jamia/article/17/5/507/830823, on Dec. 3, 2019, 7 pages.

Sheng, Q. et al. An Activated ErbB3/NRG1 Autocrine Loop Supports In Vivo Proliferation in Ovarian Cancer Cells. Cancer Cell 17, 298-310 (2010).
Solomon, B., et al. ALK Gene Rearrangements: A New Therapeutic Target in a Molecularly Defined Subset of Non-small Cell Lung Cancer. J. Thorac. Oncol. 4, 1450-1454 (2009).
"Algorithm Implementation/Strings/Levenshtein distance," Wikibooks, last edited on Jan. 5, 2019, 39 pages. Retrieved from Internet. URL: https://en.wikibooks.org/wiki/Algorithm_Implementation/Strings/Levenshtein_distance#Python.
"Amazon Textract—Easily extract text and data from virtually any document," Amazon, Nov. 28, 2018, 6 pages. Retrieved from Internet. URL: https://aws.amazon.com/textract/.
"CliNER," Text Machine Lab 2014, Nov. 10, 2017, 2 pages. Retrieved from Internet. URL: http://text-machine.cs.uml.edu/cliner/.
"Clinithink CLiX CNLP (Harness unstructured data to drive value across the healthcare continuum)," Clinithink Limited, 2015, 1 page. Retrieved from Internet. URL: http://clinithink.com/wp-content/uploads//2015/01/Clinithink-CLiX-CNLP-Sell-Sheet-US.pdf.
"Evernote Scannable on the App Store," Jun. 18, 2018, 3 pages. Retrieved from Internet. URL: https://itunes apple.com/us/app/evernote-scannable/id883338188?mt=8.
"I2E: The world's leading Text Mining platform," 2019 Linguamatics, Aug. 14, 2018, 5 pages. Retrieved from Internet. URL: https://www.linguamatics.com/products-services/about-i2e.
"PHP: levenshtein—Manual," latest comment dated in 2014, 32 pages. Retrieved from Internet. URL: http://www.php.net/levenshtein.
"Talk:Algorithm Implementation/Strings/Levenshtein distance," Wikibooks, last edited on Nov. 2, 2016, 2 pages. Retrieved from Internet. URL: https://en.wikibooks.org/wiki/Talk:Algorithm_Implementation/Strings/Levenshtein_distance#Bug_in_vectorized_(5th)_version.
"Why cTAKES? See the animation below for a sampling of cTAKES capabilities," The Apache Software Foundation, Apr. 25, 2017, 1 page. Retrieved from Internet: URL: http://ctakes.apache.org/whycTAKES.html.
AACR Project GENIE Consortium. AACR Project GENIE: Powering Precision Medicine through an International Consortium. Cancer Discov. 7, 818-831 (2017).
Alexandrov, L. B. et al. Signatures of mutational processes in human cancer. Nature 500, 415-421 (2013).
Allen, J. et al. Barriers to Patient Enrollment in Therapeutic Clinical Trials for Cancer: A Landscape Report. (2018).
Aronson, Alan "MetaMap—A Tool for Recognizing UMLS Concepts in Text," Jan. 11, 2019, 2 pages. Retrieved from Internet. URL: https://metamap.nlm.nih.gov/.
Ayers, M. et al. IFN-?-related mRNA profile predicts clinical response to PD-1 blockade. J. Clin. Invest. 127, 2930-2940 (2017).
Balatero, David (dbalatero/levenshtein-ffi) "Fast string edit distance computation, using the Damerau-Levenshtein algorithm," GitHub, Inc., latest comment dated on Aug. 10, 2014, 2 pages. Retrieved from Internet. URL: https://github.com/dbalatero/levenshtein-ffi.
Beaubier, N. et al. Clinical Validation of the Tempus xT Next-Generation Sequencing Targeted Oncology Assay. Oncotarget 10, 2384-2396 (2019).
Caris Life Sciences. CODE: Comprehensive Oncology Data Explorer. Slideshow May 2017. Accessed on Dec. 16, 2020 at https://www.karmanos.org/Uploads/Public/Documents/Karmanos/CODE%20slides_5.2017.pptx%20.
Chae, Y. K. et al. Association of tumor mutational burden with DNA repair mutations and response to anti-PD-1/PD-L1 therapy in non-small cell lung cancer. Clin. Lung Cancer (2018). doi:10.1016/J.CLLC.2018.09.008.
Chatterjee, P. et al. The TMPRSS2-ERG Gene Fusion Blocks XRCC4-Mediated Nonhomologous End-Joining Repair and Radiosensitizes Prostate Cancer Cells to PARP Inhibition. Mol. Cancer Ther. 14, 1896-1906 (2015).
Chen, Huizhong et al. "Robust Text Detection in Natural Images With Edge-Enhanced Maximally Stable Extremal Regions," 2011 18th IEEE International Conference on Image Processing, Sep. 11-14, 2011, 4 pages.

(56) References Cited

OTHER PUBLICATIONS

Choi, Edward et al. "Coarse-to-Fine Question Answering for Long Documents," Proceedings of the 55th Annual Meeting of the Association for Computational Linguistics, Vancouver, Canada, Jul. 30-Aug. 4, 2017, pp. 209-220.

Choi, Edward et al. "Doctor AI: Predicting Clinical Events via Recurrent Neural Networks," Proceedings of Machine Learning for Healthcare 2016, JMLR W&C Track vol. 56, 2016, pp. 1-18.

Collobert, Ronan et al. "Natural Language Processing (Almost) from Scratch," Journal of Machine Learning Research 12, (2011) pp. 2493-2537.

Conneau, Alexis et al. "Very Deep Convolutional Networks for Text Classification," arXiv:1606.01781 [cs.CL], Jan. 27, 2017, 10 pages.

Conway, J. R., et al. UpSetR: an R package for the visualization of intersecting sets and their properties. Bioinformatics 33, 2938-2940 (2017).

Cristescu, R. et al. Pan-tumor genomic biomarkers for PD-1 checkpoint blockade-based immunotherapy. Science 362, eaar3593 (2018).

Darvin, P., et al. Immune checkpoint inhibitors: recent progress and potential biomarkers. Exp. Mol. Med. 50, 165 (2018).

Das, Rajarshi et al. "Chains of Reasoning over Entities, Relations, and Text using Recurrent Neural Networks," Proceedings of the 15th Conference of the European Chapter of the Association for Computational Linguistics: vol. 1, Valencia, Spain, Apr. 3-7, 2017, pp. 132-141.

De Bruijn, Berry et al. "Machine-learned solutions for three stages of clinical information extraction: the state of the art at i2b2 2010," 18 J. Am. Med. Inform. Assoc. 2011, May 12, 2011, pp. 557-562.

Desrichard, A., et al. Cancer Neoantigens and Applications for Immunotherapy. (2016). doi:10.1158/1078-0432. CCR-14-3175.

Dhir, M. et al. Impact of genomic profiling on the treatment and outcomes of patients with advanced gastrointestinal malignancies. Cancer Med. 6, 195-206 (2017).

Dienstmann, R. et al. Standardized decision support in next generation sequencing reports of somatic cancer variants. Mol. Oncol. 8, 859-873 (2014).

Dienstmann, R., et al. "Database of genomic biomarkers for cancer drugs and clinical targetability in solid tumors." Cancer discovery 5.2 (2015): 118-123.

DNANEXUS. Working with UK Biobank: A Research Guide. Accessed online on Dec. 31, 2020. Available at https://web.archive.org/save/https://dna-nexus-prod-s3-assets-5 1tcpaqcp0pd.s3.amazonaws.com/images/files/DNAnexus_WhitePaper_Working-with-UKB-Data_2.pdf.

Dobin, A. et al. STAR: ultrafast universal RNA-seq aligner. Bioinformatics 29, 15-21 (2013).

Dozat, Timothy et al. "Deep Biaffine Attention for Neural Dependency Parsing," Published as a conference paper at ICLR 2017, arXiv:1611.01734 [cs.CL], Mar. 10, 2017, pp. 1-8.

Faust, G. G. et al. SAMBLASTER: fast duplicate marking and structural variant read extraction. Bioinformatics 30, 2503-2505 (2014).

Fernandes, G. et al. Next-generation Sequencing-based genomic profiling: Fostering innovation in cancer care? Clinics 72, 588-594 (2017).

Finan, C. et al. The druggable genome and support for target identification and validation in drug development. Sci. Transl. Med. 9, eaag1166 (2017).

Forbes, S. A. et al. COSMIC: somatic cancer genetics at high-resolution. Nucleic Acids Res. 45, D777-D783 (2017).

Genthial, Guillaum "Sequence Tagging with Tensorflow (bi-LSTM + CRF with character embeddings for NER and POS)," Guillaume Genthial blog, Apr. 5, 2017, 23 pages.

Goldman, M. et al. The UCSC Xena platform for public and private cancer genomics data visualization and interpretation. bioRxiv 326470 (2019). doi:10.1101/326470.

Gong, J. et al. Value-based genomics. Oncotarget 9, 15792-15815 (2018).

Goodman, A. M. et al. Tumor Mutational Burden as an Independent Predictor of Response to Immunotherapy in Diverse Cancers. Mol. Cancer Ther. 16, 2598-2608 (2017).

Griffith, M. et al. CIViC is a community knowledgebase for expert crowdsourcing the clinical interpretation of variants in cancer. Nat. Genet. 49, 170-174 (2017).

Han, M.-E. et al. Overexpression of NRG1 promotes progression of gastric cancer by regulating the self-renewal of cancer stem cells. J. Gastroenterol. 50, 645-656 (2015).

Hartmaier, R. J. et al. High-Throughput Genomic Profiling of Adult Solid Tumors Reveals Novel Insights into Cancel Pathogenesis. Cancer Res. 77, 2464-2475 (2017).

He, Dafang et al. "Multi-scale Multi-task FCN for Semantic Page Segmentation and Table Detection," IEEE, 2017 14th IAPR International Conference on Document Analysis and Recognition, Nov. 9-15, 2017, pp. 254-261.

He, Luheng et al. "Deep Semantic Role Labeling: WhatWorks and What's Next" Proceedings of the 55th Annual Meeting of the Association for Computational Linguistics, Vancouver, Canada, Jul. 30-Aug. 4, 2017, pp. 473-483.

Hegde, G. V. et al. Blocking NRG1 and Other Ligand-Mediated Her4 Signaling Enhances the Magnitude and Duration of the Chemotherapeutic Response of Non-Small Cell Lung Cancer. Sci. Transl. Med. 5, 171ra18-171ra18 (2013).

Szolek, A. et al. OptiType: precision HLA typing from next-generation sequencing data. Bioinformatics 30, 3310-3316 (2014).

Teer, J. K. et al. Evaluating somatic tumor mutation detection without matched normal samples. Hum. Genomics 11, 22 (2017).

The ASCO Post. 2018 ASCO: Impact Trial Matches Treatment to Genetic Changes in the Tumor to Improve Survival Across Multiple Cancer Types—The ASCO Post. Jun. 6, 2018 (2018). Available at: http://www.ascopost.com/News/58897.

Tomlins, S. A. et al. Recurrent fusion of TMPRSS2 and ETS transcription factor genes in prostate cancer. Science 310, 644-648 (2005).

Tsou, Ching-Huei et al. "Watson for Patient Record Analytics (aka Watson EMRA)," IBM Research, Aug. 2017, 5 pages. Retrieved from Internet. URL: https://researcher.watson.ibm.com/researcher/view_group.php?id=7664.

Unger, J. M., et al. Systematic Review and Meta-Analysis of the Magnitude of Structural, Clinical, and Physician and Patient Barriers to Cancer Clinical Trial Participation. J. Natl. Inst. 111, 245-255 (2019).

Wang, Z. et al. Significance of the TMPRSS2:ERG gene fusion in prostate cancer. Mol. Med. Rep. 16, 5450-5458 (2017).

Wheler, J. J. et al. Cancer Therapy Directed by Comprehensive Genomic Profiling: A Single Center Study. Cancer Res. 76, 3690-3701 (2016).

Wilson, T. R., et al. Neuregulin-1-Mediated Autocrine Signaling Underlies Sensitivity to HER2 Kinase Inhibitors in a Subset of Human Cancers. Cancer Cell 20, 158-172 (2011).

Wu, Yonghui et al. "A Study of Neural Word Embeddings for Named Entity Recognition in Clinical Text," AMIA Annual Symp. Proc. 2015; Published online Nov. 5, 2015, pp. 1326-1333.

Yan, M. et al. HER2 expression status in diverse cancers: review of results from 37,992 patients. Cancer Metastasis Rev. 34, 157-64 (2015).

Yang, L. et al. NRG1-dependent activation of HER3 induces primary resistance to trastuzumab in HER2-overexpressing breast cancer cells. Int. J. Oncol. 51, 1553-1562 (2017).

Yonesaka, K. et al. Activation of ERBB2 Signaling Causes Resistance to the EGFR-Directed Therapeutic Antibody Cetuximab. Sci. Transl. Med. 3, 99ra86-99ra86 (2011).

Yong, W P, et al. "The role of pharmacogenetics in cancer therapeutics." British journal of clinical pharmacology 62.1 (2006): 35-46.

Yun, S. et al. Clinical significance of overexpression of NRG1 and its receptors, HER3 and HER4, in gastric cancer patients. Gastric Cancer 21, 225-236 (2018).

Zehir, A. et al. Mutational landscape of metastatic cancer revealed from prospective clinical sequencing of 10,000 patients. Nat. Med. 23, 703-713 (2017).

(56) References Cited

OTHER PUBLICATIONS

Zeng, et al., "Extracting principal diagnosis, co-morbidity and smoking status for asthma research: evaluation of a natural language processing system", BMC Medical Informatics and Decision Making 2006, 6:30, retrieved from the internet at: https://bmcmedinformdecismak.biomedcentral.com/articles/10.1186/1472-6947-6-30 on Dec. 3, 2019, 9 pages.

Zhang, Yuan et al. "Aspect-augmented Adversarial Networks for Domain Adaptation" sentiarXiv:1701.00188v2 [cs.CL], Sep. 25, 2017, 14 pages.

International Searching Authority. International Search Report and Written Opinion for application PCT/US2020/047704, dated Nov. 20, 2020.

International Searching Authority. International Search Report and Written Opinion for application PCT/US2021/017517, dated Apr. 29, 2021. 11 pages.

Bertsimas, D., et al. "Personalized diabetes management using electronic medical records." Diabetes care 40.2 (2017): 210-217.

Coutinho, A. D., et al. "Real-world treatment patterns and outcomes of patients with small cell lung cancer progressing after 2 lines of therapy." Lung Cancer 127 (2019): 53-58.

Dempster, A.P. et al. (1977). "Maximum Likelihood from Incomplete Data via the EM Algorithm". Journal of the Royal Statistical Society, Series B. 39 (1): 1-38.

Flaig, T. W., et al. "Treatment evolution for metastatic castration-resistant prostate cancer with recent introduction of novel agents: retrospective analysis of real-world data." Cancer Medicine 5.2 (2016): 182.

Gangul, R. Line of Therapy Analytics: A key to commercial drug success. Feb. 15, 2017. Available online https://www.saama.com/blog/line-therapy-analytics-key-commercial-drug-success/.

Malangone-Monaco, E., et al. "Prescribing patterns of oral antineoplastic therapies observed in the treatment of patients with advanced prostate cancer between 2012 and 2014: results of an oncology EMR analysis." Clinical therapeutics 38.8 (2016): 1817-1824.

Optum. Determining Lines of Therapy (LOT) in Oncology in Claims Databases. 2017. Available online at https://cdn-aem.optum.com/content/dam/optum3/optum/en/resources/white-papers/wf520768_guidelines-for-determining-lines-of-therapy.pdf.

Rajkumar, S. V., et al. "Guidelines for determination of the number of prior lines of therapy in multiple myeloma." Blood, The Journal of the American Society of Hematology 126.7 (2015): 921-922.

Tsang, J-P. Deploying Machine Learning for Commercial Analytics. PMSA.net. Version accessed Dec. 15, 2018. Available online at https://web.archive.org/web/20181215152550/http://www.pmsa.net/jpmsa-vol06-article09.

Rokach L., Maimon O., Decision Trees, 2005, Data Mining and Knowledge Discovery Handbook, pp. 165-192 (Year: 2005).

\* cited by examiner

300

500

UNSUPERVISED LEARNING AND PREDICTION OF LINES OF THERAPY FROM HIGH-DIMENSIONAL LONGITUDINAL MEDICATIONS DATA

CROSS REFERENCE TO RELATED APPLICATIONS

This application claims the benefit of priority to U.S. provisional patent application No. 62/890,178, filed Aug. 22, 2019, and titled "Unsupervised Learning And Prediction Of Lines Of Therapy From High-Dimensional Longitudinal Medications Data," the contents of which are incorporated herein by reference in their entirety.

FIELD OF THE INVENTION

The present disclosure relates to computer-implemented methods and systems for labeling lines of therapy present in patient records, and more specifically, an unsupervised approach to labeling lines of therapy from medications data.

BACKGROUND

Line of Therapy (LoT) is standard nomenclature for discussing treatment with antineoplastic medications. Both the National Comprehensive Cancer Network and Association for Clinical Oncology (ASCO), groups which issue Standard of Care (SoC) treatment guidelines present their findings in the LoT framework. Oncologists consider these guidelines closely as they plan courses of treatment for their patients. Additionally, the LoT construct is considered by regulatory agencies, payers (both private and institutional), and provider groups as they plan for, approve, and pay for new anti-cancer medications. As such, pharmaceutical companies also approach their planning and trial design considering LoT and the potential impact/benefit for patients realized by their new medications. Doctors frequently recap patient history to another doctor by highlighting the LoT prescribed to the patient, any negative effects, progressions, or intervening events, and any subsequent changes to the LoT to compensate or adapt treatment to improve the patient's outcome. Unfortunately, this type of informal recap is never entered into a patient's electronic medical/health record (EMR/EHR). When physicians agree to provide a patient's EMR, it is desirable to parse through the records provided and pull out the LoTs, as well as significant, intervening (superseding) events (including progression, regression, metastasis, length of time) and provide them to the physician for their convenience and to improve physician understanding of the LoT history for each patient.

This is a difficult task to accomplish because the information recoverable from EHR and/or progress notes alone is never complete. There are a number of inaccuracies, inconsistencies, missing records, and other incomplete entries that may (or may not) appear in the record that need to be considered. For example, an oncologist may consider two LoTs: one with a combination of medications/treatments/therapies cyclophosphamide, doxorubicin, or paclitaxel as a line of therapy or sequence of a monotherapies. The patient's insurance provider may deny the employment of paclitaxel due to cost reasons, so the patient receives cyclophosphamide and doxorubicin. After a series of administrations, the patient may find this combination too detrimental to overall health, so the patient transitions to a maintenance therapy of paclitaxel alone. In the EMR, all of these medications may appear recorded for several months, even when the patient never even received paclitaxel for the first few entries in the EMR, and only had cyclophopsphamide for a portion of the time. Afterwards, the oncologist may order a CT scan to observe growth of the tumor. When the patient returns to the doctor six months later because their symptoms worsened, the doctor may note the symptoms worsening in the progress note as a progression event and list medications carboplatin and gemcitabine, or the doctor may only list medication gemcitabine, leaving the record ambiguous as to the previos medications. From an abstraction perspective, the EMR merely records that the prior medications were prescribed and six months later gemcitabine. The EMR may record a CT scan as well as the symptoms worsening around the six month time frame. The difficulty in developing LoTs from these records is manyfold:

1) If the patient never took, or discontinued, medications, then a LoT indicating that they were taken is not reliable from a data science perspective.

2) From an industry perspective, a change to a LoT that merely adjusts medications to avoid negative side effects to a medication is not a new LoT, but the same LoT. So medications changes are not always indicative of a new LoT. Identifying whether a change in medications coincides with a progression event, worsening symptoms, or any other significant intervening event may be tricky; for example, if the patient did not take a medication because of insurance issues or because of negative side effects, this may be difficult to rectify against worsening symptoms as a LoT change or merely avoiding negative side effects for the original LoT.

3) From a data science perspective, It may be difficult to impute whether medications were continued for the entire year in part or whole, even after a new medication was prescribed.

4) From a clinician perspective, certain drugs, while having a change in name, may be considered essentially the same drug.

5) Patients receive many medications as part of therapy, called 'supportive care' medications, that are irrelevant for LoT assignment. Further, differentiating these is not necessarily straightforward, as medications that are considered 'supportive care' versus 'primary care' differ by cancer type.

6) Data source heterogeneity. EHR and curation from progress notes differ from source to source and requires harmonization to a common standard prior to LoT determination.

7) Overcoming the burdens and complications of patchy data. Few patients have their cancer treatment records completely covered by both EHR and curated progress notes. Oftentimes, only one or the other is available, and when both are present, they describe discordant portions of the patient timeline. This complicates matters, especially when records commonly note the start of a set of medications, but rarely when they were stopped.

Currently, there does not exist any algorithm for predicting, digesting, or imputing LoTs from EMR. This generally requires a skilled practitioner manually reviewing the file to make these determinations on a case by case basis for every patient which is costly and time consuming. Machine learning may be applied to consider all medications across all patients based on their frequency, common occurrences of medications changes for certain diagnosis with intervening events that typically reflect a LoT may be predicted from incomplete data. To address this, a machine learning approach that synthesizes heuristics such as a rule based structure with clinical insights and an Expectation-Maximization (EM) algorithm to make effective predictions using machine learning algorithms (MLA) may be considered.

SUMMARY

In one aspect, the present disclosure provides a method for labeling one or more medications concurrently administered to a patient as a line of therapy. The method includes identifying medical records of the patient from a plurality of digital records, a subset of the medical records reflecting medical history of the patient with respect to one or more treatments after a disease state diagnosis of the patient, creating, from the subset of medical records, a plurality of treatment intervals including at least one medication administered to the patient and a time interval, associating medications of the one or more treatments with a respective treatment interval when the administration of the medication falls within the time interval, refining the time interval of a respective treatment interval when a treatment of the one or more treatments falls outside the time interval but within an extension period and wherein an interval superseding event does not take place during the refined time interval, identifying, via an unsupervised artificial intelligence engine, one or more potential lines of therapy from the plurality of treatment intervals, each potential line of therapy including one or more of the plurality of treatment intervals and a maximum likelihood estimation, and labeling, via the unsupervised artificial intelligence engine, the potential line of therapy having the highest maximum likelihood estimation as the line of therapy.

The method may further include labeling, via the unsupervised artificial intelligence engine, additional potential lines of therapy during successive time intervals as an incrementally numbered line of therapy from the potential lines of therapy occurring chronologically after each preceding line of therapy and having the respective highest maximum likelihood estimation of the potential lines of therapy in each successive time interval. The method may further include labeling, via the unsupervised artificial intelligence engine, respective incrementally numbered lines of therapies for a plurality of patients, identifying a plurality of cohorts of patients, and reporting the incrementally numbered lines of therapies for each of the plurality of cohorts of patients. The method may further include reporting institution-wide and physician-specific compliance to standardized treatment guidelines. The method may further include reporting changes to lines of therapies over time based at least in part on the respective time intervals of each line of therapy. The method may further include reporting analytics on therapeutic impact differences between a first cohort of patients and a second cohort of patients, wherein a cohort identifies patients as having one or more similar dates of treatment, lines of therapy, diagnosis, outcomes, geographic locations, treating physicians, treating institutions, genomic markers, or clinical characteristics. The method may further include reporting analytics on progression-free survival between the first cohort and second cohort. The method may further include generating a progression-free survival curve for a first cohort of patients having at least one labeled line of therapy in common, generating a progression-free survival curve for a second cohort of patients having at least one other labeled line of therapy in common, and displaying the progression-free survival curve for the first cohort and the second cohort on the same survival graph. In the method, a labeled line of therapy may include one or more of medication name, treatment roll-up class, dosage, or method of administration.

The method may further include generating a report, the report including each line of therapy labeled for the patient and the respective time interval.

In the method, disease state diagnoses may include cancer, cardiology, depression, mental health, diabetes, infectious disease, epilepsy, dermatology, and autoimmune diseases.

In the method, the disease state diagnosis may be cancer.

In the method, the plurality of digital records may include one or more EHR medical records and one or more curated medical records. In the method, a curated medical record may be an image of a record not included in the one or more EHR medical records. The method may further include digitizing, optical character recognizing, and encoding the curated medical record into a structured format.

The method may further include identifying, by a treatment identifier, a treatment that was administered to the patient and an administration date on which the treatment was administered.

In the method, treatment may include one or more of administration of a medication, a drug, a molecule, or a chemical, implantation of a medical device, use of a medical device, use of a biotherapy, a virotherapy, a phage therapy, a phytotherapy, a gene therapy, an epigenetic therapy, a protein therapy, an enzyme replacement therapy, a hormone therapy, a cell therapy, an immunotherapy, an antibody therapy, a nutrition therapy, an electromagnetic radiation therapy, or a radiation therapy, a surgical procedure, or a radiosurgery.

In another aspect, the present disclosure provides a system for labeling one or more medications concurrently administered to a patient as a line of therapy. The system includes at least one computer having at least one processor programmed to identify medical records of the patient from a plurality of digital records, wherein a subset of the medical records reflect medical history of the patient with respect to one or more treatments after a disease state diagnosis of the patient, create, from the subset of medical records, a plurality of treatment intervals including at least one medication administered to the patient and a time interval, associate medications of the one or more treatments with a respective treatment interval when the administration of the medication falls within the time interval, and refine the time interval of a respective treatment interval when a treatment of the one or more treatments falls outside the time interval but within an extension period and wherein an interval superseding event does not take place during the refined time interval, the at least one computer including an unsupervised artificial intelligence engine programmed to identify one or more potential lines of therapy from the plurality of treatment intervals, each potential line of therapy including one or more of the plurality of treatment intervals and a maximum likelihood estimation, and label the potential line of therapy having the highest maximum likelihood estimation as the line of therapy In the system, the unsupervised artificial intelligence engine may be programmed to label additional potential lines of therapy during successive time intervals as an incrementally numbered line of therapy from the potential lines of therapy occurring chronologically after each preceding line of therapy and having the respective highest maximum likelihood estimation of the potential lines of therapy in each successive time interval. In the system, the unsupervised artificial intelligence engine may be programmed to label respective incrementally numbered lines of therapies for a plurality of patients, identify a plurality of cohorts of patients, and report the incrementally numbered lines of therapies for each of the plurality of cohorts of patients. In the system, the at least one computer may be further programmed to report institution-wide and physician-specific compliance to standardized treatment guidelines. In the system, the at least one computer may be programmed to report changes to lines of therapies over time based at least in part on the respective time intervals of each line of therapy. In the system, the at least one computer may be further programmed to report analytics on therapeutic impact differences between a first cohort of patients and a second cohort of patients, a cohort identifying patients as having one or more similar dates of treatment, lines of therapy, diagnosis, outcomes, geographic locations, treating physicians, treating institutions, genomic markers, or clinical characteristics. In the system, the at least one computer may be further programmed to report analytics on progression-free survival between the first cohort and second cohort. In the system, the at least one computer may be further programmed to generate a progression-free survival curve for a first cohort of patients having at least one labeled line of therapy in common, generate a progression-free survival curve for a second cohort of patients having at least one other labeled line of therapy in common, and display the progression-free survival curve for the first cohort and the second cohort on the same survival graph. In the system a labeled line of therapy may include one or more of medication name, treatment roll-up class, dosage, or method of administration.

In the system, disease state diagnoses may include cancer, cardiology, depression, mental health, diabetes, infectious disease, epilepsy, dermatology, and autoimmune diseases.

In the system, the plurality of digital records may include one or more EHR medical records and one or more curated medical records. In the system, the at least one computer may be further programmed to digitize, optical character recognize, and encode the curated medical record into a structured format.

In the system, a treatment may include one or more of administration of a medication, a drug, a molecule, or a chemical, implantation of a medical device, use of a medical device, use of a biotherapy, a virotherapy, a phage therapy, a phytotherapy, a gene therapy, an epigenetic therapy, a protein therapy, an enzyme replacement therapy, a hormone therapy, a cell therapy, an immunotherapy, an antibody therapy, a nutrition therapy, an electromagnetic radiation therapy, or a radiation therapy, a surgical procedure, or a radiosurgery.

FIGURES

DETAILED DESCRIPTION

The phrase "disease state" means a state of disease, such as cancer, cardiology, depression, mental health, diabetes, infectious disease, epilepsy, dermatology, autoimmune diseases, or other diseases. A disease state may reflect the presence or absence of disease in a subject, and when present may further reflect the severity of the disease.

Figure 1:
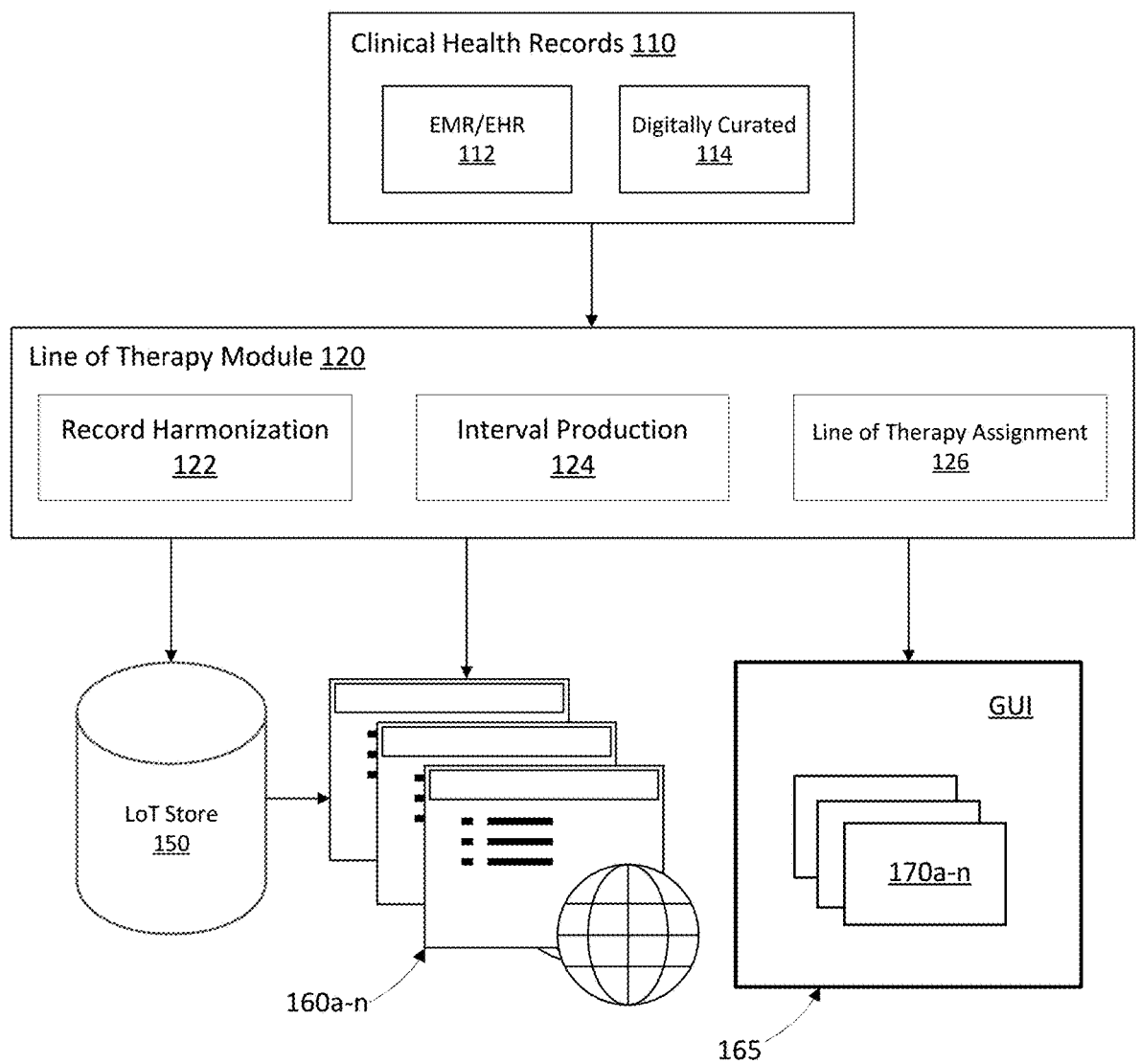
FIG. 1 is a flowchart depicting an embodiment of preparing, training, and generating Line of Therapy (LoT) predictions.

FIG. 1 illustrates an embodiment of a computer-implemented system 100 for labeling lines of therapy for patients based on their medications administered and clinical records. Lines of therapy may be generated from patient information represented by clinical health records 110 implemented by the system architecture 100. The system 100 can be a content server (also referred to as a LoT engine), which is hardware or a combination of both hardware and software. A user, such as a health care provider or patient, is given remote access through the GUI 170a-n to view, update, and analyze information about a patient's medical condition using the user's own local device (e.g., a personal computer or wireless handheld device). A user can interact with the system to instruct it to generate electronic records, update the electronic records, and perform other actions. The content server is configured to receive various information in different formats and it converts the information into the standardized format that is suitable for processing by line of therapy module 120 operation on or in conjunction with the content server. Thus, information acquired from patients' electronic medical records (EMR), unstructured text, genetic sequencing, imaging, and various other information can be converted into features that are used for training one or more artificial intelligence engines or machine-learning models.

The information acquired, processed, and generated by the content server 100 is stored on one or more of the network-based storage devices. The user can interact with the content server to access the information stored in the network-based storage devices, and the content server can receive user-supplied information, apply the one or more models stored in the network-based storage to the information, and to provide, in an electronic form, results of the model application to the user on a graphical user interface of the user device. The electronic information is transmitted in a standardized format over the computer network to the users that have access to the information. In this way, the users can readily adapt their medical diagnostic and treatment strategy in accordance with the system's predictions which can be automatically generated. Moreover, the system generates recommendations to users regarding patient diagnosis and treatment.

In some embodiments, the described systems and methods are implemented as part of a digital and laboratory health care platform. The platform may automatically generate a molecular report as part of a targeted medical care precision medicine treatment. In some embodiments, the system in accordance with embodiments of the present disclosure operates on one or more micro-services, which can be micro-services of an order management system. In some embodiments, the system is implemented in conjunction with one or more micro-services of a cell-type profiling service.

The clinical health records 110 may store a collection of features, or status characteristics, generated for some or all patients whose information is present in the system 100. These features may be used to identify medications and superseding events using the system 100. While feature scope across all patients is informationally dense, a patient's feature set may be sparsely populated across the entirety of the collective feature scope of all features across all patients. For example, the feature scope across all patients may expand into the tens of thousands of features, while a patient's unique feature set may include a subset of hundreds or thousands of the collective feature scope based upon the records available for that patient.

A plurality of features present in the clinical health records 110 may include a diverse set of fields available within patient health records. Clinical information may be based upon fields which have been entered into an electronic medical record (EMR) or an electronic health record (EHR) 112, which can be done automatically or manually, e.g., by a physician, nurse, or other medical professional or representative. Other clinical information may be digitally curated information 114 obtained from other sources, such as, for example, genetic sequencing reports (e.g., from molecular fields), progress reports, testing results, insurance billing codes and/or records, and other medical documentation for a patient. Sequencing may include next-generation sequencing (NGS) and may be long-read, short-read, or other forms of sequencing a patient's somatic and/or normal genome. A comprehensive collection of features in additional clinical health records may combine a variety of features together across varying fields of medicine which may include diagnoses, responses to treatment regimens, genetic profiles, clinical and phenotypic characteristics, and/or other medical, geographic, demographic, clinical, molecular, or genetic features. For example, a subset of features may comprise molecular data features, such as features derived from RNA or DNA sequencing, pathology features derived from cellular review by a pathologist, or other imaging.

Imaging features may comprise features identified through review of a specimen by pathologist, such as, e.g., a review of stained H&E or IHC slides. As another example, a subset of features may comprise derivative features obtained from the analysis of the individual and combined results of such feature sets. Features derived from DNA and RNA sequencing may include genetic variants which can be identified in a sequenced sample. Further analysis of the genetic variants may include steps such as identifying single or multiple nucleotide polymorphisms, identifying whether a variation is an insertion or deletion event, identifying loss or gain of function, identifying fusions, calculating copy number variation, calculating microsatellite instability, calculating tumor mutational burden, or other structural variations within the DNA and RNA. Analysis of slides for H&E staining or IHC staining may reveal features such as tumor infiltration, programmed death-ligand 1 (PD-L1) status, human leukocyte antigen (HLA) status, or other immunology-related features.

Features derived from structured, curated, and/or electronic medical or health records 112 and 114 may include clinical features such as diagnosis, symptoms, therapies, outcomes, patient demographics such as patient name, date of birth, gender, ethnicity, date of death, address, smoking status, diagnosis dates for cancer, illness, disease, diabetes, depression, other physical or mental maladies, personal medical history, family medical history, clinical diagnoses such as date of initial diagnosis, date of metastatic diagnosis, cancer staging, tumor characterization, tissue of origin, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/statuses, or corresponding dates associated with any of the above.

Machine learning models and/or an artificial intelligence engines may perform classifications labeling, and/or analytics by selecting from any features. One method for enhancing a patient's feature set may include dimensionality reduction, such as collapsing a feature set from tens of thousands of features to a handful of features. Performing dimensionality reduction without losing information may be approached in an unsupervised manner or a supervised manner. Unsupervised methods may include RNA Variational Auto-encoders, SVD, PCA, KernelPCA, SparsePCA, DictionaryLearning, Isomap, NMF, UMAP, Feature agglomeration, Patient correlation clustering, KMeans, Gaussian Mixture, or Spherical KMeans. Performing dimensionality reduction in a supervised manner may include Linear Discriminant Analysis, Neighborhood Component Analysis, MLP transfer learning, or tree based supervised embedding.

Machine learning models or artificial intelligence engines may be implemented via gradient boosting models, random forest models, neural networks (NN), regression models, Naïve Bayes models, or machine learning algorithms (MLA). A MLA or a NN may be trained from a training data set such as a plurality of matrices having a feature vector for each patient or images and features. In an exemplary prediction profile, a training data set may include imaging, pathology, clinical, and/or molecular reports and details of a patient, such as those curated from an EHR or genetic sequencing reports. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models where the training data set includes a plurality of tumor samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA and an artificial intelligence engine may embody one or more of each in a hierarchical architecture unless explicitly stated otherwise.

In some embodiments, the artificial intelligence engine can be a trained machine learning model. In some embodiments, the trained machine learning model can be generated by training a machine learning model on medical records having one or more LoTs. In some embodiments, the trained machine learning model can be a regression model. In some embodiments, the trained machine learning model can be a clustering model. In some embodiments, the trained machine learning model can be a dimensionality reduction model. In some embodiments, the trained machine learning model can be a classification model.

Training may include providing optimized datasets as a matrix of feature vectors for each patient, labeling these traits as they occur in patient records as supervisory signals, and training the MLA to predict an output classification, prediction, or label. Artificial NNs are powerful computing models which have shown their strengths in solving hard problems in artificial intelligence. They have also been shown to be universal approximators (can represent a wide variety of functions when given appropriate parameters). Some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule based schema to generate more complicated predictions, such as predictions based upon multiple features. For example, ten key features may be identified across different classifications. A list of coefficients may exist for the key features, and a rule set may exist for the classification. A rule set may be based upon the number of occurrences of the feature, the scaled weights of the features, or other qualitative and quantitative assessments of features encoded in logic known to those of ordinary skill in the art. In other MLA, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. A single instance of the above models, or two or more such instances in combination, may constitute a model for the purposes of models or engines described herein.

Line of therapy module 120 may comprise a plurality of modules: record harmonization 122, interval production 124, and line of therapy assignment 126. Record harmonization module 122 may harmonize the records contained in the EMR 112 and digitally curated records 114 to remove duplicates, combine similar records, and take additional harmonization steps as disclosed in more detail below with respect to FIG. 3. Interval production module 124 may receive harmonized records and generate and refine a plurality of treatment intervals based on the harmonized records as disclosed in more detail below with respect to FIG. 4. Line of therapy assignment module 126 may receive the plurality of treatment intervals, identify potential lines of therapy and apply a trained artificial intelligence engine to the potential lines of therapy to identify and label one or more lines of therapy administered to the patient.

Line of therapy (LoT) store 150 may receive LoTs generated from LoT module 120 and store them for use in the system 100. LoTs may be stored in a structured format for retrieval by a user interface such as, for example, a webform-based interactive user interface which, in some embodiments, may include webforms 160*a-n*. Webforms may support GUIs that can be displayed by a computer to a user of the computer system for performing a plurality of analytical functions, including initiating or viewing the instant LoTs from module 120 or initiating or adjusting the cohort of patients from which the module 120 may perform analytics from. Electronic reports 170*a-n* may be generated and provided to the user via the graphical user interface (GUI) 165. It should be appreciated that the GUI 165 may be presented on a user device which is connected to the content server/prediction engine 100 via a network.

The reports 170*a-n* can be provided to the user as part of a network-based patient management system that collects, converts and consolidates patient information from various physicians and health-care providers (including labs) into a standardized format, stores it in network-based storage devices, and generates messages comprising electronic reports once the reports are generated in accordance with embodiments of the present disclosure. In this way, a user (e.g., a physician, oncologist, or any other health care provider, or a patient, receives computer-generated predictions, analytics, and other reports relating to the generated LoT.

In some embodiments, the electronic report may include a recommendation to a physician to treat the patient using a next LoT or treatment that correlates with a predicted response based on responses of similar patients having undergone similar treatments.

Figure 2:
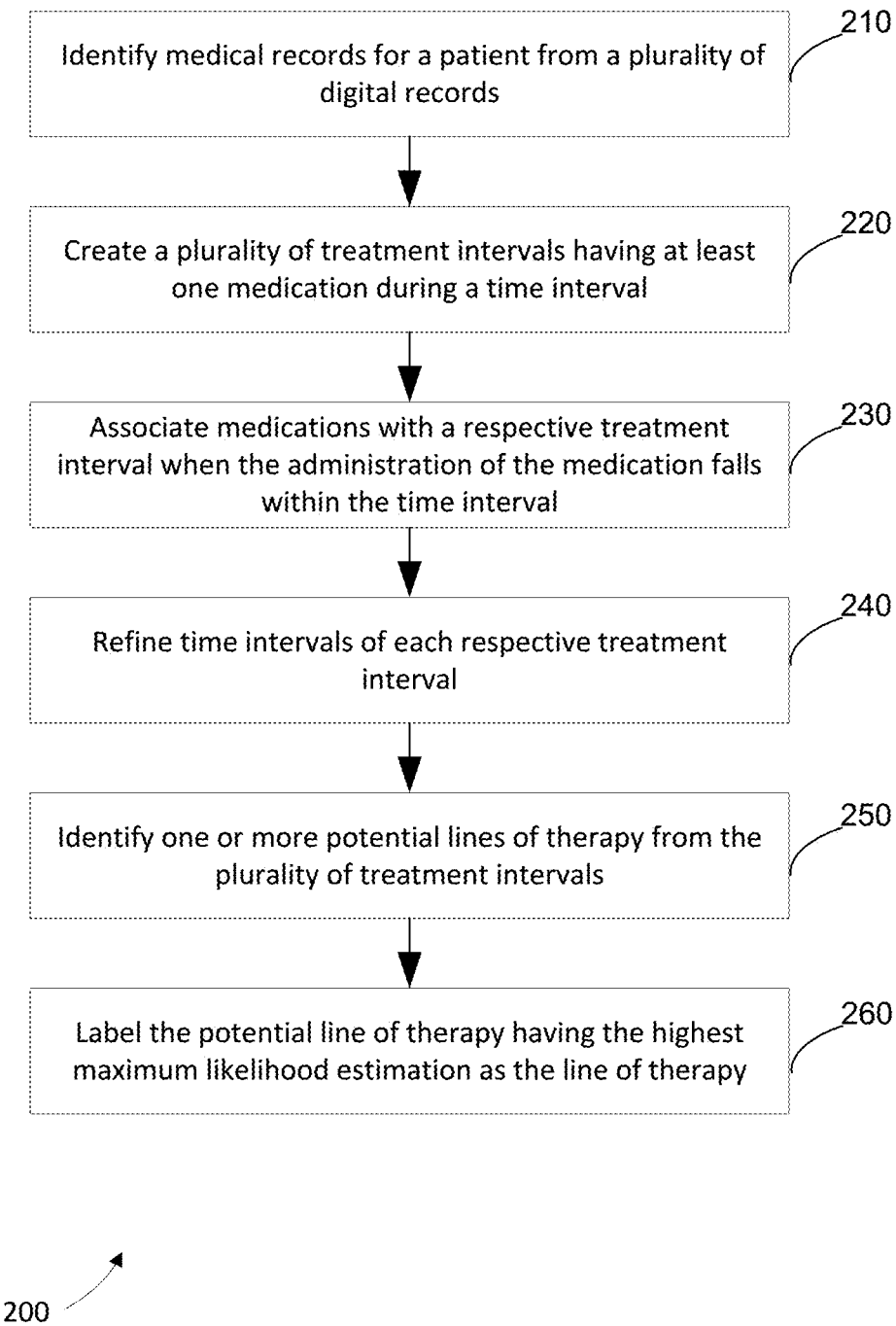
FIG. 2 is a flowchart depicting an embodiment of preparing, training, and generating Line of Therapy (LoT) predictions using a MLA approach with rule-based pre-processing.

FIG. 2 illustrates a flow chart of a method for generating one or more lines of therapy from a plurality of digital records. At step 210, a system 200 may identify medical records for a patient from a plurality of digital records. These records may be recorded in an EMR/EHR or be digitally curated from unstructured data. Medical records may be limited to those from a specific time period, include a time period starting from a diagnosis of a disease state such as cancer. Additional time periods may include specific yearly intervals when performing an analysis of LoT development over time.

At step 220, the system 200 may create a plurality of treatment intervals having at least one medication during a time interval. The medications as identified from the patient records and further identified as relevant to the diagnosis. Time intervals may be associated with a start and/or end date, dates may be directly assigned from the patient record or imputed from additional supporting information such as similar medications, standard practice, or learned intervals from an artificial intelligence engine trained on similar patient records.

At step 230, the system 200 may associate medications with a respective treatment interval when the administration of the medication falls within the time interval. For example, if a treatment interval exists for June $1^{st}$ through June $23^{rd}$, a respective medication administered on June $15^{th}$ may be associated with the treatment interval, however a medication administered on September $1^{st}$ may not be associated with the treatment interval because the administration does not fall within the time interval.

At step 240, the system 200 may refine time intervals of each respective treatment interval. Time intervals may be refined by combining overlapping intervals, splitting intervals up, or adjusting the start and/or end dates according to one or more heuristics, rules, or trained models.

At step 250, the system 200 may identify one or more potential lines of therapy from the plurality of treatment intervals. Identification may be performed using a trained model, an exhaustive enumeration with ranking based on likelihood, or other method as disclosed herein.

At step 260, the system 200 may label the potential line of therapy having the highest maximum likelihood estimation as the line of therapy. For example, given a ranked list of potential lines of therapy, the line of therapy having the highest ranking (most confidence) may be selected as the line of therapy.

Figure 3:
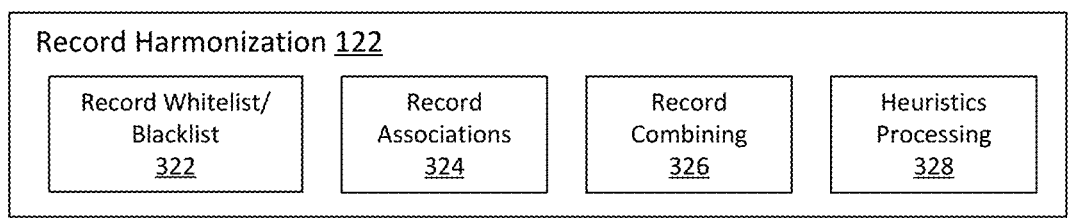
FIG. 3 is an illustration of a LoT prediction for a first patient diagnosed with metastatic non-small cell lung cancer.

FIG. 3 illustrates exemplary record harmonization modules 300 for implementing sub processes of record harmonization 122 of FIG. 1.

Record harmonization may include one or more modules such as record whitelists and/or record blacklists module 322, record association module 324, record combining module 326, and heuristics processing module 328.

Record whitelists and/or record blacklists module 322 may include or exclude records based on their content, quality, reliability, or other evaluation metrics. For example, records may be included when their source may be identified as imaging results from a respected institution, excluded if the image resolution falls below an acceptable threshold for readability, or excluded if the record contains patient mismatch such as a mismatch in gender, race, or other immutable characteristics/demographics.

Record associations module 324 may check records for redundancy and remove records that appear more than once or that contain the same information as other records. Associations with medications, medication start dates, or medication end dates may be assigned or imputed.

Record combining module 326 may combine records with sufficiently overlapping associations. Sufficiently overlapping associations may include the same medication or similar medications (such as generic vs brand name, competing brand names, known equivalents, or other similarities). Multiple records having the same start date for similar medications may be 'rolled-up' into a single record.

Heuristics processing module 328 may incorporate a rule based or artificial intelligence driven record harmonization structure. In one example, an artificial intelligence engine may be trained on medication names to identify similar medications, or be trained on medication intervals to predict the duration a medication is most commonly prescribed to a patient for each medication type. The model may additionally include rule sets for applying a set threshold to the assignment of start dates, end dates, or enforcing a minimum or maximum time period for each record.

Additional record harmonization steps are disclosed below with respect to Data Intake and Harmonization.

Figure 4:
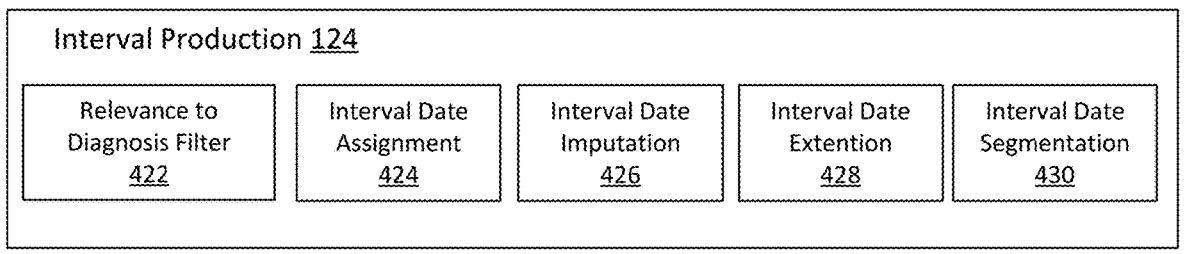
FIG. 4 is an illustration of a LoT prediction for a second patient diagnosed with ovarian cancer.

FIG. 4 illustrates exemplary interval production modules 400 for implementing sub processes of interval production 124 of FIG. 1.

Interval production may include one or more modules such as relevance to diagnosis filter 422, interval date assignment 424, interval date imputation 426, interval date extension 428, or interval date segmentation 430.

Relevance to diagnosis filter 422 may incorporate a knowledge database comprising medications which are known to treat a diagnosis. These medications may be curated from FDA approvals, clinical trials, publications, or from artificial intelligence analysis on patient records. Medications which are not relevant to treatment of the diagnosis may be excluded from processing for LoT because they are not likely to be administered for the purposes of treating the diagnosis.

Interval date assignment 424 may include assigning an interval to each medication record which has not been deleted from one of the preceding modules during record curation, harmonization, or relevance filtering. A medical record which comprises a medication and at least a start date may be assigned to an interval having no medication or the same or similar medication.

Interval date imputation 426 may include imputing the start or end date for an interval to reflect an accurate estimation of the administration of the medication(s) of the interval. For example, if a medication is expected to continue for a set number of days (a course of antibiotics, steroids, or other medication having known periodicity), then an end date may be imputed for the interval the respective medication is assigned to based on the expected duration such as 7 days later, 14 days later, 3 months later, etc.

Interval date extension 428 may include identifying when successive intervals overlap and extending the duration of the first overlapping interval to encompass the other overlapping intervals when the medications are the same or similar. Additionally, when medications are assigned or imputed for an interval, the start date or end date of a respective interval may be extended to include the dates of the additional medication when the extension falls within a threshold period of time. In one example, the threshold period of time may include a set duration such as 22 days or a per medication period of time based upon the medication(s) of the interval, similar to record combining 326, above.

Interval date segmentation 430 may include identifying when an interval superseding event occurs during one or more intervals and splits each respective interval at the date of the superseding event. For example, in a cancer diagnosis, the occurrence of metastasis may be referenced as an interval superseding event and any intervals extending beyond the date of metastasis may be split into a first interval having the original interval start date and the date of metastasis as the end date and a second interval having the date of metastasis as the interval start data and the original interval end date. Superseding events include events which cause a line of therapy change and may be identified through artificial intelligence analysis of patient records, via a rule set, or through those events as may be curated from FDA approvals, clinical trials, publications.

Figure 5:
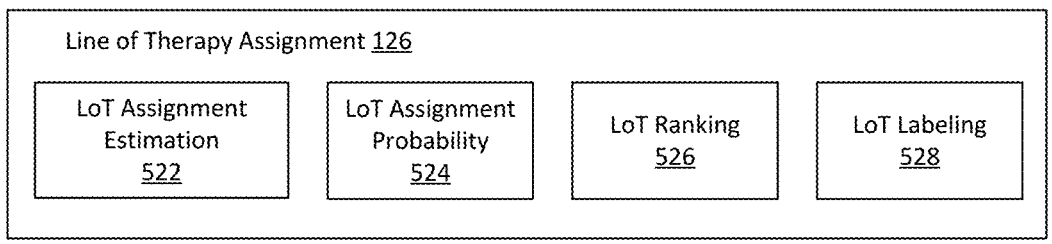
FIG. 5 is an illustration of a LoT prediction for a third patient diagnosed with breast cancer.

FIG. 5 illustrates exemplary line of therapy assignment modules 400 for implementing sub processes of line of therapy assignment 126 of FIG. 1.

Line of therapy assignment may include one or more modules such as LoT assignment estimation 522, LoT Assignment probability 524, LoT ranking 526, or LoT labeling 528.

LoT assignment estimation 522 may include performing a composition of integer evaluation of the available intervals such that each interval may be considered in part and as a whole to each other interval to identify potential lines of therapy. In another embodiment, an artificial intelligence engine may receive the plurality of the treatment intervals and output a plurality of potential lines of therapy.

LoT Assignment probability 524 may include calculating the expectation maximum probability of each potential line of therapy to identify a likelihood that each potential line of therapy should be included as a successively numbered line of therapy (first line of therapy, second line of therapy, third line of therapy, and so forth).

LoT ranking 526 may include ranking the plurality of potential lines of therapy based on their likelihoods such that the potential lines of therapy having the highest probability are at the top of the ranking and the potential lines of therapy having the lowest probability are at the bottom of the ranking.

LoT labeling 528 may include identifying the most likely potential line of therapy as the line of therapy or evaluating successive potential lines of therapy to identify successive incrementally numbered lines of therapy occurring chronologically after each preceding line of therapy and having the respective highest maximum likelihood estimation of the potential lines of therapy in each successive time interval. For example, if a first potential line of therapy starts in January and a second potential line of therapy starts in May, the first potential line of therapy may be labeled first line of therapy and the second potential line of therapy may be labeled as the second line of therapy when both lines of therapy are the respectively highest ranked potential line of therapy in intervals before May and after May. Additionally, an artificial intelligence engine may be trained to identify and label a line of therapy and/or iteratively successive lines of therapy.

The modules of FIGS. 3-5 may be configured to perform one or more of the following steps or processes.

In one example, a set of rules may guide the process of labeling one or more LoT from the records of a patient. Rules may include one or more "hard" rules or "soft" rules.

Hard Rules

After initial diagnosis of prostate cancer, it may be commonplace to prescribe and administer leuprolide to the patient for life. So once leuprolide occurs in the EMR, it may always remain as part of the LoT, even if the LoT changes. Another exemplary hard rule may include certain intervening events that require a change of LoT, such as a treatment discontinuation, metastases, or progressive disease outcome. The opposite may also be encoded as a hard rule. For example, a patient with a recorded medication change to abemaciclib generally only occurs due to metastasis of breast cancer. Even if the EMR is incomplete and does not recite that the patient's cancer spread through metastasis, it may be imputed and added to the EMR as well as segmenting the respective treatment interval, potential LoT, or LoT upon detection. Similarly, progression from one class of drugs to another class of drugs may also be implemented as a hard rule forcing the segmentation of the respective treatment interval, potential LoT, or LoT.

Soft Rules

When rules may be formed but are conditionally applied, they may be encoded as soft rules. In one example, it may be noted that oncologists each define LoTs differently: some may see carboplatin and cisplatin together as a LoT, but subsequent maintenance pembrolizumab as not a core part of the LoT. others may consider cisplatin and carboplatin along with the maintenance pembrolizumab together as one LoT. Some may consider any deviation, even if for side effect avoidance, as a new LoT, while others may not. These types of preferences may be generated as soft rules that give additional weight to a LoT but do not require a new LoT be generated upon seeing in the EMR. If two medications are similar, such as they have the same active ingredient, or accomplish the same effect with different active ingredients, a change from one to the other may be weighed to determine the presence of a LoT change. Further, the preference for application of one soft rule to another may be recorded and applied on a physician-by-physician or institution-by-institution basis such that a specific soft rule may be conditionally applied based on the patient being under the care of a particular physician or institution which opted in to using the soft rule Algorithm Methodology and Sample Output In one approach, the EMR and curated progress reports may be parsed for all diagnosis, medications, significant events and other features which may be relevant to identifying any LoTs based on combinations of medications, significant events, and other combinations of medications. The MLA functions in two major steps. The first step consists of synthesizing and harmonizing disparate data sources, including medications, outcomes, diagnoses, across EHR and curated progress notes, to create unique intervals of patient care. The second step considers all possible combinations of these intervals and assigns LoT accordingly. In a lexicographic example where a medication history is represented as a string of characters, THECATSAT, each character may represent a combination of unique medications after digestion by the first step. After training across patient data, the goal of the second step is to recognize common medication patterns, taking into account heuristics, and separate this to "THE"+"CAT"+"SAT". Examples based on patient EMR are discussed below with respect to FIGS. 8-13F Model Training Model training may consist of defining unique treatment intervals (letters' from the above example, like 'T' or 'H') for each patient in a large training cohort and iteratively considering all combinations of aggregation (T+HEC+AT versus THE+CAT), assigning these aggregations, calculating the frequency of these resultant aggregations (words), and re-assigning aggregations until an end condition is reached. These combinations of aggregations are enumerated using a composition of an integer approach. In a simplified example having a LoT representation of 5 such medications, using a composition of an integer approach to divide up into sixteen different possible LoT groupings.

The sixteen compositions of 5 are:
5
4+1
3+2
3+1+1
2+3
2+2+1
2+1+2
2+1+1+1
1+4
1+3+1
1+2+2
1+2+1+1
1+1+3
1+1+2+1
1+1+1+2
1+1+1+1+1.

This frequency analysis may be combined with the hard/soft rules in conjunction with diagnosis information, clinical information, and significant events to provide a comprehensive probability estimation for each composition. This most likely composition (THE+CAT+SAT) is then output as the assigned LoT.

One goal is to identify the cut points in this character string, such that it reads THE|CAT|SAT, after studying a large corpus of text. It could be that such a problem is easier if each character in the alphabet were mapped to some lower-level hierarchy, such as consonants (C) and vowels (V), so the above reads T→C, H→V, E→C, C→C, A→V, T→C, S→C, A→V, T→C. In this case, it is much easier to learn the separators CVC|CVC|CVC. To this end, the Anatomical Therapeutic Chemical (ATC) Classification System is a drug classification system that classifies the active ingredients of drugs according to the organ or system on which they act and their therapeutic, pharmacological and chemical properties. It is controlled by the World Health Organization Collaborating Centre for Drug Statistics Methodology (WHOCC), and was first published in 1976. This pharmaceutical coding system divides drugs into different groups according to the organ or system on which they act, their therapeutic intent or nature, and the drug's chemical characteristics. Different brands share the same code if they have the same active substance and indications. Each bottom-level ATC code stands for a pharmaceutically used substance, or a combination of substances, in a single indication (or use). This means that one drug can have more than one code, for example acetylsalicylic acid (aspirin) has A01AD05 (WHO) as a drug for local oral treatment, B01AC06 (WHO) as a platelet inhibitor, and N02BA01 (WHO) as an analgesic and antipyretic; as well as one code can represent more than one active ingredient, for example C09BB04 (WHO) is the combination of perindopril with amlodipine, two active ingredients that have their own codes (C09AA04 (WHO) and C08CA01 (WHO) respectively) when prescribed alone. The ATC classification system is a strict hierarchy, meaning that each code necessarily has one and only one parent code, except for the 14 codes at the topmost level which have no parents. The codes are semantic identifiers, meaning they depict in themselves the complete lineage of parenthood. The ATC hierarchy provides a 3 and 4th-level hierarchy for a given medication. If one could re-map each medication to this hierarchy, improvements in defining LoTs in these simpler representations may be realized, especially in contexts where the data set is smaller, or there is an extremely high medication cardinality. Specific cases of interest may be hormone maintenance therapies and other therapies, which are extremely common in one cancer, but difficult to learn using conventional MLA techniques.

For example, in breast cancer LoT, a cohort may have approximately 55 unique antineoplastic medications relevant to breast cancer. Grouping these medications to their underlying ATC Hierarchy, either through level 3 or 4, results in a significant reduction in this medication space of 20 under ATC level 4 and 9 under ATC level 3. Where the number of identified LoT states (classifications of LoT from across the entire patient set in breast cancer) is 1117 using only medication names, 656 under ATC level 4, and 289 under ATC level 3. Roughly, as one employs increasingly non-specific medication groupings, the number of unique 'medications' decreases by 2×, and accordingly, the number of medication states in the output model accordingly decreases by roughly 2×.

The equivalencies provided by the ATC hierarchy was primarily implemented to solve the 'maintenance' problem observed in breast cancer. One often sees patients with first line chemotherapy (doxycycline and cyclophosphamide) followed by tamoxifen or anastrozole (hormone therapies), which is all considered one LoT. However, pure frequency based approaches at identifying LoT from underlying patient data nearly always says the chemotherapy and the hormone therapy are separate LoT because hormone therapy is ubiquitous, such that half of all patient medication states are hormone therapies (i.e., if a patient is on at least one medication, half the time it's a hormone therapy), and secondly, a patient that receives chemotherapy as a first line will go on hormone therapy within 180 days, half of the time. Referring back to the word example (THECATSAT), this is like saying one sees E nearly all the time, and TH at a regular pace, with THE nearly half the time. In a pure frequency, TH|E will be the result. This is because prob(TH)*(E)>prob(THE), partially due to the ubiquity of E (prob(E) high). Really, this is because one observes hundreds of variations where E is afterward, or simply E. In this case, one would think that E is only a single character.

Therefore, the maintenance problem is result of a core problem in pure frequency models; when E occurrences do not matter, and secondly, that if E is seen alone commonly, and TH, that it must always be separate, when in some cases it could actually be one 'word.' Both of these can be encoded into a probability representation: THE is a word if prob_1(TH)*prob_2(E)<prob_1(THE), where prob_1 indicates the probability of observing a given letter first (1), second (2), etc. The latter can also be encoded as the 'word-ness' of THE is if prob(E|TH)>prob(X|TH)*prob(E|X); i.e., given TH is previous, is the presence of E significantly higher than random chance (or any other given medication, X), possibly modulated by the frequency of E?

Selecting which model to implement is a case of evaluating the performance of the underlying system. Lines of therapy are often the result of NCCN guidelines, wherein an oncologist chooses, with little variation, a 'plan' at a given time, and changes this once an outcome is observed, and/or the patient responds poorly to the therapy. Accordingly, the latter is a more apt means of representing the probability space. The former representation implies that prob_1(TH)*prob_2(E) !=prob_2(TH)*prob_3(E), which means that the temporal ordering strictly changes the probabilities. While this is likely the case as well, the more desirable feature to capture is that seeing E or TH alone isn't important to predicting whether THE is a word, but rather comparing TH(X) and (Z)E, and whether there is a significant enrichment when X=E and Z=TH.

As described above, a probability model, in its raw form, has an unclear mapping to how one would normally impute progression events. In the worst case, there are times when imputes a progression event consistently when one would almost never actually see a progression event. In order to provide a greater concordance between the model and outcomes, an enhanced model and corresponding model training is conducted with the following underlying probability model:

$$\text{prob}(A \rightarrow B) = \text{prob}(A)*\text{prob}(B)*\text{prog\_w}(A,B) \text{ vs. prob}(AB)*[1-\text{prog\_w}(A,B)],$$

where prog_w(A,B) represents an estimation of the observed progression incidence between medication states A and B. What the above states is instituting a LoT break is modified by the incidence of progressions one typically observes in the transition from A→B; the more common, the more likely this state is in comparison to the situation where the two are one LoT. The model may implement prog_w(A,B) as the number of progressions observed at this transition over the total number of times one observes this transition. However, the vast majority of transitions are fairly unobserved, so this would significantly bias the model. A 'Bayesian' estimate that tends toward 0.5 (i.e., lets the underlying frequency space of the model decide, rather than the progression incidence). The larger the sample size, the more one wants to use the observed estimate, the smaller, the more one wants to use 0.5. A classic method of implementing this is additive smoothing where prog_w may be:

$$\text{prog\_}w(A \rightarrow B) = (\text{prog\_}f) \pm \text{abs}(\text{prog\_}f - 0.5)*(\text{upper\_95}(\text{prog\_}f) - \text{lower\_5}(\text{prog\_}f)),$$

where prog_f is the number of progressions observed in the transition from A→B divided by the overall incidence, and upper_95(prog_f), lower_5(prog_f) is the 95th and 5th binomial proportion CI estimate based on the Clopper Pearson method for prog_f. As the sample size increases, the confidence intervals near 0, so the 'centering' applied to prog_f decreases. As the sample size increases, the confidence intervals diverge (maximum 1.0), meaning the maximum shift is applied, and prog_w trends toward 0.5.

The ATC and enhanced model shows the highest concordance with common transitions. Most significantly, the model now shows the least significant contradictions with the data (trastuzumab→trozole), with an incidence of 1/139 in the data compared to 30 in 319 in the output, which is an extremely small difference, or an injection of ~29 additional events such as taxane→trozole. This is an extremely common transition from a strong and fast initiation therapy, such as chemotherapy to a maintenance therapy. Advantages of the instant LoT labeling artificial intelligence engine allow nuances in soft rules to cover the three LoTs possible based on the requesting entity. The LoTs possible including the initiation therapy, the maintenance therapy, or the combination of an initiation therapy and the maintenance therapy.

Therefore, the enhanced model removes false LoT changes around maintenance therapies, or reduces the incidence of contradictions between the model and the observed data, while maintaining the possibility of higher-order interactions.

In another embodiment, an artificial intelligence model, such as an unsupervised model, may be trained on patient health information or other therapy information. The unsupervised model may be trained on information comprising information about the medications or other therapies the patient received and progression, or treatment interval superseding, events. In some examples, the progression events of relevance to the model training are progression events that occurred after a first therapy was discontinued and before a second therapy was initiated.

In some embodiments, the line(s) of therapy identified by the trained model using the health data of a patient are in accordance with pre-determined clinical practice guidelines, such as the guidelines published by the National Comprehensive Cancer Network (NCCN), FDA guidelines, clinical trials, or other publications.

In some embodiments, a semi-supervised approach may be implemented where a number of lines of therapies are curated from NCCN guidelines, FDA recommendations, clinical trials, pharmaceutical fact sheets, or other publications and then used as a starting point to identify labels in patients where labels not matching the curated labels are generated during the unsupervised portion of the semi-supervised approach. One of ordinary skill in the art would recognize that semi-supervised approaches take additional time during operation to set up and run but provide more reliable LoT because they are given a starting basis that contains accurate LoT designations.

In some embodiments, treatments can be generated by generating consolidated treatments from treatments having the same treatment identifier when the administration dates of the two or more treatments are within a time period of one another. In some embodiments, the time period can be based at least in part on the disease state. In some embodiments, the time period can be based at least in part on the treatment identifier. In some embodiments, the time period can be based at least in part on the disease state and the treatment identifier.

For any particular patient record, the lines of therapy identified from the record may align with those published in the clinical practice guidelines. For instance, in ovarian cancer, clinical practice guidelines may recommend niraparib as maintenance therapy for patients with platinum-sensitive disease who have had 2 or more lines of platinum-based therapy and a complete or partial response to the most recent line of recurrence therapy. Analytics, such as those performed via web pages 160A-N or GUI 170 may provide compliance statistics for physicians or institutions with the guidelines from NCCN, FDA, or other guideline setting entities.

Some of the lines of therapy match clinical practice guidelines, such as those identified in NCCN guidelines. Other of the lines of therapy may not match to clinical practice guidelines. In these instances, the LoT determination may be used for quality improvement purposes to identify data in the medical record that may be incorrect. In other instances, the LoT determination may identify a patient who participated in a clinical trial, such as a trial testing a combination of FDA-approved therapies. In other examples, the LoT determination may identify a new trend in clinical practice not yet reflected in current clinical practice guidelines. For example, a line of therapy in ovarian cancer of patients receiving a LoT chemotherapy regime followed by a LoT maintenance targeted therapy (such as a targeted inhibitor, like a PARP inhibitor or an EGFR inhibitor).

Another semi-supervised approach may force bucketing for timelines of LoT. For example, in 1980, a first LoT having two drugs may be standard, however, in 1993 those two drugs are discontinued as a LoT and replaced. A semi-supervised approach may ingest guideline changes from public records or identify years that new treatments are released based on inclusion in clinical trials and bound unsupervised LoT curation to be between years of LoT change so that the evolution of LoTs are tracked over the years. In one embodiment, those bounds may be set as a sliding window and determined automatically based upon an optimized EM similar to EM as shown in more detail with respect to FIG. 7. Similar bucketing may be performed on a geographic basis such as by physician, institution, state, region, country, or other common characteristics to a cohort of patients. Unsupervised learning excel in these analytics due to the inherently variable natures of attempting to identify new windows based on time or location to pull meaningful LoTs from the existing patient records. Analytics may be performed using the windowing to identify regions, institutions, or years where particular LoT are most effective.

In some embodiments, an unsupervised approach allows for fine tuning the system according to different cancers and their medications. For example, treatments for prostate cancer include oral medications which are taken for a longer interval than, for example, intravenous medications administered to treat lung cancer which traditionally have short intervals. A restrictive structured model may have difficulty learning labels because the nuances of the cancer subtypes and labels may be restricted to only the categories of medications as enumerated by a programmer during training or available from the system of curated data.

Figure 6:
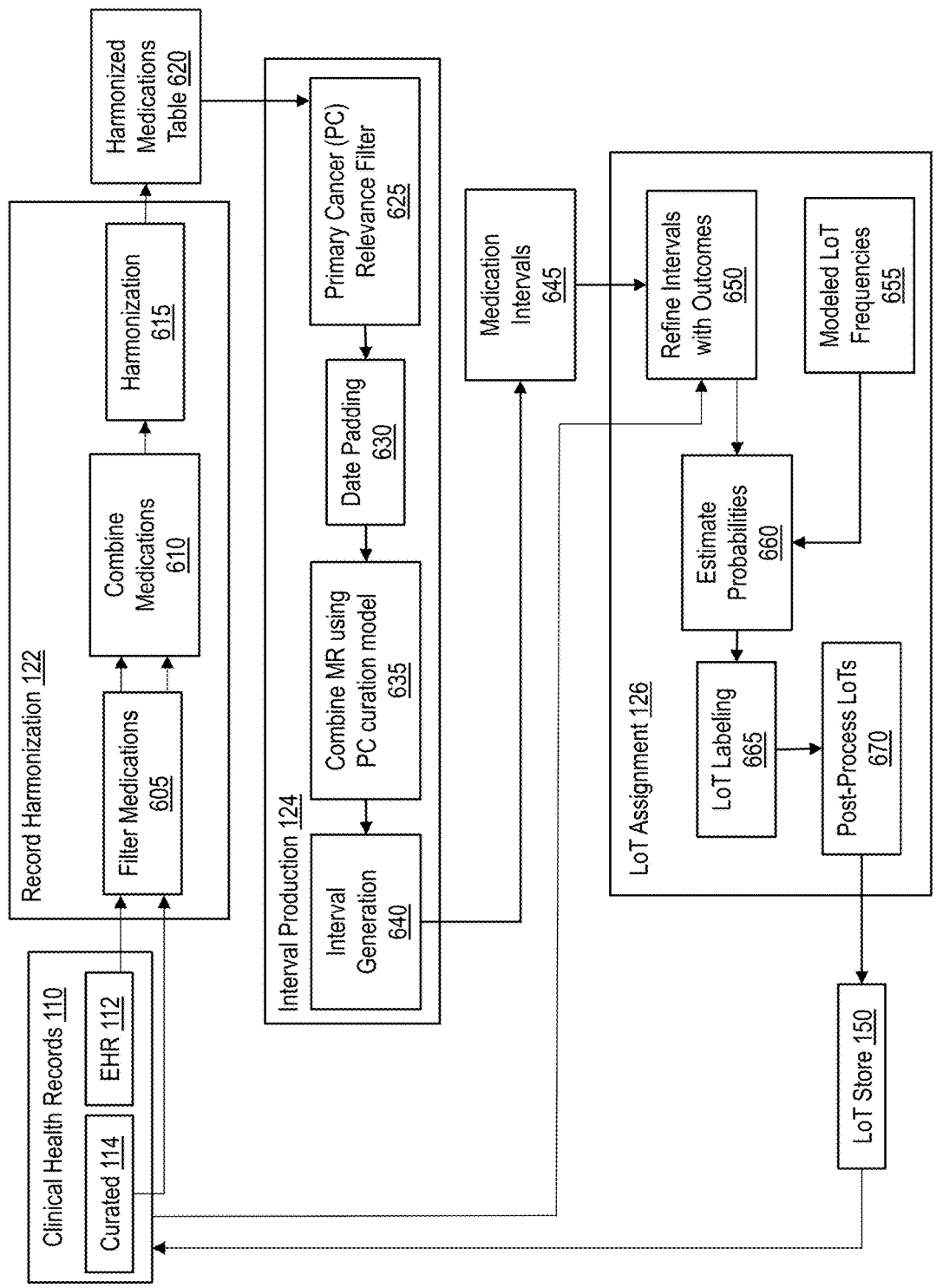
FIG. 6 is a flowchart depicting system 600 an embodiment of preparing, training, and assigning Line of Therapy (LoT) using an artificial intelligence engine approach with rule-based pre-processing for implementing a method that imputes complex, curated fields from curated patient histories and applies them to non-curated patients or patients with a paucity of data.

FIG. 6 is a flowchart depicting system 600 an embodiment of preparing, training, and assigning Line of Therapy (LoT) using an artificial intelligence engine approach with rule-based pre-processing for implementing a method that imputes complex, curated fields from curated patient histories and applies them to non-curated patients or patients with a paucity of data.

A patient's medication history is captured as clinical health records 110 through a combination of Curated Medical Records (MR) 114 derived from a combination of machine learning and medical expert annotation of digital documents such as progress notes and Electronic Healthcare Record (EHR) MRs 112. Features of a patient's medical records may be structured and sent to a plurality of modules within system 600. System 600 focuses upon taking this redundant, repetitive, and sometimes inconsistent raw input and converting it into a set of condensed records that capture the most salient medications used to treat a patient's cancer. The following steps are an exemplary method for performing this conversion.

In another embodiment, record harmonization 122 may include modules to filter medications 605, combine medications 610, and to harmonize medications 615. Filtering medications 605 may include filtering medications of the clinical health records 110 from the curated records 114 and the EHR 112 to medications cancer treatment, such as antineoplastic agents. Filters may also be applied for other medicinal characteristics such as to identify medications relevant to a line of therapy. Filtering medications which are not typically a part of a line of therapy reduces the computational load necessary to process the immense number of patient records available. For example, Electronic healthcare records (EHR) consist of all medications ordered and administered to the patient, varying between analgesics, antibiotics, placebos, to multivitamins. Filtering stage 605 removes any medication that has not been identified as a antineoplastic agent (anti-cancer) and stored in an internal value set. This value set may be defined by a clinical team or curated from machine learning models as well as internal and external publications, clinical trials, FDA approvals, NCCN guidelines, or pharmaceutical drug reports.

Combine medications 610 may combine Medication Records (MR) within a threshold number of days(d), such as 22 days. The threshold may be set by medication, drug class, active ingredient or learned from patient records via an artificial intelligence engine. EHR MR are highly repetitive, periodic records that occur with every order and administration of a medication. Numerous antineoplastic therapies are administered every 22d (referred to as one 'cycle'), so by combining records within 22d, a significant record compression may be achieved that captures the entire duration a patient is administered a medication. Procedurally, one process for date imputation may be performed for each record, including:

a) If the MR has a year-only start or end date, or missing start date, skip to Harmonization 615.

b) If the MR has a month-only start or end date, impute to 15<sup>th</sup> of month.
c) If the MR has a missing end date, set the end date to the start date.
Separately for native and curated records (that is, for all medications of the native record, perform the following steps as well as for all medication of the curated records), perform the following for each medication:
  i) Sort each MR of the medication by start date.
  ii) For each MR of the medication:
    (1) Compare the end of the record with the start of the subsequent record. If the MR are within 22d of each other, combine the records. This may be accomplished by setting the end of the record to the end of the subsequent record and deleting the intervening MR for that medication.
    (2) Continue to the next record.

Harmonization 615 may identify and correct for redundant and sometimes contradictory information. 'Harmonization' refers to the set of heuristics learned from machine learning algorithms, internal, and external publications and medical experts, to remove these redundancies or conflicts and establish a consistent set of MR combining the high temporal resolution of the EHR MR 112 and the expert knowledge in the Curated MR 114. Procedurally, one embodiment of harmonization may entail:
a) Impose the following imputation rules to cure the poor temporal resolution of some Curated EMR, and satisfying resolution of the MR to be precise within a day, week, or month as needed for harmonization. The below approach presumes the largest duration for these records, allowing EHR MR with possibly higher resolution to clarify these dates.
  i) If month-only start, set day to 1<sup>st</sup> of month. If year-only, set month to January and day to the 1<sup>st</sup>.
  ii) If month-only end, set day to 15<sup>th</sup> of month. If year-only, set month to December and day to the 31<sup>st</sup>
b) If all records are native or curated, no harmonization necessary, continue to interval production 124.
c) Sort the combined records by start date.
d) For each medication type in the patient record:
  i) Create an empty 'output list'. (last entry in list referred to as output[−1])
  ii) For each record in this medication type:
    (1) If this is the first entry, add to output.
    (2) If the current record occurs after output[−1], append record to output. Continue.
    (3) If the record has a higher-resolution start or end date than output[−1] (such as month or year resolution, and the record has day-resolution), replace the lower-resolution date with the higher resolution date.
    (4) If the record occurs within the timeframe of output[−1] (such as a single day record occurring within a several month-long curate record) exclude this extraneous record from output list.
e) Return the output list as harmonized medications table 620 having the medications of each MR categorized and structured.

In another embodiment, Interval Production 124 may comprise modules for primary cancer (PC) relevance filter 625, date padding 630, combining MR using a PC curation model 635, and interval generation 640. Lines of Therapy are best described by periods of continuous medical care describing the administration of one or more medications (such as, but not exclusively, 'regimens'). Here, these periods of continuous care are referred to as 'intervals,' or 'treatment intervals.' 'Intervals Production' is the process by which harmonized MR are converted to these treatment/medication intervals (MI). These simply represent durations of time a patient is taking one set of medications, with a new MI starting when any change, addition or subtraction, of an antineoplastic agent relevant to the patient's primary cancer type occurs.

PC relevance filter 625 may filter the harmonized medication table further by medications relevant to the patient's primary cancer (PC), diagnosis, or other identifier for basing a line of therapy. This list is defined by machine learning models, internal and external publications, and medical experts. This removes medications such as denosumab, which are supportive care in some cancers (such as prostate cancer), but considered salient to others (such as bone cancers). One embodiment of PC filtering may entail:
a) Filter patient MR using the PC relevance filter
b) Filter patients with significant uncertainty in the remaining MR, including:
  i) Year-only medication records.
  ii) Vague or general medication names present from curated progression notes (such as 'platinum compounds' or 'antineoplastic agents') rather than the actual medication name.

Date Padding 630 may identify and pad dates. Numerous MR consist solely of a start date, or an end date equivalent to the start date. In order to construct medication intervals, a minimum duration of time is required, so these records are given an end date using an interval-distinguishing threshold (DATE_PAD, typically 21d; DATE_PAD is a tunable hyper parameter that may be set by the user based upon the user's threshold selection). One embodiment may entail:
  A) If a record has no end date, or an end date=start date, set end date=start date+DATE_PAD.

Combine MR using PC Curation Model 635 may perform medication specific roll-ups. While numerous antineoplastic agents are administered roughly every 21d, some hormone treatments are administered monthly or less frequently. To account for this, a medication-specific rollup (typically 22d-180d) may be learned from a combination of machine learning and medical expert knowledge for each medication. This process is described below in more detail with respect to the PC Curation Model section. One embodiment may entail:
a) The learned medication-specific rollup is applied to each medication record. For each medication and each record:
  i) If the end of the previous record and the start of the subsequent record is within this rollup, combine the record, stitch the two records together.

Interval generation 640 may include conversion from MR to medication intervals. A patient's medication history typically consists of several antineoplastic agent MR that are temporally overlapping. This conversion process produces defined intervals of homogenous treatment of one or more medications, with a new medication interval started whenever an antineoplastic agent is added or subtracted from the patient's medication record. One embodiment may entail:
a) Sort resultant medication records by start date, and perform the following for each record:
  i) If one of the following is the case, create a new interval:
    (1) First medication record,
    (2) Medication record starts after the end of the last interval, or (3) The medication record starts within an interval-distinguishing threshold (e.g., 22 days) of the end of the last interval end and either the start of the record or the end of the previous interval are month-resolution.
ii) If the medication record overlaps with the last interval, add this medication record to the interval.
iii) If an interval of at least the interval-distinguishing threshold cannot be constructed due to several overlapping records, LoT cannot be determined for the patient, and return a failure state.
iv) Otherwise the medication record occurs across multiple other intervals, so add this medication to any overlapping records. If the record continues after the end of the last interval, create a new interval for the remaining of the record
b) Output the medication intervals 645, describing all records comprising the treatment interval, the start and end, and associated medications.

It should be understood to one of ordinary skill in the art that the steps above represent embodiments from which the present disclosure may operate. Other systems and methods consistent with the disclosure herein are also available.

Line of Therapy (LoT) Assignment 126 may comprise one or more modules refine intervals with outcomes 650, modeled LoT frequencies 655, estimate probabilities 660, LoT labeling 665, or post process LoTs 670. A patient's lines of therapy captures the treatment strategy employed by the oncologist to manage that person's cancer. Each line is one or more planned antineoplastic medications, and when an interval superseding event occurs to the patient (e.g., an imaging result indicating a worsening prognosis for a patient or a metastatic event), a new set of medications or new 'line of therapy' is proposed. Due to incomplete response data (often solely present in progress reports), these unplanned events are often missing in patient MR. The primary goal is to learn common treatment patterns and apply these when response data is scarce, producing a computationally-derived LoT assignment. Here, the intervals produced from LoT assignment 126 are annotated with response data from the patient's clinical health records 110, when present, producing a refined intervals list. Using the composition of integer (COI) approach, the most likely combination of these interval sets is determined and considered that patient's incrementally numerated LoTs. In some embodiments, one or more LoTs can be annotated. In some embodiments, the one or more LoTs may not be annotated. In some embodiments, the treatments can be annotated. In some embodiments, the treatments may not be annotated.

Refine Intervals with Outcomes 650 may identify certain "treatment interval superseding events" or patient events, such as outcomes, that are absolute indicators of a change in LoT. These are added to the medication intervals to produce a refined interval list consisting of one or more segmented sets of intervals. One such process for completing may include:
a) Gather all patient outcomes and filter to outcomes and interventions relevant to LoT. These can be cancer type specific, such as castration-resistant prostate cancer (CRPC) diagnoses or general like metastatic diagnosis or progressive disease outcomes. Outcomes commonly removed include complete and partial responses (indicating that the LoT is successful, and should be continued).
b) Iterate through each outcome and patient interval, and if an outcome occurs within the interval-distinguishing threshold of the start of a new interval, separate this patient interval list into two separate sets of intervals. If an outcome is within the threshold of two intervals, separate at the temporally closer interval, ties choosing the latter.
c) Iterate through the patient refined intervals list and break into additional sets if a line of therapy maximum duration threshold (e.g., 180 days) separation occurs.

Modeled LoT Frequencies 655 may enumerate composition of integer breakdowns for each treatment interval or generate every sequential permutation of medications which break down into potential lines of therapy. In one example, this may include an artificial intelligence engine trained on patient records.

Estimate probabilities 660 may receive the potential LoTs and the collection of treatment intervals for generating respective likelihoods for each LoT. Im some embodiments, 655 and 660 may be combined into a single stage such that an artificial intelligence engine receives refined intervals based on outcomes data and separates potential LoTs from the intervals as well as generates probabilities measuring a likelihood of each potential LoT is a LoT. In one example, a process may include:
a) After separating the refined interval list into set given outcomes, iterate through each set and perform the following (setting LoT counter=1):
i) Compute all possible compositions of the intervals (potential LoTs) using the composition of integers approach or an unsupervised artificial intelligence engine trained to identify LoTs from patient data.
ii) Calculate the probability of each of these interval compositions using the frequencies learned during model training. The total probability of a given interval combination is the product of the individual combined intervals (In the 2 interval case, this is Prob(interval 1)*Prob(interval 2) and the Prob(interval 1 followed by interval 2)).
iii) Consider the interval combination with the highest probability as the LoT assignment. (If Prob(interval 1)*Prob(interval 2)>Prob(Interval 1 followed by Interval 2), then Interval 1 would be the first LoT, and Interval 2 is the second)

LoT labeling 665 may identify the most likely composition of sets of medication intervals (potential LoTs with highest likelihood for each consecutive time period) may be considered a patient's LoT. In one example, a process may include:
i) Number each of these interval combinations with the LoT counter, incrementing each time. (If the 2 interval case was preceded by an interval which was assigned LoT 1, interval 1 would be assigned LoT 2, and interval 2 LoT 3).

Post-Process LoTs 670 may include identifying LoTs which may be corrected or modified. For example, in rare cases, consecutive combined intervals may have the same set of medications but were separated by a time period exceeding the combining thresholds for medications or intervals, but do not have any treatment interval superseding events and are therefore considered to be the same LoT. Any LoTs falling into a pattern which may be corrected or adjusted in post processing may be assigned to the same LoT and any following LoTs may be incrementally adjusted. In one example, this may include:
a) Combine all the most likely interval compositions into a final LoT list.
b) Iterate through each of the interval compositions, performing the following:

i) If two consecutive LoTs have the same medications, assign them the same LoT (Example: [doxorubicin, cyclophosphamide and doxorubicin]|[cyclophosphamide and doxorubicin, cyclophosphamide and doxorubicin and paclitaxel, anastrozole] produces the final output list [doxorubicin, cyclophosphamide and doxorubicin, cyclophosphamide and doxorubicin, cyclophosphamide and doxorubicin and paclitaxel, anastrozole], which is converted to [doxorubicin, cyclophosphamide and doxorubicin, cyclophosphamide and doxorubicin and paclitaxel, anastrozole], where "|" bars indicate an outcome, ",", commas denote new LoTs, and medications grouped with "and" are in combination).

In some embodiments, an Output LoT Table such as the LoT table stored in LoT Store 150, may be in a structured format, such as a json file, xml file, or other format and have a subset of the following structured data fields:

patient_id: The unique patient_id across tables.
interval_start: The start of the medication interval.
interval_end: The end of the medication interval.
medication: The associated medication (maximum one per row).
lot: The assigned LoT. (1-n, whole number).
complete_lot_start: The start of the overarching LoT, spanning one or more intervals.
complete_lot_end: The end of the overarching LoT, spanning one or more intervals.
complete_lot_medications: Listing associated medications in a given LoT, concatenated together with a "+" sign.
emr_derived: 1 if the entire LoT comes from medication records only present in EHR, and 0 otherwise.
success: whether LoT could successfully be defined for a patient. This is unsuccessful if the patient has year-only medications necessary for LoT or has a medication record that results in a treatment interval.

Once generated, LoT tables may be stored in LoT store 150 or combined with structured data of the patient's EHR for subsequent use in analytical models.

Primary Cancer (PC) Curation Model Algorithm

As described above, different medications have different cycles which can vary by primary cancer type. The following steps may be used to estimate this cycle time for a primary cancer type for a specific medication of interest by leveraging the medical knowledge present in Curated MR. By capturing the typical duration of a medication administration as described by Curated MR, and using this to propose a cycle time for that medication that when applied to EHR MR, recapitulates this typical duration. This has the effect of converting highly repetitive EHR administration records to the "appearance" of Curated MR durations that an abstractor may curate. Without loss of generality, this process is described for a single medication for a single primary cancer type below but may be extended to a plurality of cancer types and a plurality of medications without detracting from the present disclosure.

1. Input: Curated MR and EHR MR for a given medication, for a given primary cancer type.
2. Filter to Curated MR with the following properties:
    a. End dates distinct from the start dates
    b. Start and end dates with at least month resolution.
3. Calculate the duration of medication administration across these Curated MR, defined as the MR end date–MR start date.
4. Calculate the median duration of medication administration across these Curated MR.
5. Starting with a minimum interval threshold (typically 22d) perform the following:
    a. Combine EHR records within this threshold for each patient, (possibly) producing durations of medication administration described by one or more records.
    b. Calculate the duration of medication administration (end–start) for each of these records.
    c. Calculate the median duration across all of these records.
    d. IF this median is equal to the curated MR median (calculated in 4), return this interval threshold as the 'cycle time', but if it does not, then increment the interval threshold.
    e. IF the increment threshold is greater than the maximum interval threshold (typically set to 180d), break out of the loop.

The above approach may be generalized as calculating a kernel density approximation of the curated duration distribution, rather than the median, and returning the threshold that minimizes a distance metric (Euclidean, geometric, or the Kullback-Leibler divergence) of the two distributions.

Figure 7:
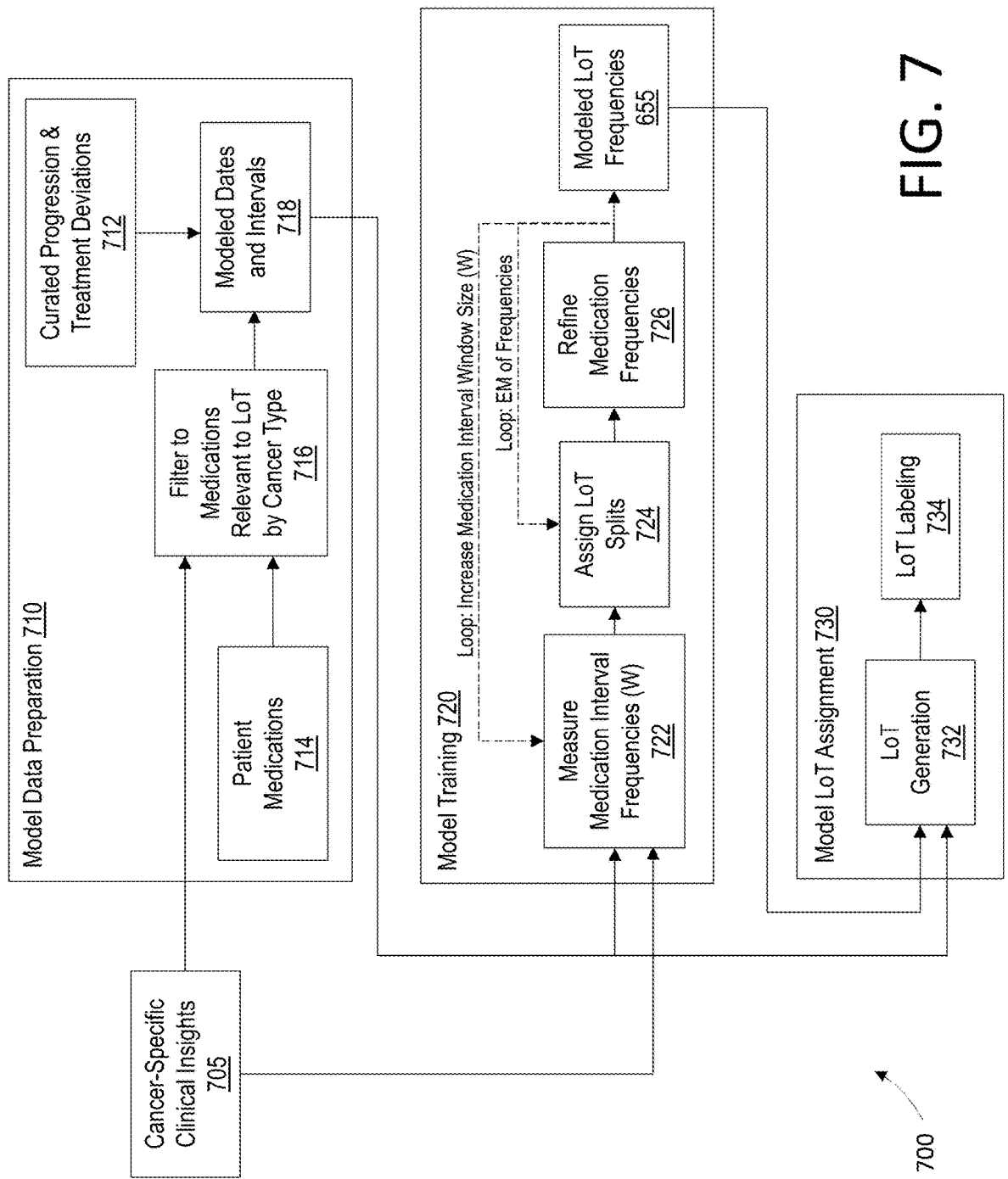
FIG. 7 is a flowchart depicting an embodiment of preparing, training, and generating Line of Therapy (LoT) models across three stages.

FIG. 7 is a flowchart depicting an embodiment of preparing, training, and generating Line of Therapy (LoT) models across three stages 710, 720, and 730.

At the model data preparation stage 710, sources of patient information relating to diagnosis, prognosis, treatment, and outcomes are aggregated across sources at clinical health records 110 containing curated and EMR/EHR records. Analytics from these records generate cancer-specific clinical insights 705, patient medications 714, and curated progression and treatment deviations 712. For example, if a patient is diagnosed with prostate cancer, prostate cancer clinical insights (such as types of medications, treatments, or therapies directly linked to treating prostate cancer, effects of particular medications, treatments, or therapies on prostate cancer, list of medication, treatments, or therapy names linked to codes relevant to LoT in prostate cancer, progression events that may establish a LoT break for each cancer type such as progress to castration-resistant prostate cancer (CRPC) diagnosis) may be retrieved at elements 705 and 712 from internal or external sources such as one or more databases or publications. The medications which have been curated from documents such as progress notes, lab results, or other handwritten documents may then be filtered to include only medications which are relevant to the diagnosed cancer for further processing such as medications which have an effect on treatment. For example, extraneous medications, such as amphetamine for headaches, antihistamines for allergies, seratonin receptor inhibitors for depression, or medications which are taken by the patient for purposes other than the treatment of the diagnosed cancer may be filtered from LoT prediction. Filtering to medications relevant to the LoT by cancer type at module 716 may be performed to filter out depression medications from cancer diagnosis so that the modeled dates and intervals 718 are calculated only from relevant to diagnosis treatments for each patient. Modeled dates and intervals 718 may include a corresponding start and end date may be generated on each of the medications remaining in the filtered LoT medication list and an initial timeline interval may be generated. A collection of modeled dates and intervals 718 are curated for all patients in a dataset having related diagnosis, for example all cancers, organ specific cancers (breast, lung, bone, blood, liver, prostate, etc.), or even a particular diagnosis such as non-small cell lung cancer, Ductal Carcinoma In Situ (DCIS), Invasive Ductal Carcinoma (IDC), Triple Negative Breast Cancer, or other diagnosis.

At the Training Stage 720, additional cancer-specific clinical insights are retrieved at element 705 and the medication intervals calculated at element 718 from stage 710 are received at measure medication interval frequencies (w) 722. Additional cancer-specific clinical insights may include the number of days that constitute an automatic LoT break (for example, for cancers which progress quickly this could be 90 days, and for cancers which progress at a slower pace, this could be 180 days, as well as progression events that may establish a LoT break for each cancer type such as CRPC diagnosis for prostate cancer). At element 722, treatment/medication intervals may be compared across all patient data to identify frequencies of occurrence. For example, in patients who have prostate cancer treatment/medication intervals may also be refined according to a rolling window with a width corresponding to a number of days (w). This process may be performed across one or more window sizes (w=30 days, 90 days, 120 days, etc) to identify the most representative set of LoTs in the patient population. For each medication interval identified in the patient population, an expectation maximization (EM) may be calculated to identify the reliability of the interval. These intervals may be assigned at assign LoT splits 724 after looping through the EM of frequencies. Once the optimal window size has been determined, the medication frequencies may be refined at refine medication frequencies 726. Refining may include looping through EM of frequencies once more until convergence at the designated window size (w) is accomplished. The set of treatment intervals which have the highest expectation values may be selected as the best representative set of LoTs (potential LoTs). After all patients have been processed to identify a base set of LoT, Stage 130 may output the estimated LoT frequencies from modeled LoT frequencies 655.

At model LoT assignment Stage 730, the collection of estimated LoT Frequencies across all patients 655 may be compared to the medication intervals of each new patient. At LoT generation stage 732, treatment intervals designated as potential LoTs may then be assigned to LoT splits, such as a first, second, third, and so forth LoT corresponding to each patient's ranking of potential LoTs. Each potential LoT assignment 732, enumerated according to the composition of an integer method may be ranked by the corresponding popularity of the LoT and the most probably LoT labeled as the patient's LoT at LoT labeling 734.

Exemplary applications of LoT labeling are discussed below with respect to FIGS. 8-13. Exemplary embodiments may be generated and labeled according to any of the methods and systems disclosed herein, including the systems and methods of FIGS. 1-7. The following examples are provided to illustrate how the differing methods and approaches herein may be applied to different examples of patient records.

Figure 8:
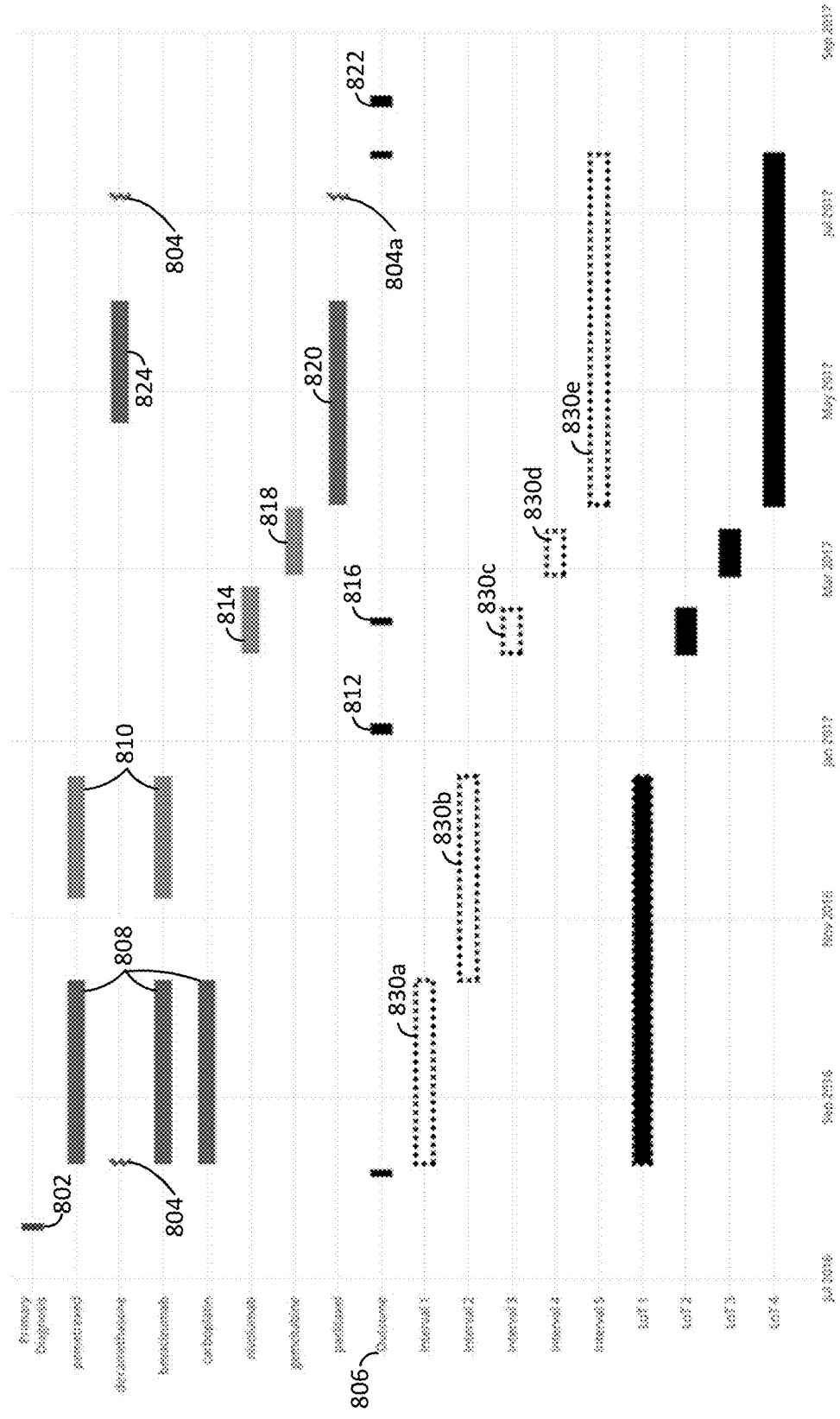
FIG. 8 is an illustration of a LoT prediction for a first patient diagnosed with metastatic non-small cell lung cancer.
Figure 9:
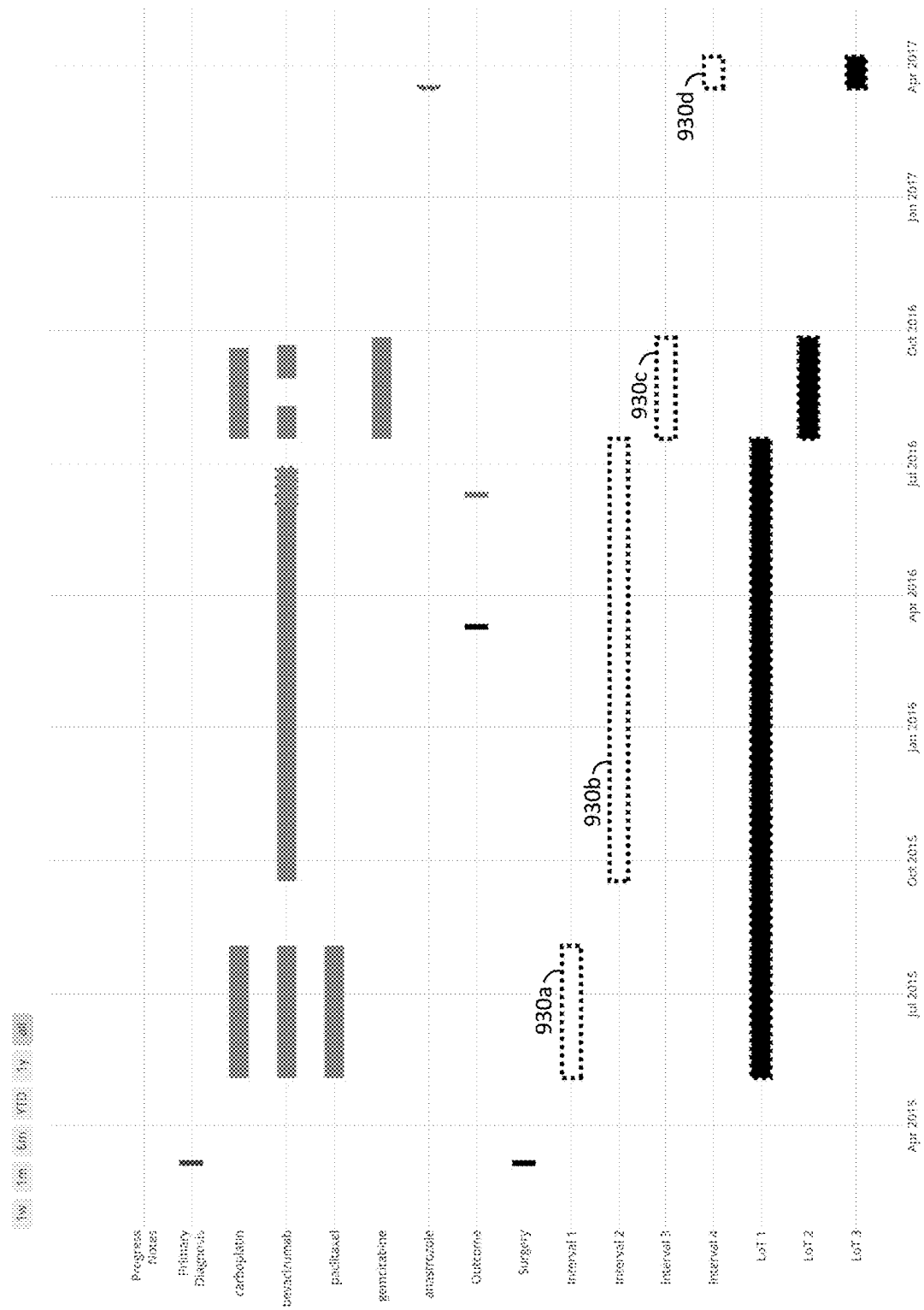
FIG. 9 is an illustration of a LoT prediction for a second patient diagnosed with ovarian cancer.
Figure 10:
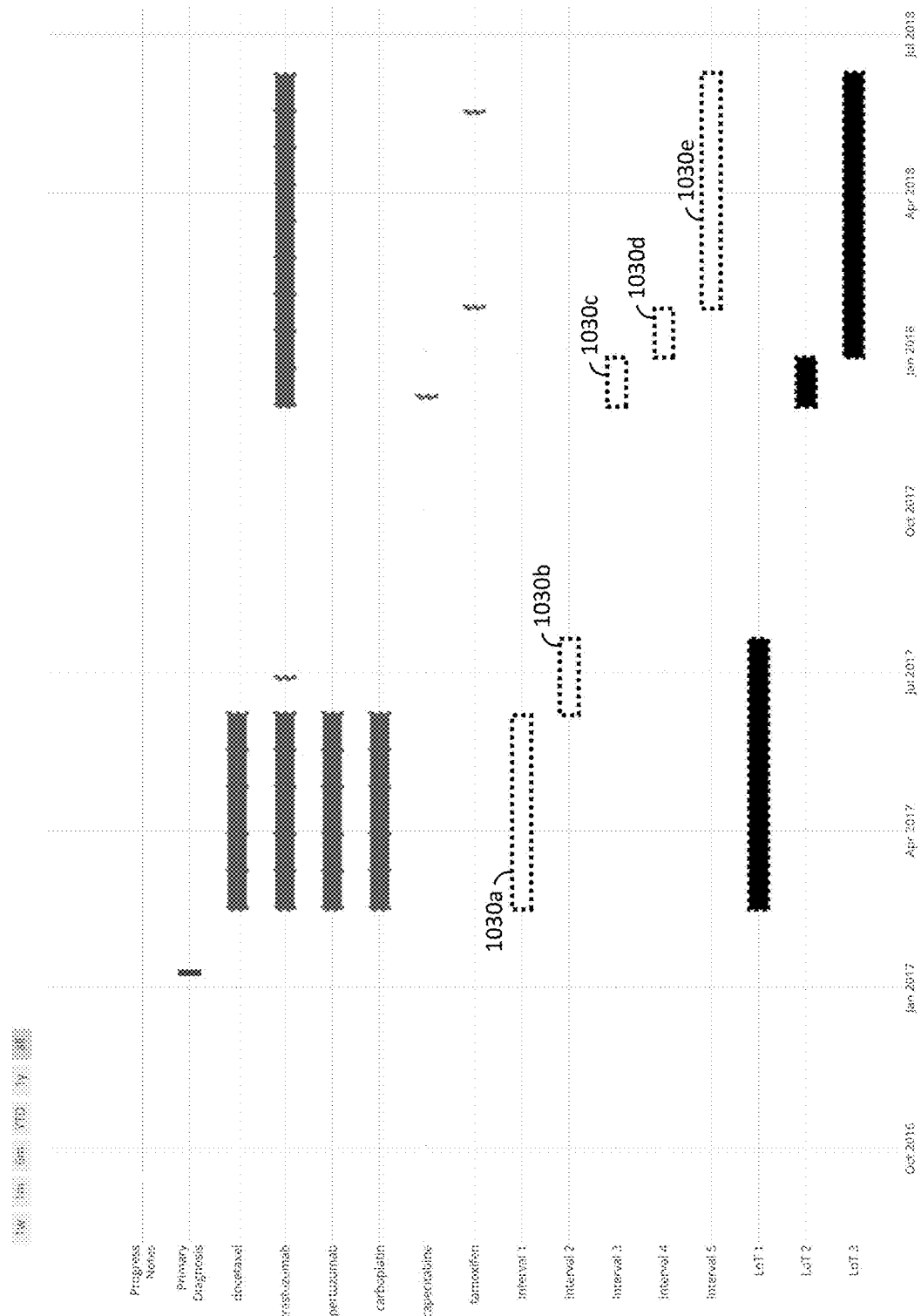
FIG. 10 is an illustration of a LoT prediction for a third patient diagnosed with breast cancer.

FIGS. 8-10 are illustrations depicting patient medical records, calculated medication intervals, and predicted Line of Therapies (LoT) from a combined EMR and Curated record system according to an embodiment. The type and source of patient records may be considered when extracting medications, outcomes, treatment interval superseding events, and other LoT features. These illustrations will highlight interactions between the EMR and Curated records to identify one or more therapy intervals and potential LoT in the record.

FIG. 8 is an illustration of a LoT prediction for a first patient diagnosed with metastatic non-small cell lung cancer. The first patient was diagnosed with NSCLC in August of 2016 at a primary diagnosis 802. Throughout the next year in a course of treatment, an oncologist treating the first patient logged several progress notes describing the patient, the first patient's medications, and associated outcomes (denoted as the "Progress Notes" above). This data is complemented by electronic medical healthcare records (EHR) of medication administrations 804.

A medical expert (curator) examined each of these progress notes and recorded the displayed medications and associated outcomes 806 from each note. The contents of the progress notes are now described.

Progress Note 1 (PN1): the curator recorded the patient's date of primary diagnosis as well as the first administration of the triplet chemotherapy of pemetrexed, bevacizumab, and carboplatin 808 in August of 2016.

PN2: The curator recorded the end of the triplet therapy 808 in PN1 in October 2016, a partial response to the associated therapy (not displayed, in October 2016), and the start of a pemetrexed/bevacizumab maintenance therapy 810 in November 2016.

PN3: In January 2017, the curator recorded a progressive disease outcome 812 to the pemetrexed/bevacizumab maintenance therapy 810 and its associated end in December 2016. The oncologist also noted their intent to place the patient on nivolumab 814 in February 2017.

PN4: The curator recorded a progressive disease outcome 816 to nivolumab 814 (implying the therapy was unsuccessful in treating the patient's cancer) in February 2017. The start of gemcitabine therapy 818 was also noted starting in March 2017.

PN5: The end of gemcitabine 818 was recorded due to toxicity in late March 2017, as well as the start of paclitaxel 820 administration at the same time.

PN6: The end of paclitaxel 820 was recorded in June 2017 and an associated 'complete response' to therapy (indicating the patient was found cancer-free).

PN7: During a follow-up visit in August 2017, another 'complete response' 822 was recorded, indicating the patient was continued to be found cancer-free. These curated medications were entered in the medications table and the outcomes in the outcomes SQL tables for downstream analysis.

Inclusion and Harmonization with EHR

The medication administration record present in the EHR from the hospital was next added to the medications data table (all medication administrations 804 and event bars according to the record harmonization 122 in FIG. 1). Dexamethasone administrations 824 were additionally logged. These medications were not curated, as this is a supportive care medication a patient commonly receives in tandem with chemotherapy to temper the side effects. While displayed, dexamethasone was filtered and not considered in subsequent calculations since supportive care medications are not considered salient to LoT Interval production module 124. The EHR administration records of pemetrexed, bevacizumab, and carboplatin 808 in September and October 2016 were added to the curated record of these medications, producing a 'native and curated' record for these medications in the record harmonization 122. The EHR administrations of paclitaxel 820 were used to augment the curated record from April-June of 2017, producing another 'native and curated' record. The additional administration of paclitaxel in August (at 804a) was added to the patient record in the record harmonization 122.

Delineation of Medication Intervals

The described medication records were next converted to intervals of unique medications (dotted bars denoted 830a-e). These intervals represent aggregations of medications taken simultaneously with a defined start and end date. A medication interval is created whenever a change in medication occurs (see Interval production module 124).

Interval 830a: The first medication interval starts with the triplet therapy pemetrexed/bevacizumab/carboplatin, ending with the discontinuation of carboplatin in October 2016 (Interval production module 124).

Interval 830b: Consisting of pemetrexed/bevacizumab, this interval started with the discontinuation of carboplatin, and continues until the end of this doublet therapy (Interval production module 124).

Interval 830c: This captures the patient administration of nivolumab in February 2017 (Interval production module 124).

Interval 830d: This interval starts with the administration of gemcitabine in March 2017, and ends with its discontinuation and start of paclitaxel (Interval production module 124).

Interval 830e: Starting with the curated and native paclitaxel record, this extends until the EHR record of paclitaxel administration in July 2017. Although the patient received dexamethasone starting in May 2017, since this medication is not considered relevant to LoT assignment, it does not cause a 6th interval from May 2017-July 2017 to be produced (Interval production module 124).

LoT Assignment on Intervals

Next, a combination of probabilistic choices and heuristics are applied to determine LoT on the produced medication intervals (1-5) (Lot Assignment module 126):

Outcomes are considered to separate out the different intervals. The outcomes in January 2017 are used to separate Interval 830b from Interval 830c (Lot Assignment module 126). The outcome in late February 2017 is used to separate Interval 830c and Interval 830d (Lot Assignment module 126).

We now consider Intervals 830a-b. In this case, a probabilistic choice is made considering the relative frequencies of each of these intervals across the training population. The probability of seeing Interval 830a (representing the triplet therapy) alone is 10%, the probability of seeing Interval 830b (pemetrexed/bevacizumab) alone is 5%, so the combined probability is 0.5% (10%*5%). However, seeing Interval 830a followed by Interval 830b is 2%. Since 2%>0.5%, this interval is combined and defined as 1 LoT (Lot Assignment module 126).

Since Interval 830c has been separated by Interval 830b and 830d by outcomes, this solo Interval becomes LoT 2 (Lot Assignment module 126).

Intervals 830d and 830e are now considered in terms of a probabilistic choice. The probability of seeing Interval 830d and 830e alone is 7.5% (30% and 25%, respectively; 30%*25%=7.5%), while the probability of seeing Interval 830d-830e across the dataset is 1%. Since 7.5%>1%, the intervals are considered separated LoTs, so Interval 830d is assigned to LoT 3, and Interval 830e is assigned LoT 4 (Lot Assignment module 126).

FIG. 9 is an illustration of a LoT prediction for a second patient diagnosed with ovarian cancer.

Patient Background and Clinical Data Sources.

PN1, March 2015: primary diagnosis and surgery, start of carboplatin, bevacizumab, and paclitaxel.

PN2, September 2015: start of bevacizumab, end of carboplatin, paclitaxel.

PN3, March 2016: progressive disease outcome

PN4, June 2016: progressive disease outcome, end of bevacizumab (month only), start of carboplatin, bevacizumab, and gemcitabine.

PN5, October 2016: end of carboplatin, bevacizumab, and gemcitabine.

EHR source: anastrozole, April 2017.

Intervals Construction

Interval 930a: triplet therapy carboplatin/bevacizumab/paclitaxel.

Interval 930b: beviczumab (separated from Interval 930a by Interval production module 124).

Interval 930c: carboplatin/bevacizumab/gemcitabine.

Interval 930d: anastrozole (separated from Interval 930a by Interval production module 124).

LoT Assignment:

The outcome in June 2016 is used to inform a separation between Intervals 930a-b and 930c-d (Lot Assignment module 126). Interval 930c and 930d are separated due to a separation between the end of the previous and the start of the next (Lot Assignment module 126). The refined interval list now consists of the following: [(Interval 930a, Interval 930b), (Interval 930c), (Interval 930d)].

For the first set, the probability of Interval 930a and Interval 930b alone versus combined is compared. The combined interval is more likely, so the set becomes (Interval 930a+Interval 930b), and is assigned LoT 1 (Lot Assignment module 126).

Interval 930c is assigned LoT 2, and Interval 930d assigned LoT 3 (Lot Assignment module 126, only one possible composition).

FIG. 10 is an illustration of a LoT prediction for a third patient diagnosed with breast cancer.

Patient Background and Clinical Data Sources.

PN1, January 2017: Primary diagnosis, Breast, and start of docetaxel, trastuzumab, pertuzumab, and carboplatin.

PN2, July 2017: End of docetaxel, trastuzumab, pertuzumab, and carboplatin. EMR, July 2017: Administration of trastuzumab EMR, December 2017-June 2018: Administration of capecitabine, several administrations of trastuzumab, and two administrations of tamoxifen.

Intervals Construction

Interval 1030a: Quadruplet therapy of docetaxel, trastuzumab, pertuzumab, and carboplatin.

Interval 1030b: Trastuzumab (separated by Interval 1030a via Interval production module 124).

Interval 1030c: Trastuzumab and capecitabine (separated from Interval 1030b by new medication and Interval production module 124).

Interval 1030d: Trastuzumab (separated from Interval 1030c by drop of capecitabine Interval production module 124 referencing the continued trastuzumab).

Interval 1030e: Trastuzumab and tamoxifen (separated from Interval 1030d by introduction of tamoxifen; Interval production module 124; continues via Interval production module 124, with tamoxifen employing a 207d medication-specific rollup).

LoT Assignment: since this record has no outcomes, all possible compositions of the 5 intervals are considered probabilistically (in this case, 2(5−1) or 16 possible combinations; Lot Assignment module 126), with the most probable chosen as the series of LoTs. In this case, 2+1+2 was chosen as the most likely interval composition.

FIGS. 11-13 illustrate line of therapy labeling from patient records according to another embodiment comprising four steps:

1) Combining medical records identifying medications, cancer diagnosis, and outcomes such as interval superseding events.
2) Defining a plurality of medication intervals at the start of each new therapy or medication in the patient records.
3) Applying an artificial intelligence engine trained in an unsupervised manner from a plurality of patient records to apply the learned heuristics on the complete listing of LoTs.
4) Outputting the LoT assignments according to the identified LoTs from the artificial intelligence engine.

FIGS. 11-13 comprise a listing of a primary diagnosis (pDX) at a time 0 days, a plurality of medications/therapies occurring after the primary diagnosis at a time and having a duration of at least one day, and any interval superseding events such as a surgery, or outcome listing from the patient records. Each having a pDX start date and end date for displaying the interval of the therapies, medications, or other events.

Figure 11A:
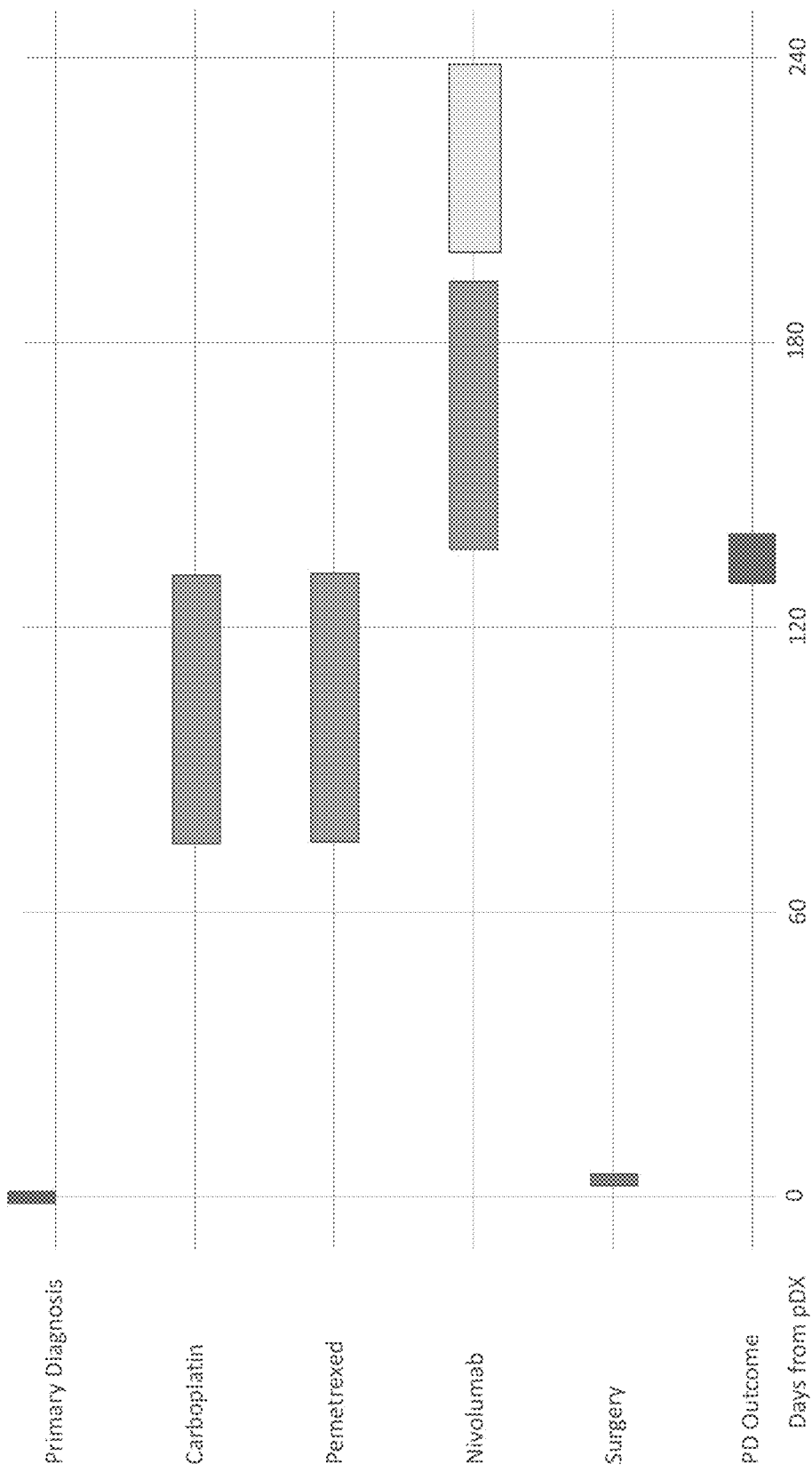
FIG. 11A illustrates a first step of a flow.

Referring now to FIGS. 11A-11D, an exemplary flow 1100 of line of therapy generation is shown. FIG. 11A illustrates a first step of the flow 1100. The first step of the flow 1100 can include combining one or more medications and/or treatments, one or more diagnoses (e.g., a cancer diagnosis), and one or more outcomes (e.g., a progressive disease outcome). In the example flow 1100, a primary diagnosis can define the start of a timeline that events and/or treatments can be mapped to in order to provide one or more time intervals to a user (e.g., an oncologist). As shown, the one or more medications and/or treatments can include Carboplatin, Pemetrexed, Nivolumab, and Surgery. In some embodiments, the flow 1100 as shown in FIG. 11A can be generated using steps 210 and 220 in FIG. 2.

Figure 11B:
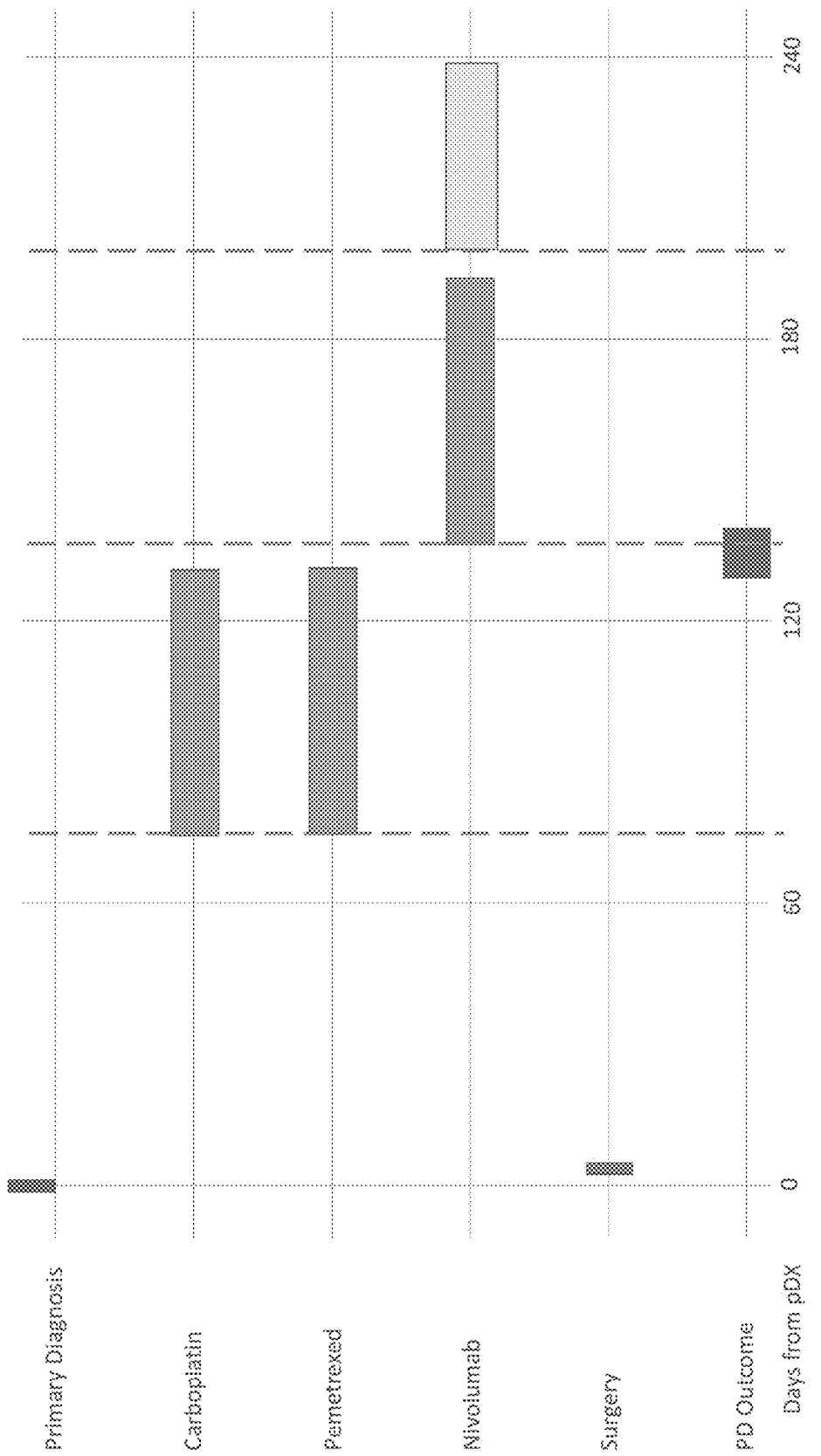
FIG. 11B illustrates a number of medication intervals included in a second step of the flow of FIG. 11A.

FIG. 11B illustrates a number of medication intervals included in a second step of the flow 1100. The flow 1100 in FIG. 11B can be generated based on the one or more medications and/or treatments in FIG. 11A. Certain medications can be associated with a common interval for one or more new treatments. As shown, Carboplatin and Pemetrexed can be associated with a first medication interval that is approximately 70 days after the primary diagnosis. The first medication interval can define the start of a first new treatment. Other medications can be associated with a second medication interval. As shown, Nivolumab can be associated with the second medication interval. The second medication interval can define the start of a second new treatment. In some embodiments, the flow 1100 as shown in FIG. 11B can be generated using step 230 in FIG. 2.

Figure 11C:
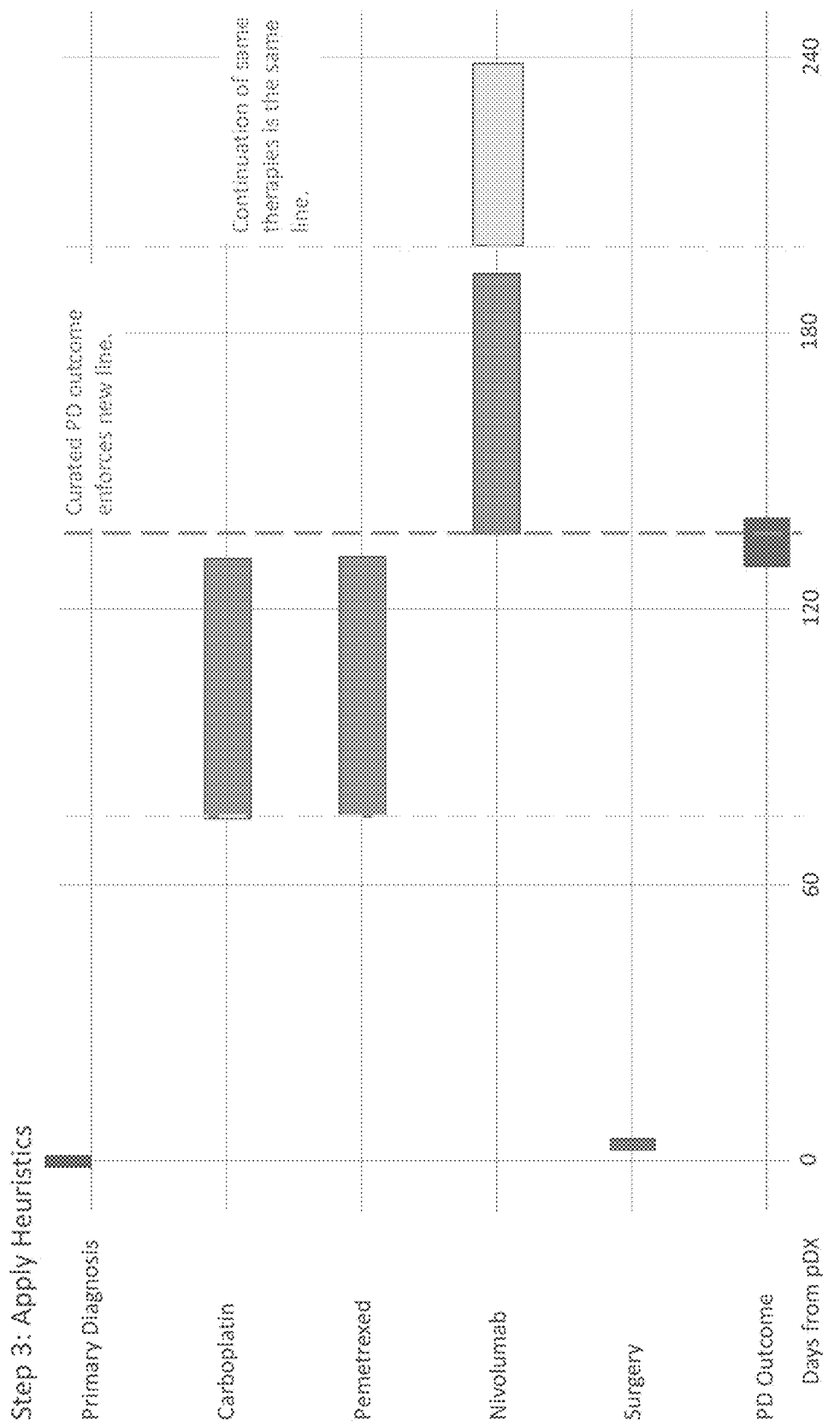
FIG. 11C illustrates applying heuristics to refine one or more medication intervals in a third step of the flow of FIG. 11A.

FIG. 11C illustrates applying heuristics to refine one or more medication intervals in a third step of the flow 1100. The heuristics can refine one or more medication intervals by combining overlapping intervals, splitting intervals up, or adjusting the start and/or end dates according to one or more heuristics, rules, or trained models. For example, Carboplatin and Pemetrexed could be associated with separate medication intervals, and the flow 1100 can associate both Carboplatin and Pemetrexed with the first medication interval. The heuristics can refine one or more medication intervals based on a rule associated with the progressive disease outcome. For example, the heuristics can set the second medication interval to start at about 130 days after diagnosis based on the progressive disease outcome at about 130 days after diagnosis. For continuation of the same medication (e.g., Nivolumab), the line of therapy can be the same for all medication intervals, such as a third interval associated with a second treatment using Nivolumab. In some embodiments, the flow 1100 as shown in FIG. 11C can be generated using step 240 in FIG. 2.

Figure 11D:
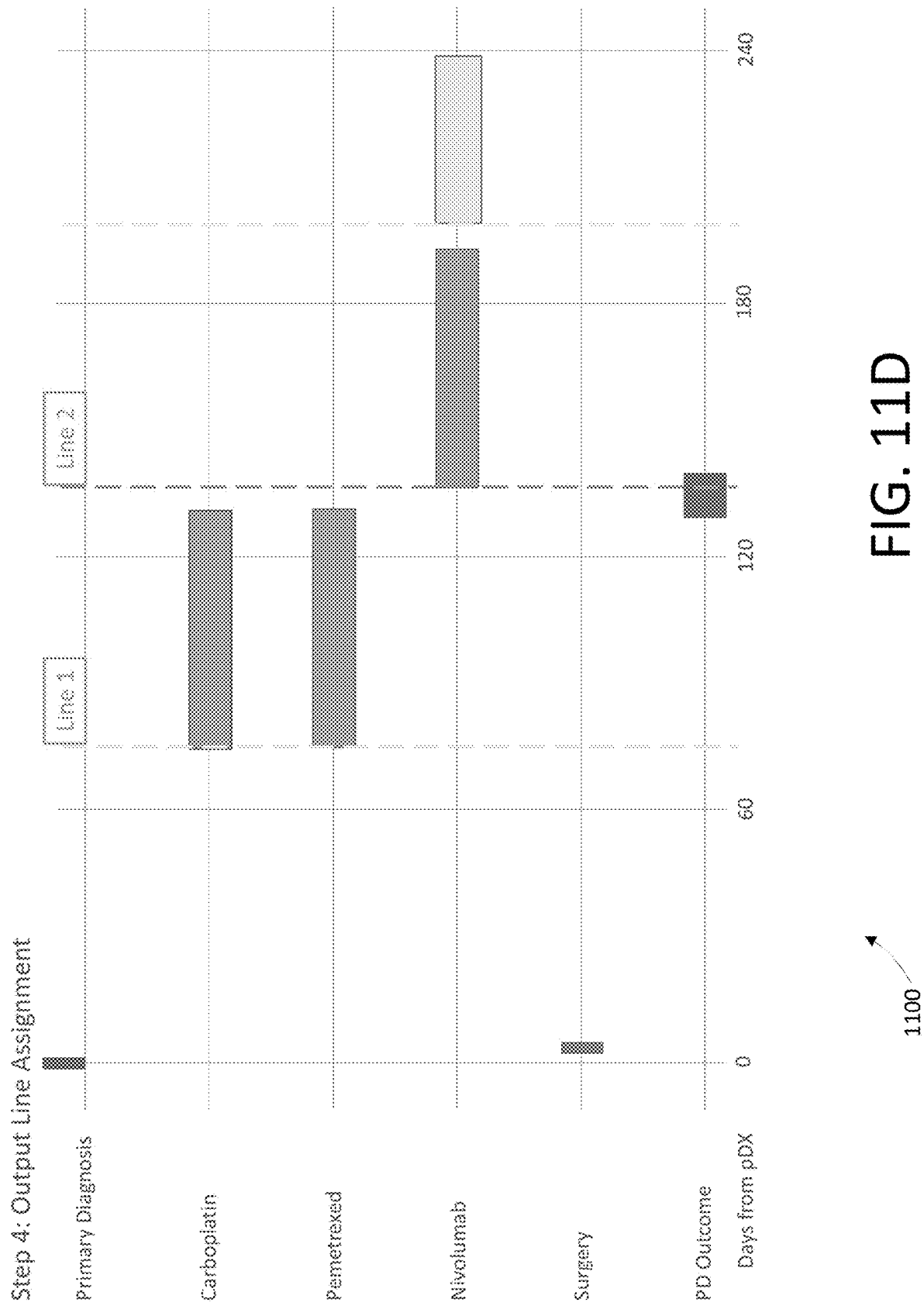
FIG. 11D illustrates outputting line assignments in a fourth step of the flow of FIG. 11A.

FIG. 11D illustrates outputting line assignments in a fourth step of the flow 1100. The line assignments can be associated with one or more potential lines of therapy from the one or more medication intervals. Identification may be performed using a trained model, an exhaustive enumeration with ranking based on likelihood, or other method as disclosed herein. The lines of therapy can include a first line associated with the first medication interval (e.g., Carboplatin and Pemetrexed treatments) and a second line associated with a second medication interval (e.g., Nivolumab treatment). In some embodiments, the flow 1100 as shown in FIG. 11D can be generated using steps 250 and 260 in FIG. 2.

Figure 12A:
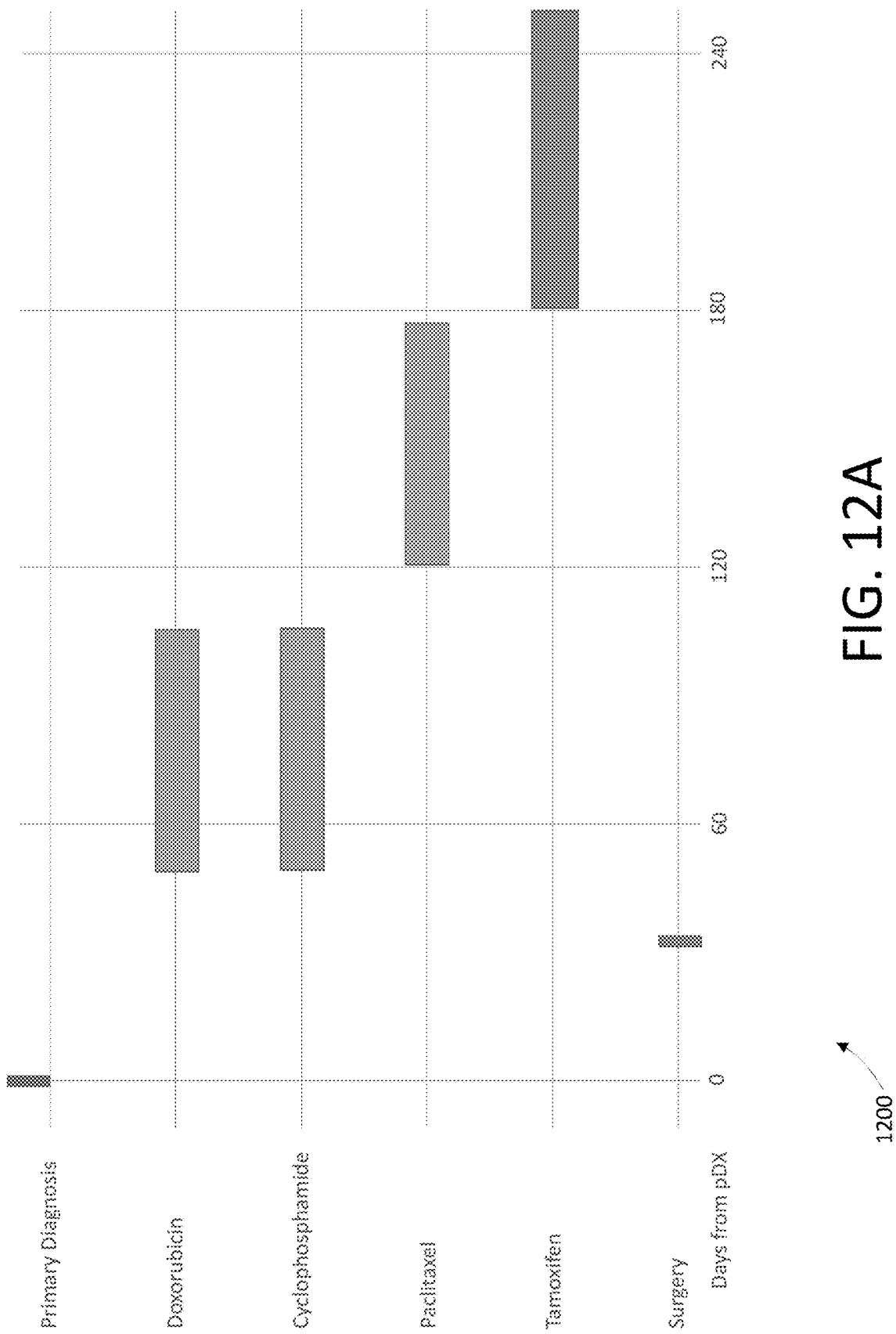
FIG. 12A illustrates a first step of a flow.

Referring now to FIGS. 12A-12F, an exemplary flow 1200 of line of therapy generation is shown. FIG. 12A illustrates a first step of the flow 1200. The first step of the flow 1200 can include combining one or more medications and/or treatments and one or more diagnoses (e.g., a cancer diagnosis). In the example flow 1200, a primary diagnosis can define the start of a timeline that events and/or treatments can be mapped to in order to provide one or more time intervals to a user (e.g., an oncologist). As shown, the one or more medications and/or treatments can include Doxorubicin, Cyclophosphamide, Paclitaxel, Tamofizen, and Surgery. In some embodiments, the flow 1200 as shown in FIG. 12A can be generated using steps 210 and 220 in FIG. 2.

Figure 12B:
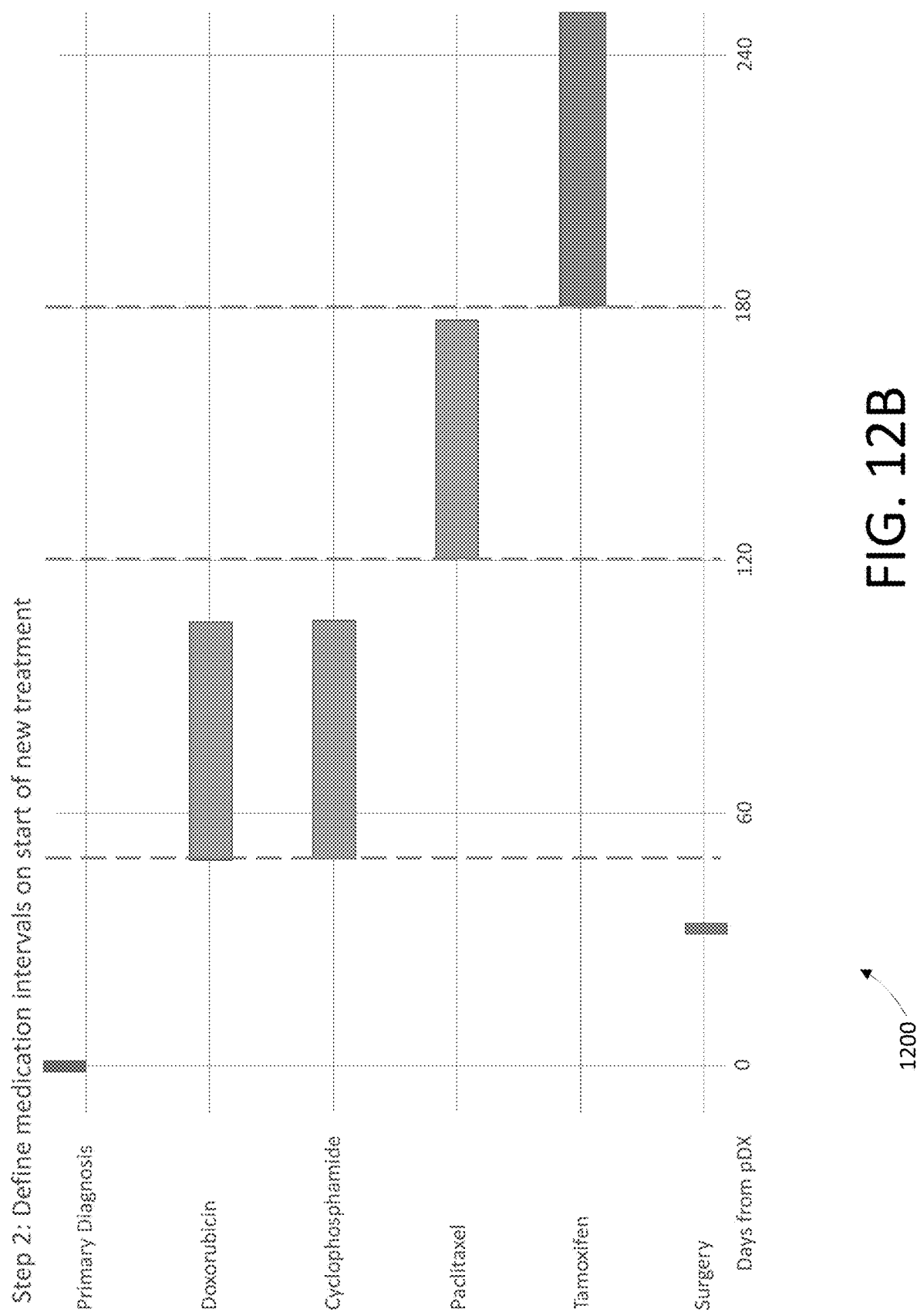
FIG. 12B illustrates a number of medication intervals included in a second step of the flow of FIG. 12A.

FIG. 12B illustrates a number of medication intervals included in a second step of the flow 1200. The flow 1200 in FIG. 12B can be generated based on the one or more medications and/or treatments in FIG. 12A. Certain medications can be associated with a common interval for one or more new treatments. As shown, Doxorubicin and Cyclophosphamide can be associated with a first medication interval that is approximately 50 days after the primary diagnosis. The first medication interval can define the start of a first new treatment. Other medications can be associated with a second medication interval or a third medication interval. As shown, Paclitaxel can be associated with the second medication interval that is approximately 120 days after the primary diagnosis. The second medication interval can define the start of a second new treatment. As shown, Tamofizen can be associated with the third medication interval that is approximately 150 days after the primary diagnosis. The third medication interval can define the start of a third new treatment. In some embodiments, the flow 1200 as shown in FIG. 12B can be generated using step 230 in FIG. 2.

Figure 12C:
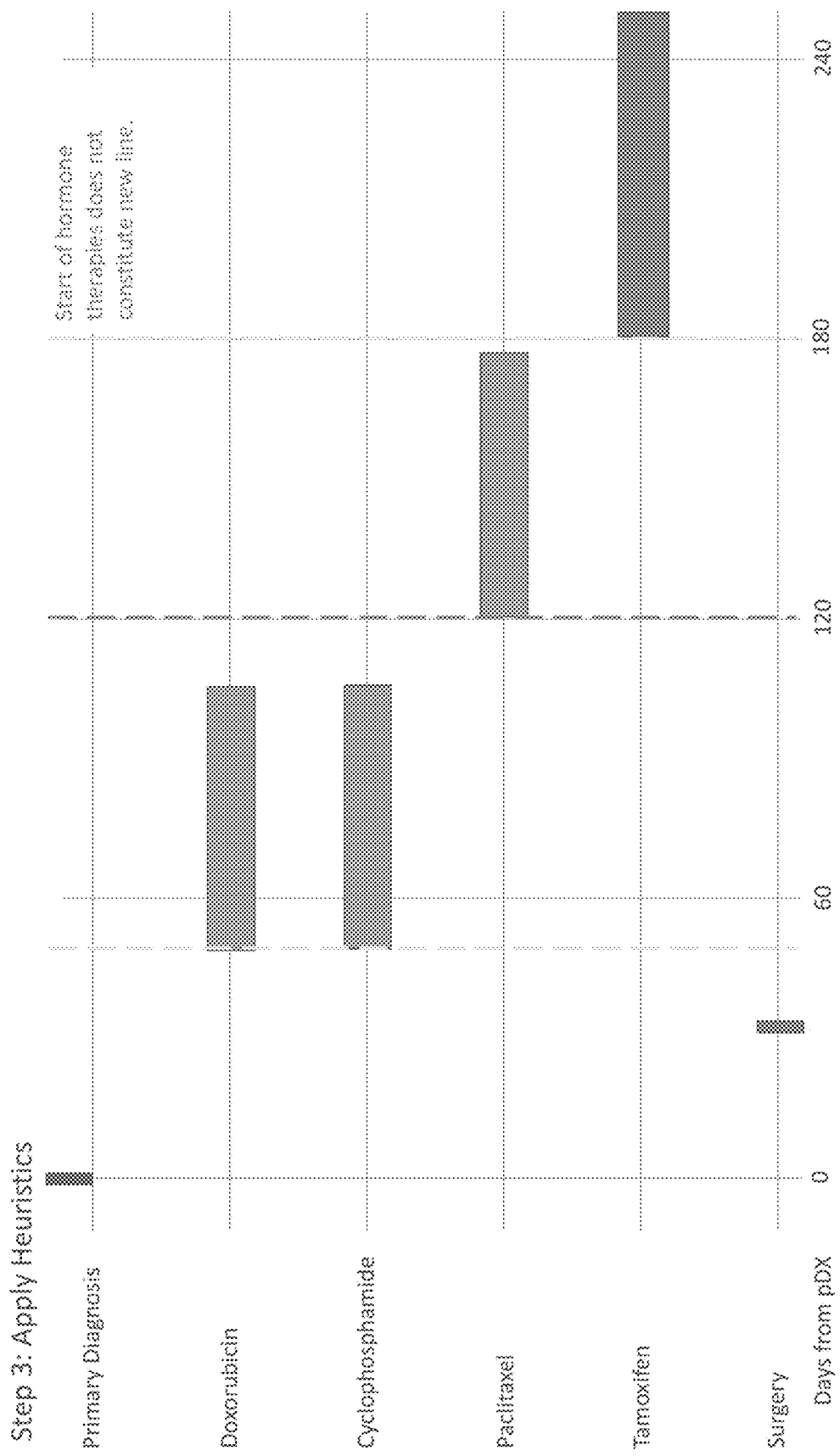
FIG. 12C illustrates applying heuristics to refine one or more medication intervals in a third step of the flow of FIG. 12A.

FIG. 12C illustrates applying heuristics to refine one or more medication intervals in a third step of the flow 1200. The heuristics can refine one or more medication intervals by combining overlapping intervals, splitting intervals up, or adjusting the start and/or end dates according to one or more heuristics, rules, or trained models. For example, Doxorubicin and Cyclophosphamide could be associated with separate medication intervals, and the flow 1200 can associate both Doxorubicin and Cyclophosphamide with the first medication interval. The heuristics can refine one or more medication intervals based on a rule associated hormone therapies. For example, the heuristics can set the second medication interval to to include the third treatment (e.g., Tamofizen) because the third treatment is a hormone therapy. In some embodiments, the flow 1200 as shown in FIG. 12C can be generated using step 240 in FIG. 2.

Figure 12D:
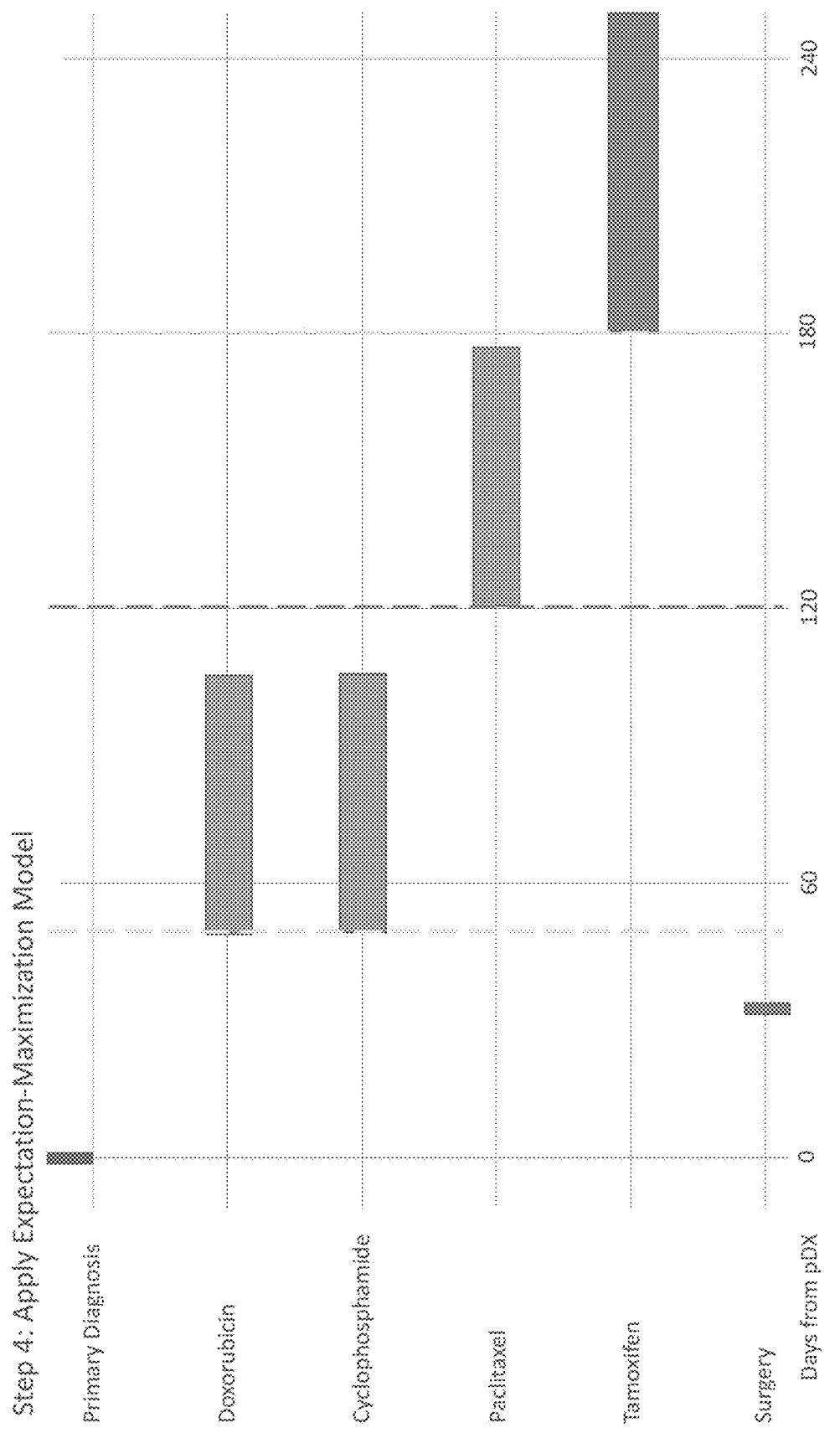
FIG. 12D illustrates applying an expectation maximization model to refine one or more medication intervals in a fourth step of the flow of FIG. 12A.

FIG. 12D illustrates applying an expectation maximization model to refine one or more medication intervals in a fourth step of the flow 1200. For each medication interval, the expectation maximization model can be used to calculate an EM to identify the reliability of the medication interval. In some embodiments, the flow 1200 as shown in FIG. 12D can be generated using step 240 in FIG. 2.

Figure 12E:
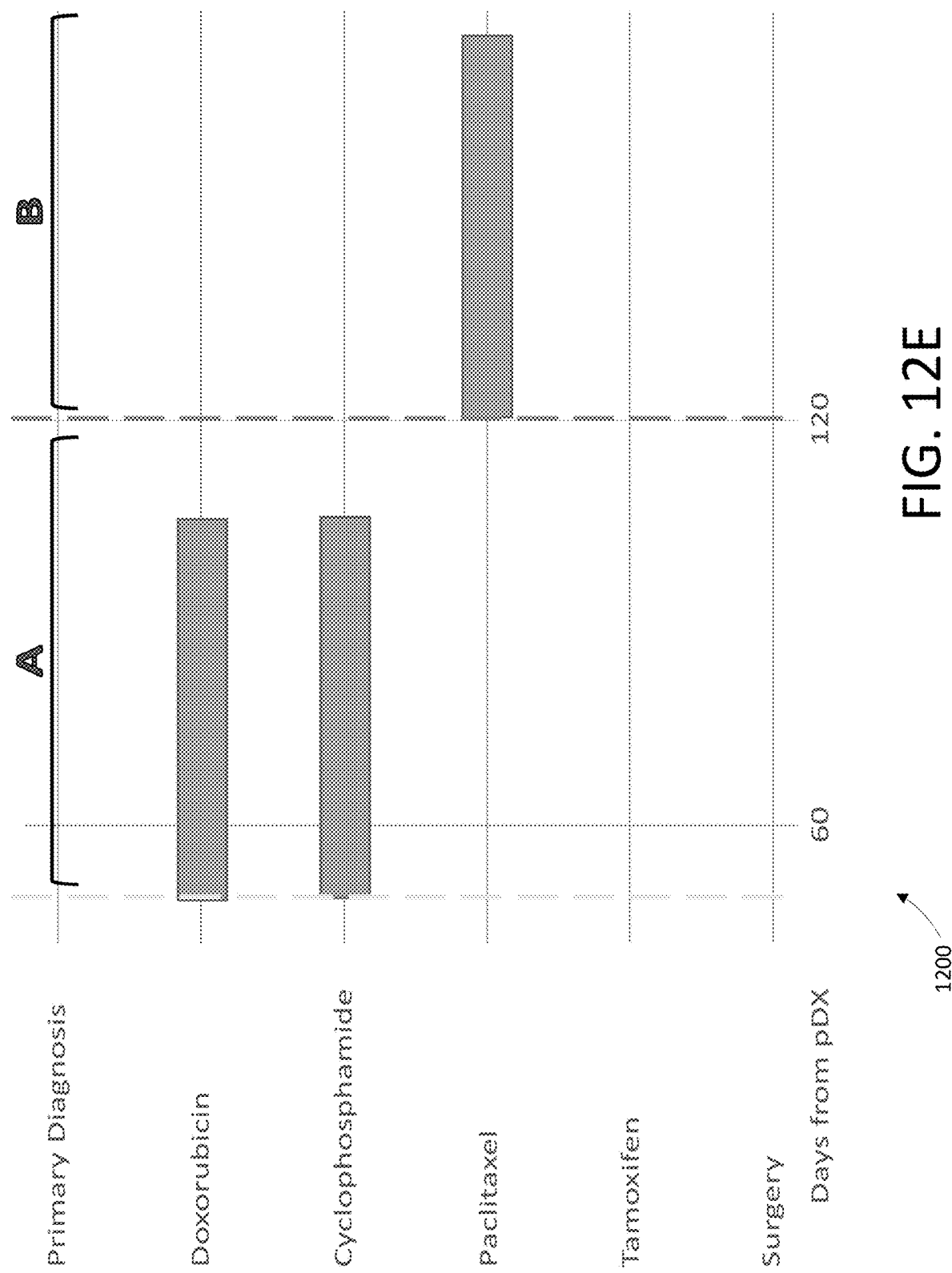
FIG. 12E illustrates applying an expectation maximization model to refine one or more medication intervals in the fourth step of the flow of FIG. 12A.

FIG. 12E illustrates applying an expectation maximization model to refine one or more medication intervals in the fourth step of the flow 1200. Specifically, the flow 1200 can include applying the expectation maximization model to a first medication interval transition "A" and a second medication interval transition "B" in order to determine if the first medication interval should be combined with the second medication interval or kept separate in order to maximize estimated performance. The probability of observing a given interval or intervals can be notated as P(X). The probability of observing a progression event between two intervals can be notated as P_prog (X→Y). The probability of seeing the progression event when splitting an interval into two lines (P(A)P(B) P_prog (A→B)) can be compared to the probability of seeing the progression event when maintaining one line (P(AB)(1-P_prog (A→B))), and the more probable option can be selected as the line assignment. In the example shown in FIG. 12E, the more probable option was determined to be splitting the interval into two lines, thus each of interval "A" and interval "B" have corresponding medication lines.

Figure 12F:
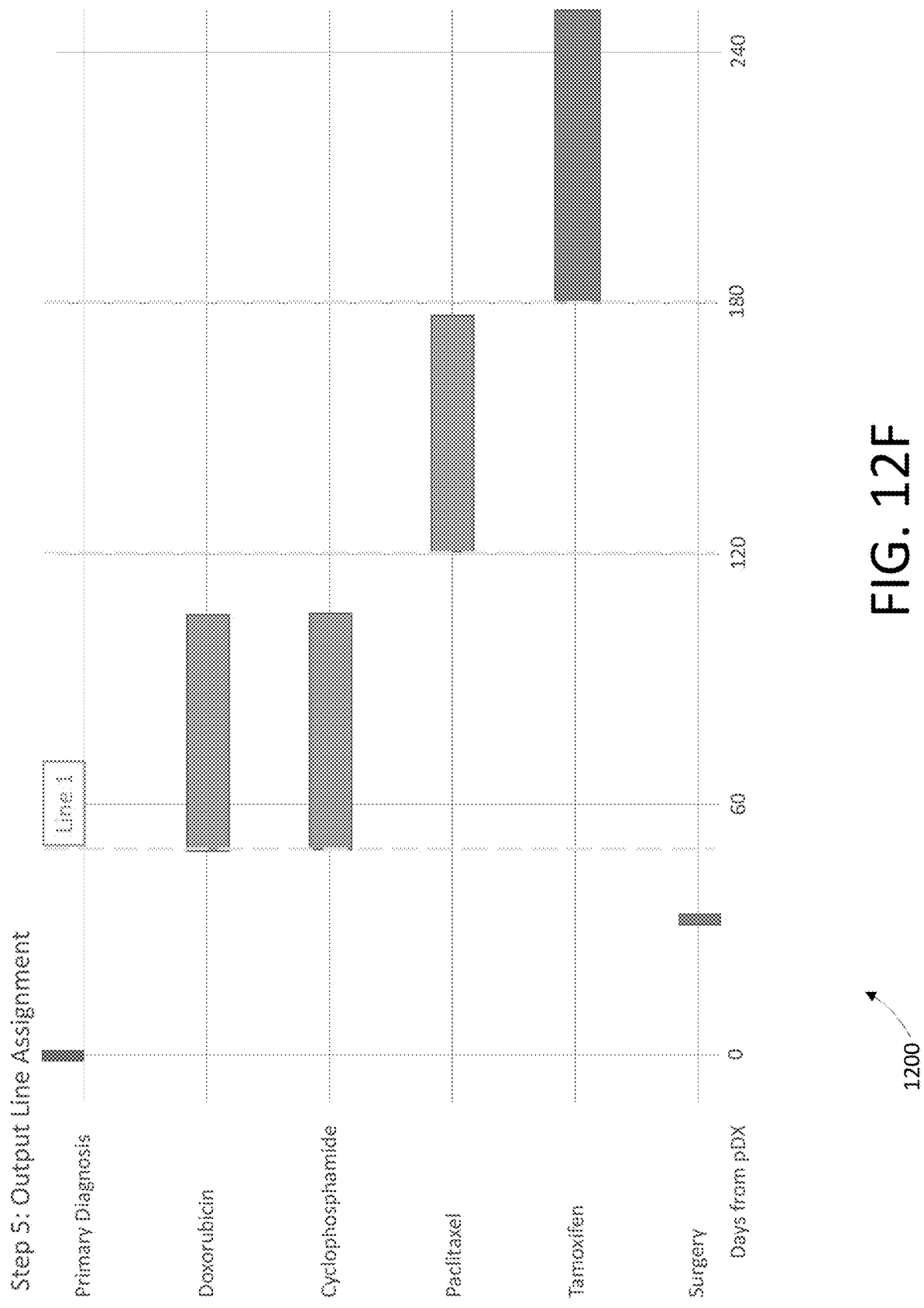
FIG. 12F illustrates outputting line assignments in a fifth step of the flow of FIG. 12A.

FIG. 12F illustrates outputting line assignments in a fifth step of the flow 1200. The line assignments can be associated with one or more potential lines of therapy from the one or more medication intervals. Identification may be performed using a trained model, an exhaustive enumeration with ranking based on likelihood, or other method as disclosed herein. The lines of therapy can include a first line associated with the first, second, and third medication intervals. In some embodiments, the flow 1200 as shown in FIG. 12F can be generated using steps 250 and 260 in FIG. 2.

Figure 13A:
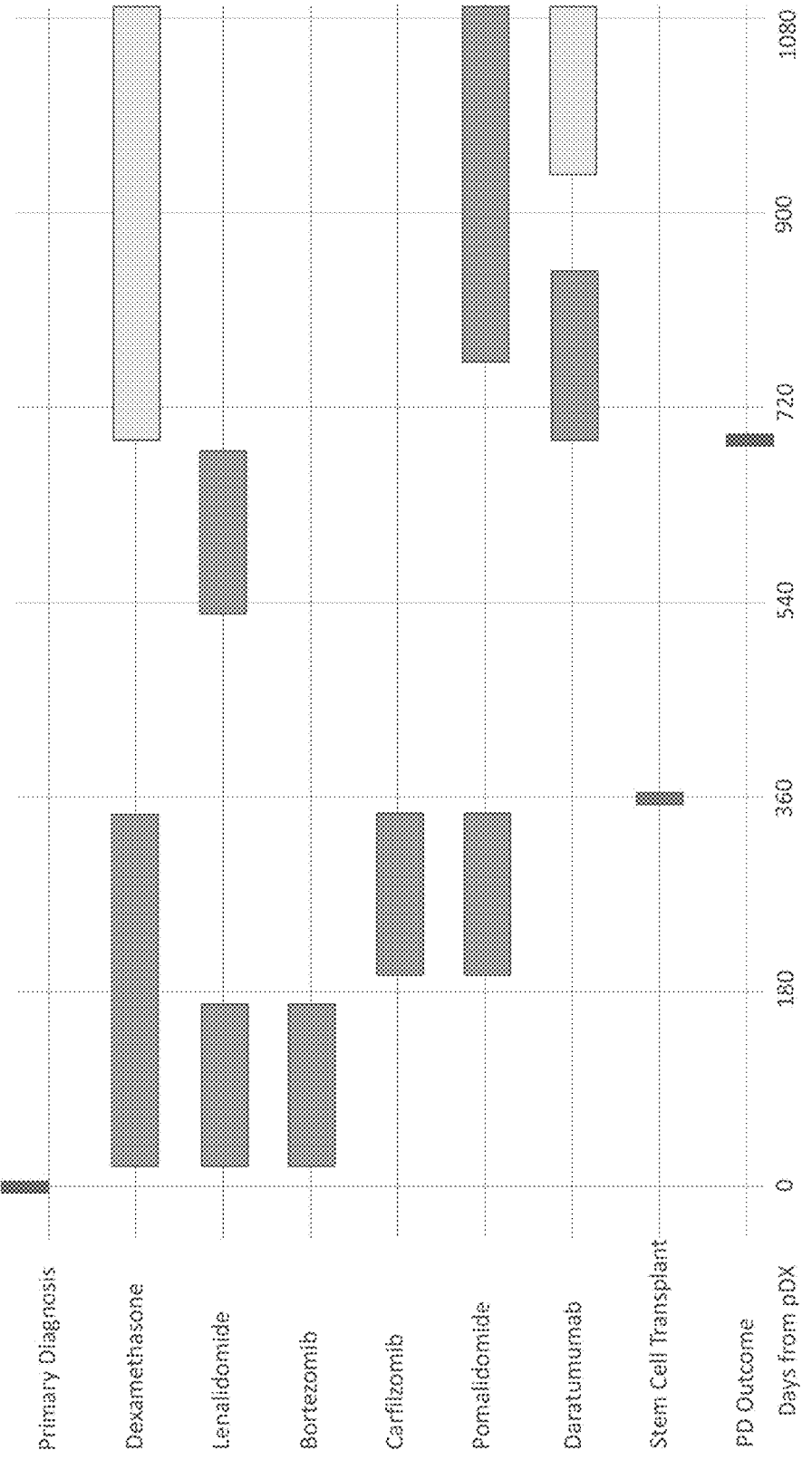
FIG. 13A illustrates a first step of a flow.

Referring now to FIGS. 13A-13F, an exemplary flow 1300 of line of therapy generation is shown. FIG. 13A illustrates a first step of the flow 1300. The first step of the flow 1300 can include combining one or more medications and/or treatments, one or more progressive disease outcomes, and one or more diagnoses (e.g., a cancer diagnosis). In the example flow 1300, a primary diagnosis can define the start of a timeline that events and/or treatments can be mapped to in order to provide one or more time intervals to a user (e.g., an oncologist). As shown, the one or more medications and/or treatments can include Dexamethasone, Lenalidomide, Bortezomib, Carfilzomib, Pomalidomide, Daratumumab, and Stem Cell Transplant. In some embodiments, the flow 1300 as shown in FIG. 13A can be generated using steps 210 and 220 in FIG. 2.

Figure 13B:
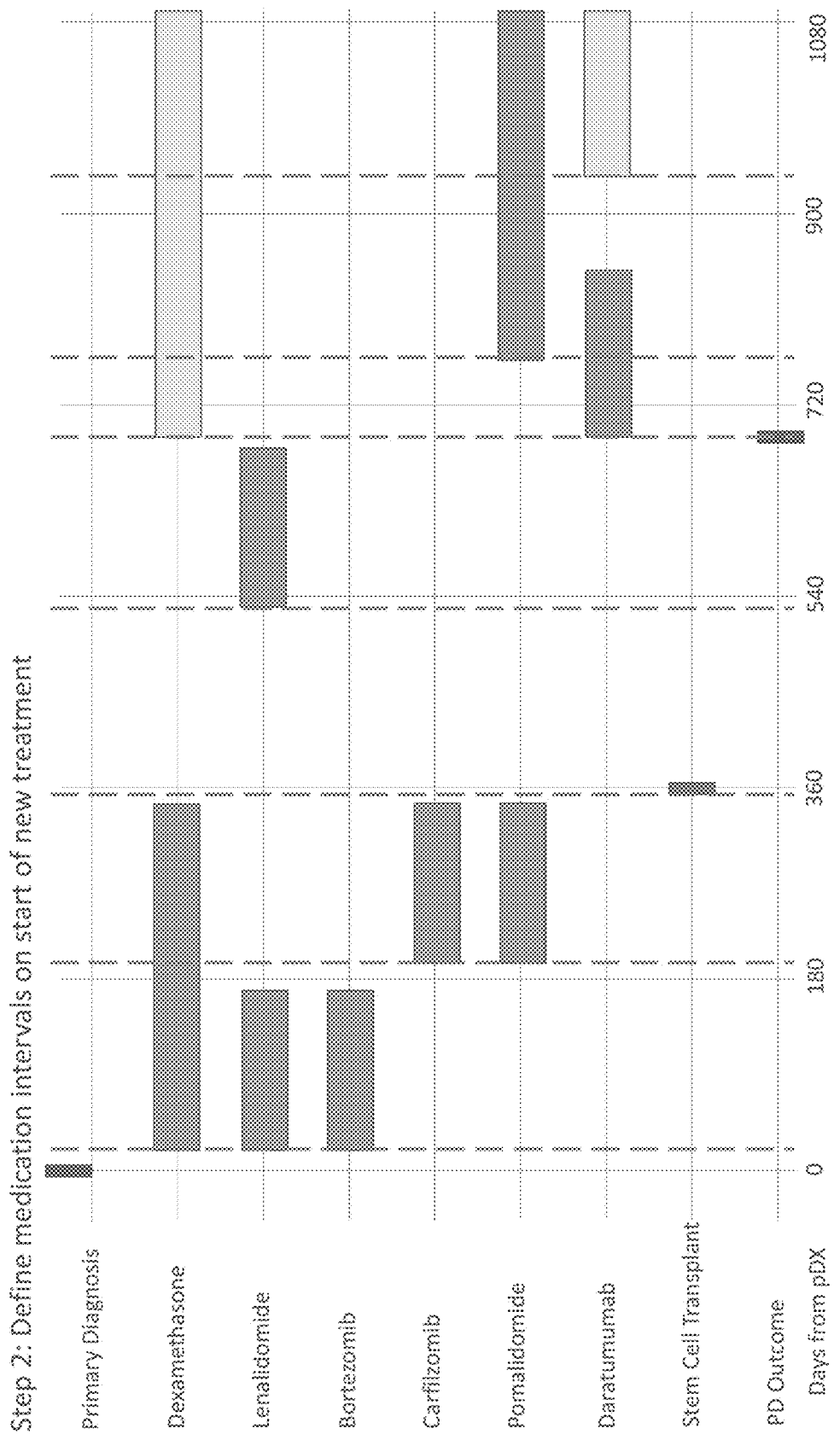
FIG. 13B illustrates a number of medication intervals included in a second step of the flow of FIG. 13A.

FIG. 13B illustrates a number of medication intervals included in a second step of the flow 1300. The flow 1300 in FIG. 13B can be generated based on the one or more medications and/or treatments in FIG. 13A. Certain medications can be associated with a common interval for one or more new treatments. As shown, Dexamethasone, Lenalidomide, and Bortezomib can be associated with a first medication interval that is approximately 5 days after the primary diagnosis. The first medication interval can define the start of a first new treatment. Other medications can be associated with additional medication intervals. As shown, Carfilzomib and Pomalidomide can be associated with the second medication interval that is approximately 180 days after the primary diagnosis. The second medication interval can define the start of a second new treatment. As shown, Stem Cell Transplant can be associated with the third medication interval that is approximately 360 days after the primary diagnosis. The third medication interval can define the start of a third new treatment. As shown, Lenalidomide can be associated with the fourth medication interval that is approximately 540 days after the primary diagnosis. The fourth medication interval can define the start of a fourth new treatment. As shown, Daratumumab and Dexamethasone can be associated with the fifth medication interval that is approximately 700 days after the primary diagnosis. The fifth medication interval can define the start of a fifth new treatment. As shown, Pomalidomide can be associated with the sixth medication interval that is approximately 750 days after the primary diagnosis. The sixth medication interval can define the start of a sixth new treatment. As shown, Daratumumab can be associated with the seventh medication interval that is approximately 930 days after the primary diagnosis. The seventh medication interval can define the start of a seventh new treatment. In some embodiments, the flow 1300 as shown in FIG. 13B can be generated using step 230 in FIG. 2.

Figure 13C:
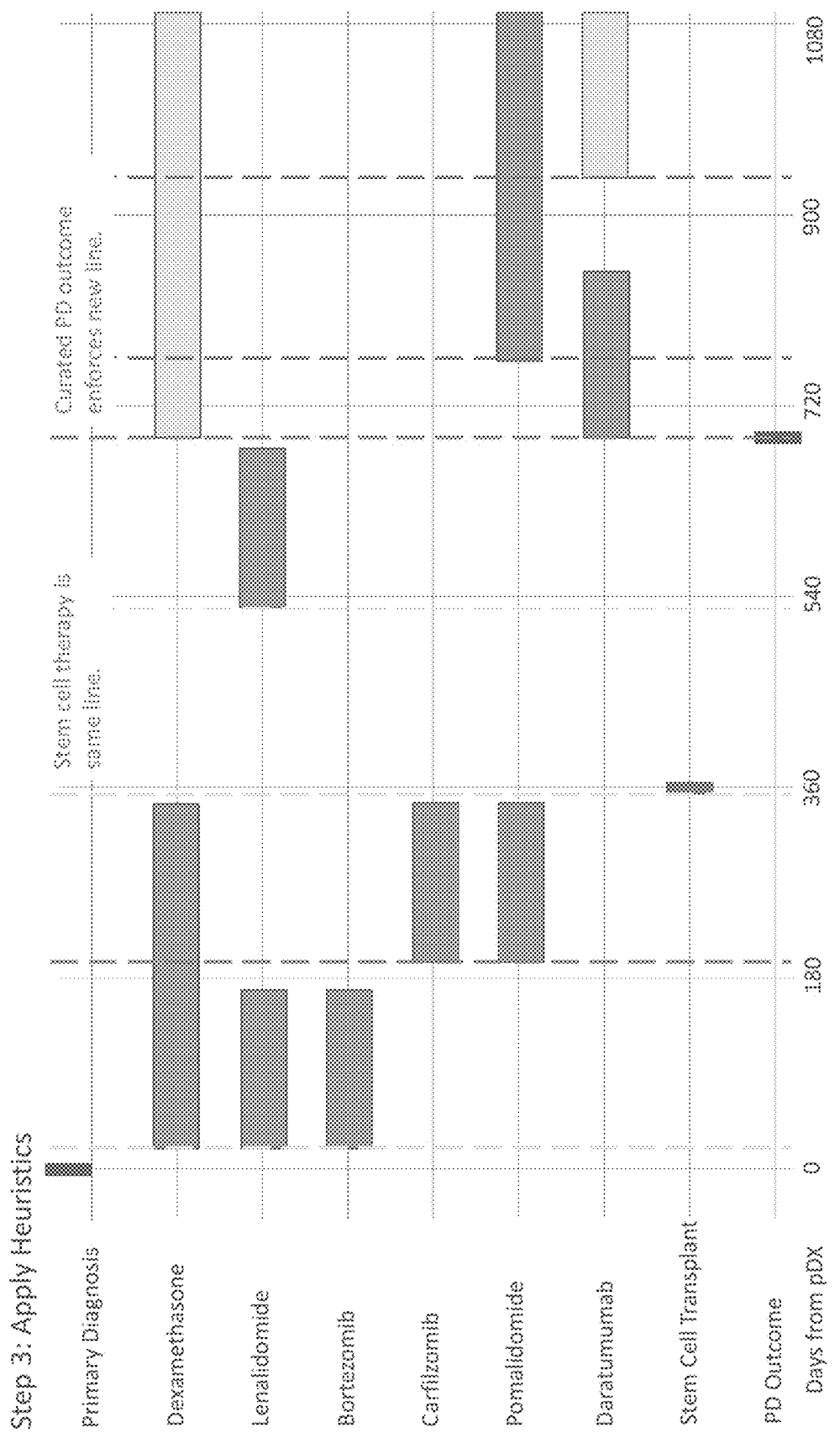
FIG. 13C illustrates applying heuristics to refine one or more medication intervals in a third step of the flow of FIG. 13A.

FIG. 13C illustrates applying heuristics to refine one or more medication intervals in a third step of the flow 1300. The heuristics can refine one or more medication intervals by combining overlapping intervals, splitting intervals up, or adjusting the start and/or end dates according to one or more heuristics, rules, or trained models. The heuristics can refine one or more medication intervals based on a rule associated with the progressive disease outcome. For example, the heuristics can set the fifth medication interval to start at about 700 days after diagnosis based on the progressive disease outcome at about 700 days after diagnosis. In some embodiments, the flow 1300 as shown in FIG. 13C can be generated using step 240 in FIG. 2.

Figure 13D:
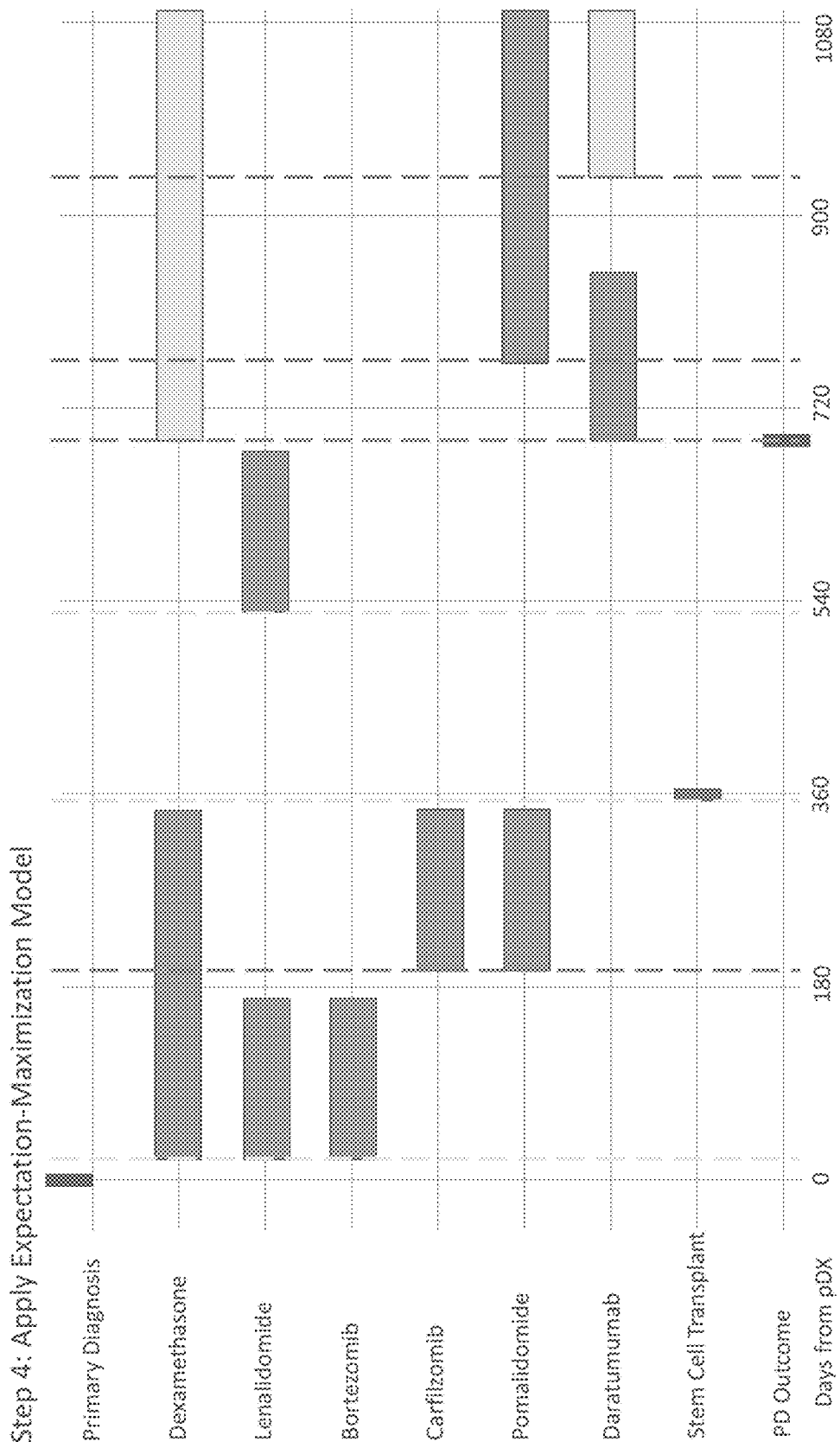
FIG. 13D illustrates applying an expectation maximization model to refine one or more medication intervals in a fourth step of the flow of FIG. 13A.

FIG. 13D illustrates applying an expectation maximization model to refine one or more medication intervals in a fourth step of the flow 1300. For each medication interval, the expectation maximization model can be used to calculate an EM to identify the reliability of the medication interval. In some embodiments, the flow 1300 as shown in FIG. 13D can be generated using step 240 in FIG. 2.

Figure 13E:
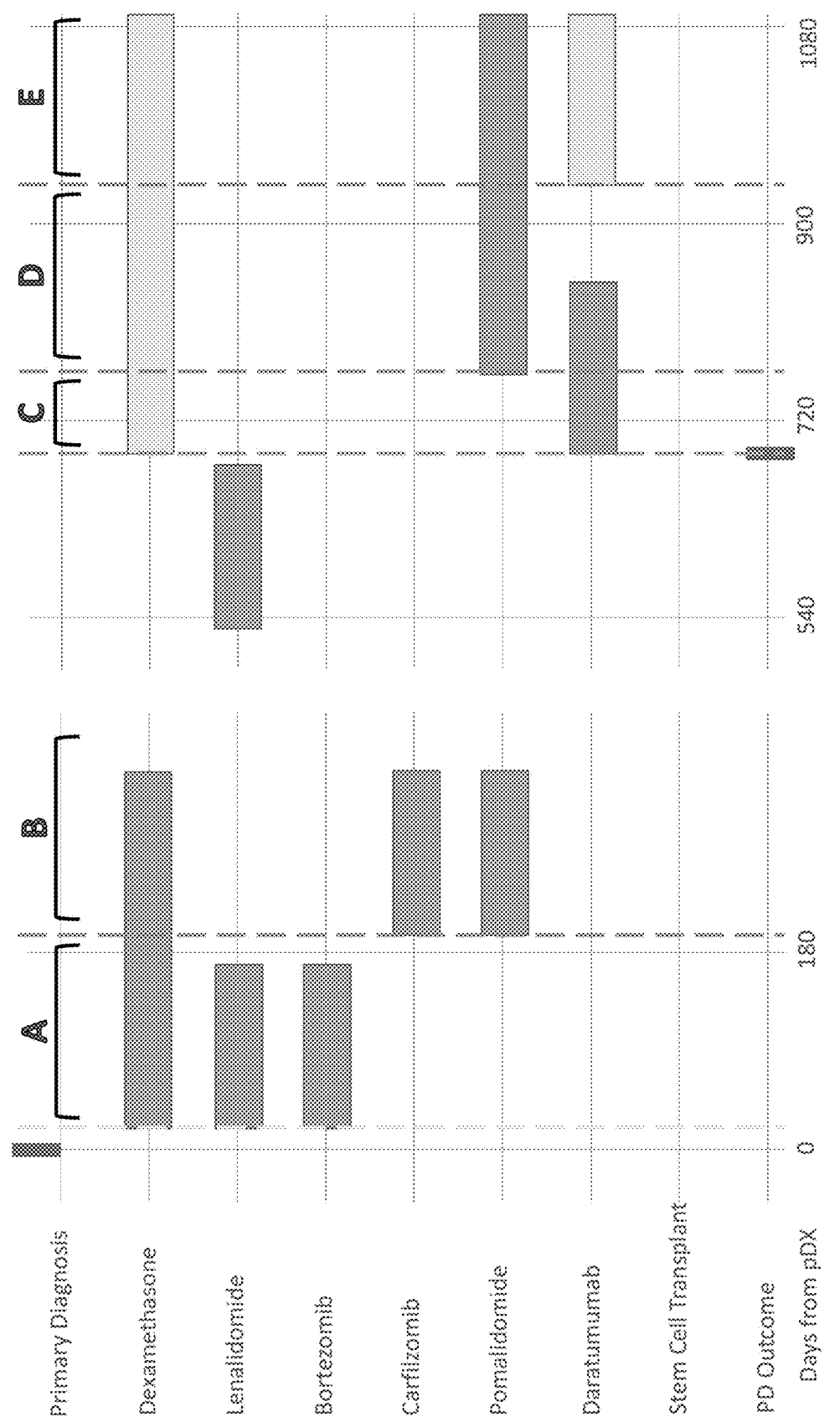
FIG. 13E illustrates applying an expectation maximization model to refine one or more medication intervals in the fourth step of the flow of FIG. 13A.

FIG. 13E illustrates applying an expectation maximization model to refine one or more medication intervals in the fourth step of the flow 1300. Specifically, the flow 1300 can include applying the expectation maximization model to a first medication interval transition "C," a second medication interval transition "D," and a third medication interval transition "E" in order to determine if Dexamethasone, Pomalidomide, and Daratumumab should be combined into a single interval or kept separate in order to maximize estimated performance. The probability of a new line at transition C-D and D-E can be notated as P(C)P(D)P(E) Pprog (C→D) P_prog (D→E). The probability of a new line at transition C-D can be notated as P(CD)P(E)(1-P_prog (C→D)) P_prog (D→E). The probability of a new line at transition D-E can be notated as P(C)P(DE)P_prog (C→D) (1-P_prog (D→E)). The probability of transitions C, D, and E being on one line can be notated as P(CDE)(1-P_prog (C→D))(1-P_prog (D→E)). In the Example shown in FIG. 13E, the probability of C, D, and E being on one line was determined to be the most probable.

Figure 13F:
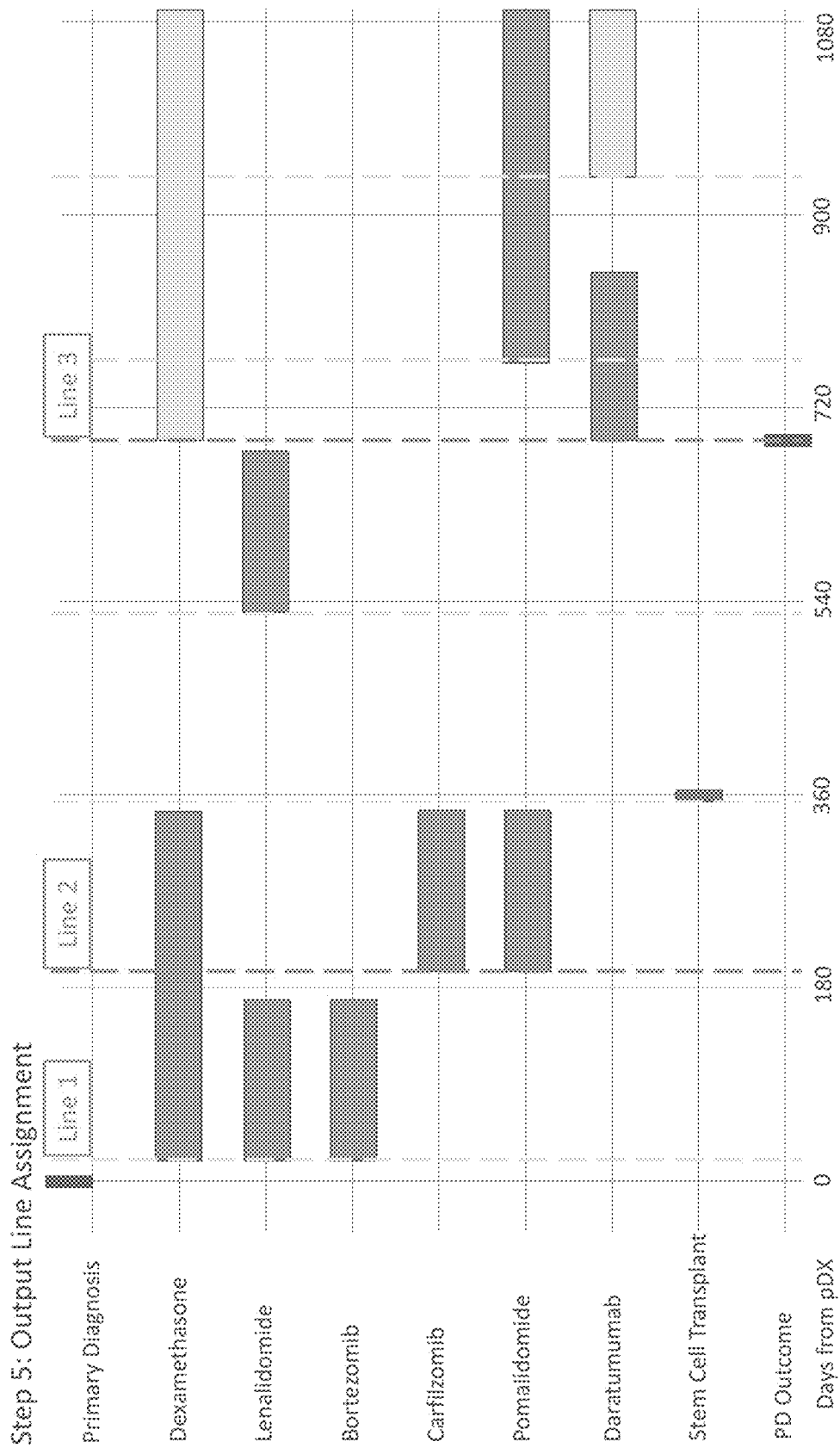
FIG. 13F illustrates outputting line assignments in a fifth step of the flow of FIG. 13A.

FIG. 13F illustrates outputting line assignments in a fifth step of the flow 1300. The line assignments can be associated with one or more potential lines of therapy from the one or more medication intervals. Identification may be performed using a trained model, an exhaustive enumeration with ranking based on likelihood, or other method as disclosed herein. The lines of therapy can include a first line associated with the first medication interval, a second line associated with the second, third, and fourth medication intervals, and a third line associated with the fifth, sixth, and seventh medication intervals. In some embodiments, the flow 1300 as shown in FIG. 13F can be generated using steps 250 and 260 in FIG. 2.

Figure 14:
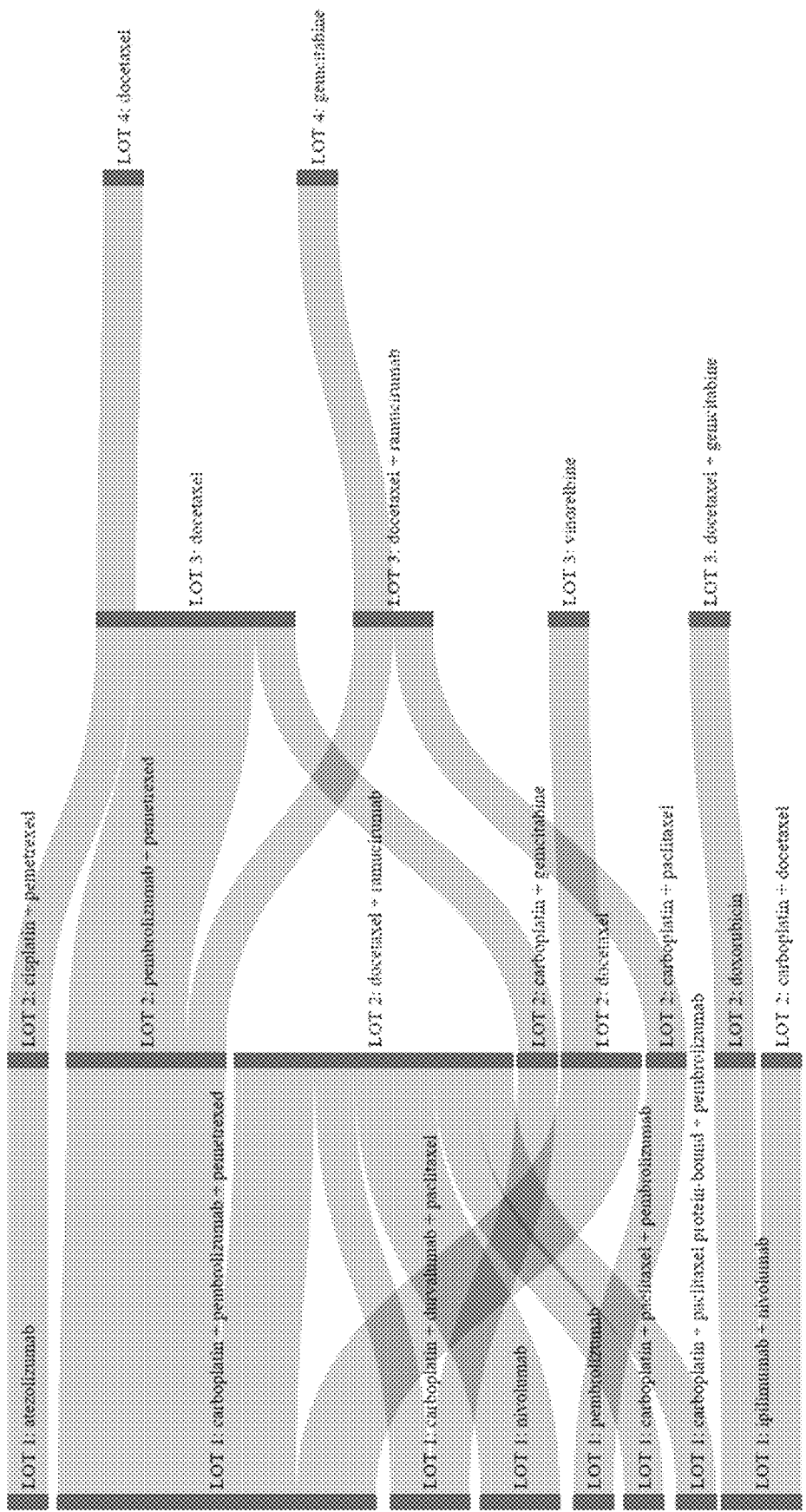
FIG. 14 is a sankey diagram illustrating the lines of therapy as applied to patients having at least an Immuno-Oncology (IO) Regimen therapy.

FIG. 14 is a sankey diagram 140 illustrating the lines of therapy as applied to patients having at least an Immuno-Oncology (IO) Regimen therapy.

For patient records in this example, first lines of therapy may include an IO monotherapy such as atezolizumab, nivolumab, or pembrolizumab; a combination IO and IO such as ipilimumab and nivolumab, or a combination IO monotherapy and chemotherapy such as carboplatin, pembrolizumab, pemetrexed; carboplatin, paclitaxel, pembrolizumab; carboplatin, paclitaxel protein-bound, pembrolizumab; carboplatin, pembrolizumab, pemetrexed; or any other enumerated combinations. Second lines of therapy include additional combinations of IO, hormone, or maintenance therapies. Third lines of therapies include docetaxel, ramucirumad, vinorelbine, and gemcitabine. And Fourth lines of therapies include docetaxel and gemcitabine.

Once a dataset is labeled according to which lines of therapy each patient has been administered, additional analytics may be performed.

Figure 15:
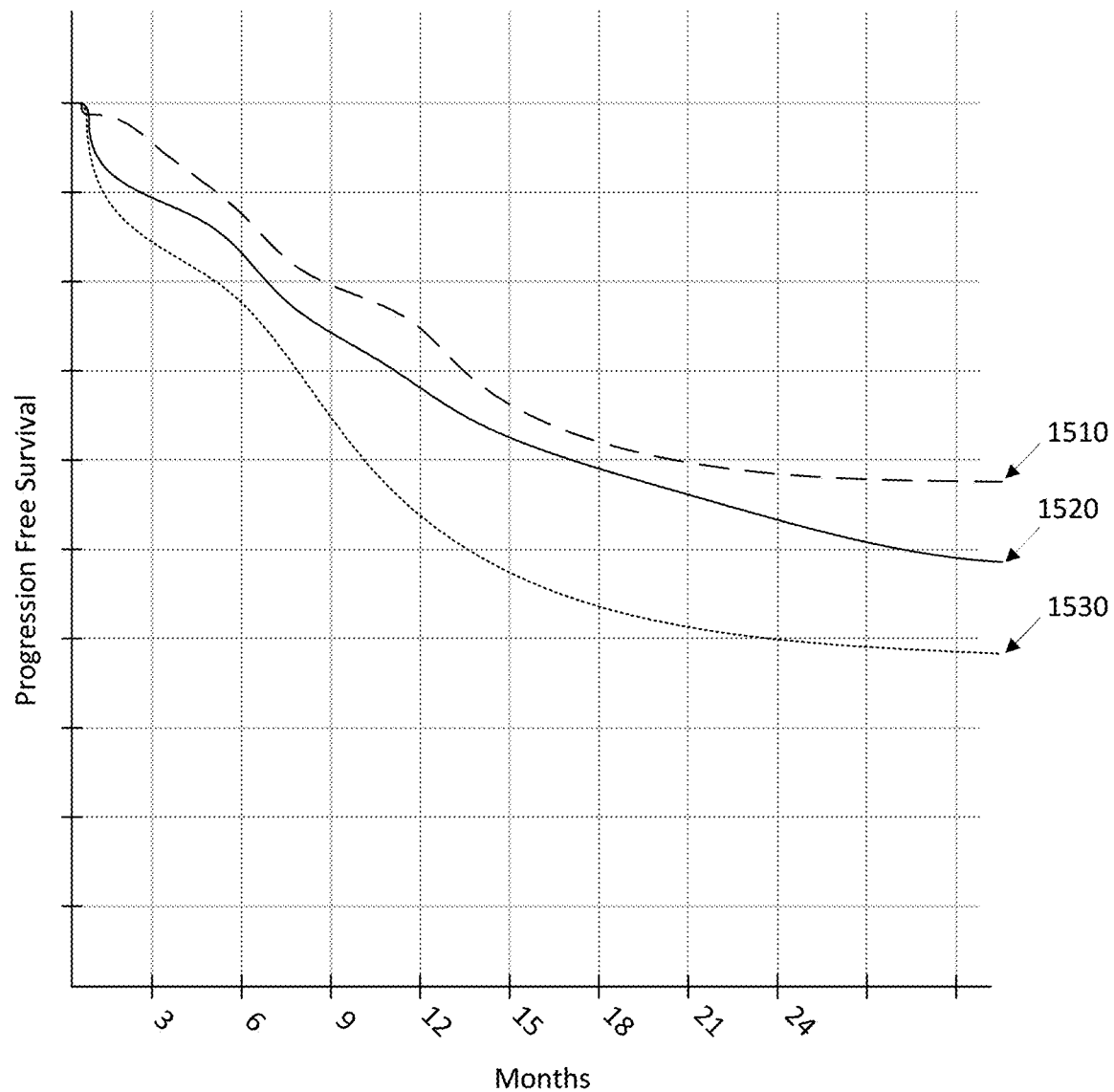
FIG. 15 is a progression-free survival (PFS) graph depicting survival curves of patients who received differing first lines of therapy.

FIG. 15 is a progression-free survival (PFS) graph 1500 depicting survival curves of patients who received differing first lines of therapy.

A cohort of patients may be generated based from a common diagnosis and one or more lines of therapy. Cohort may also filter based upon any of the features included in the patient records. Exemplary lines of therapy 1510, 1520, and 1530. A physician may select a cohort using a web portal, such as web portal 160A-N of FIG. 1, including a collection of features found from patient records, including LoTs labeled according to any system and method disclosed herein and populate a PFS graph to compare patient survival over time with respect to the cohort of patients having the identified characteristics. Here, it can be empirically observed that patients receiving a line of therapy associated with PFS curve 1510 respond better to treatment than patients receiving a line of therapy associated with PFS curve 1520 and both cohort respond better than treatment that patients regimen a line of therapy associated with PFS curve 1530. Based on this information and collection of cohorts, a physician may be more inclined to avoid prescribing LoT associated with curve 1530 and more likely to recommend prescribing LoT associated with curve 1510.

One example of cohort selection via an online web portal and based upon features found in patient records is described in U.S. patent application Ser. No. 16/732,168, filed Dec. 31, 2019 and titled "A Method And Process For Predicting And Analyzing Patient Cohort Response, Progression And Survival", which is incorporated by reference herein for all purposes.

Referring to an exemplary online web portal of U.S. patent application Ser. No. 16/732,168, cohort selection of FIGS. 1-9, analytics of FIGS. 10-28, and customizable web portal (Notebooks) implementation of FIGS. 29-33 are referenced in their entirety as a cohort selection to select and receive features from, for example, clinical health records 110 of FIG. 1, analytics to display based at least on one LoT identified for patients and any additional cohort features in web portal 160*a-n* or GUI 170*a-n*. Customizable notebooks, suitable for displaying customize analytics to a user may include custom target generation, such as for PFS, outliers, effectiveness of surgeries, patient molecular features on LoT performance, adverse events analysis, effects from duration of LoT, or other cohort analytics may be based upon labeled LoT. The exemplary notebook allows a programming approach to design custom interfaces having an R, SQL, or other database software backend for analytics. Custom interfaces may include identifying off-label use of medications and treatments which may be particularly effective. A Notebook may identify and present the informatics to initiate an inquiry into establish new clinical trials to verify the efficacy of the off-label use of the treatment. In one example, a Notebook may identify that a respective LoT is associated with a generic medication name, a brand medication name, and treatment roll-up class (such as type of therapy [targeted, initiation, maintenance, chemotherapy, radiotherapy, Tyrosine kinase inhibitors (TKI), etc.], dosage of medications within a LoT, and/or method of administration of the therapy, such as oral, intravenous, exposure to radiation, etc.

Figure 16:
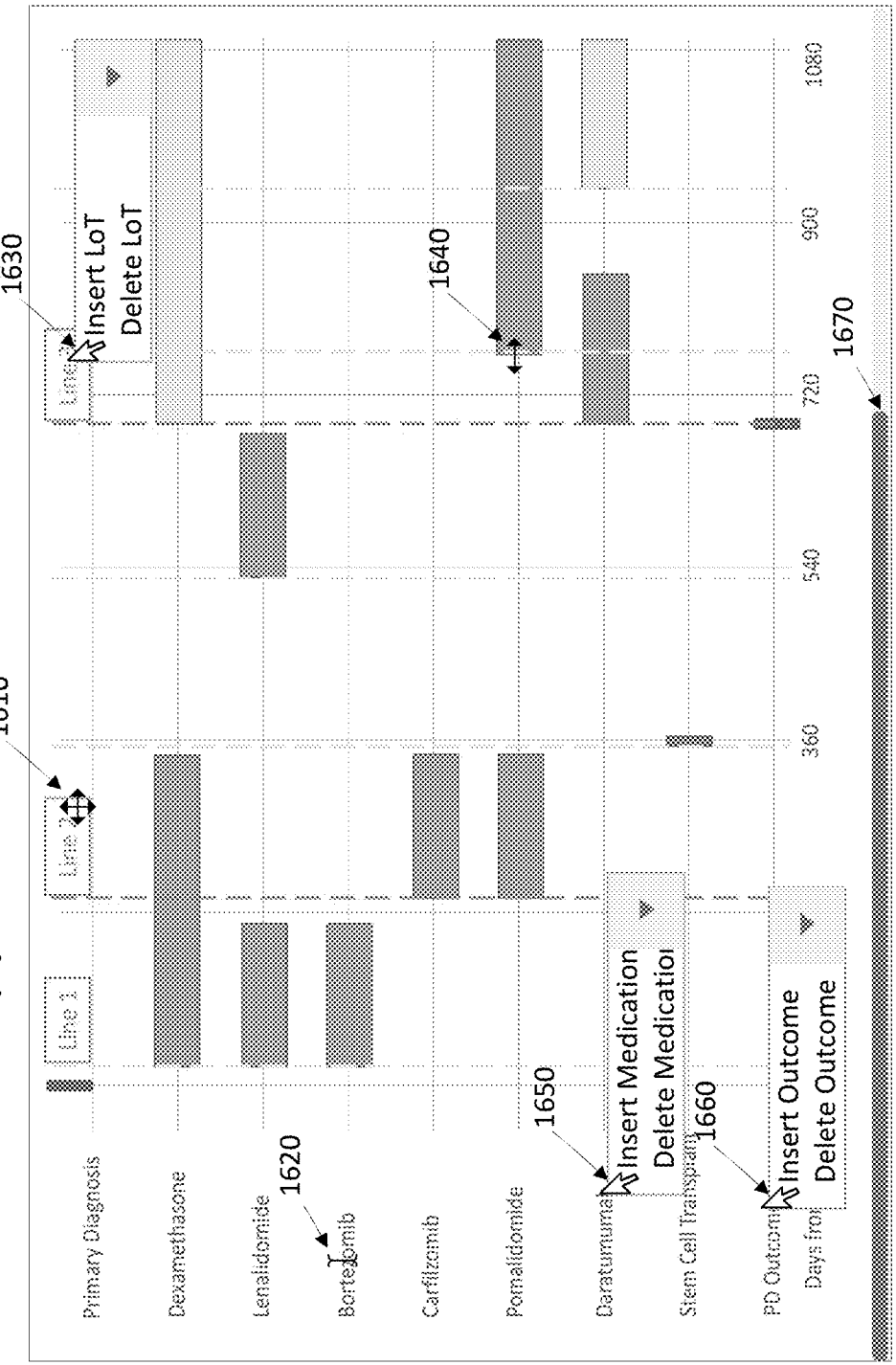
FIG. 16 is an illustration of a line of therapy editing tool for a user to edit lines of therapy for a patient according to one embodiment.

FIG. 16 is an illustration of a line of therapy editing tool 1600 for a user to edit lines of therapy for a patient according to one embodiment.

A line of therapy editing tool may receive any patient from a set of patients having lines of therapy identified according to the methods and systems herein. Once a patient has been loaded, a timeline similar to those of FIGS. 11-13 is loaded. In another embodiment, a timeline similar to those of FIGS. 8-10 may similarly be loaded. The user may user their cursor to perform certain manipulations to correct perceived defects in the LoT labeling performed by the unsupervised artificial intelligence engine.

For example, a user may drag and drop 1610 any line of therapy designation to recalibrate new LoT based on the new position of the enumerated LoT. A user may edit 1620 the medication names to correct spelling errors or replace a brand name with a generic name or class of drugs. A user may right click 1630 at the primary diagnosis axis to insert or delete a LoT at the mouse cursor. A user may drag and drop 1640 a medication interval to edit the start date or end date of the interval. A user may right click 1650 a medication to insert a new medication or delete a medication. A user may right click 1660 an outcome to insert a new outcome such as a surgery, procedure, or other superseding event to the record.

While the controls 1610-1660 are illustrated with respect to mouse events such as click and drag and right click, one of ordinary skill in the art would recognize that these controls may be manipulated using different events such as a keyboard control, touch screen control, or similar interaction with a Input/Output device of a PC or interface of a mobile device.

Figure 17:
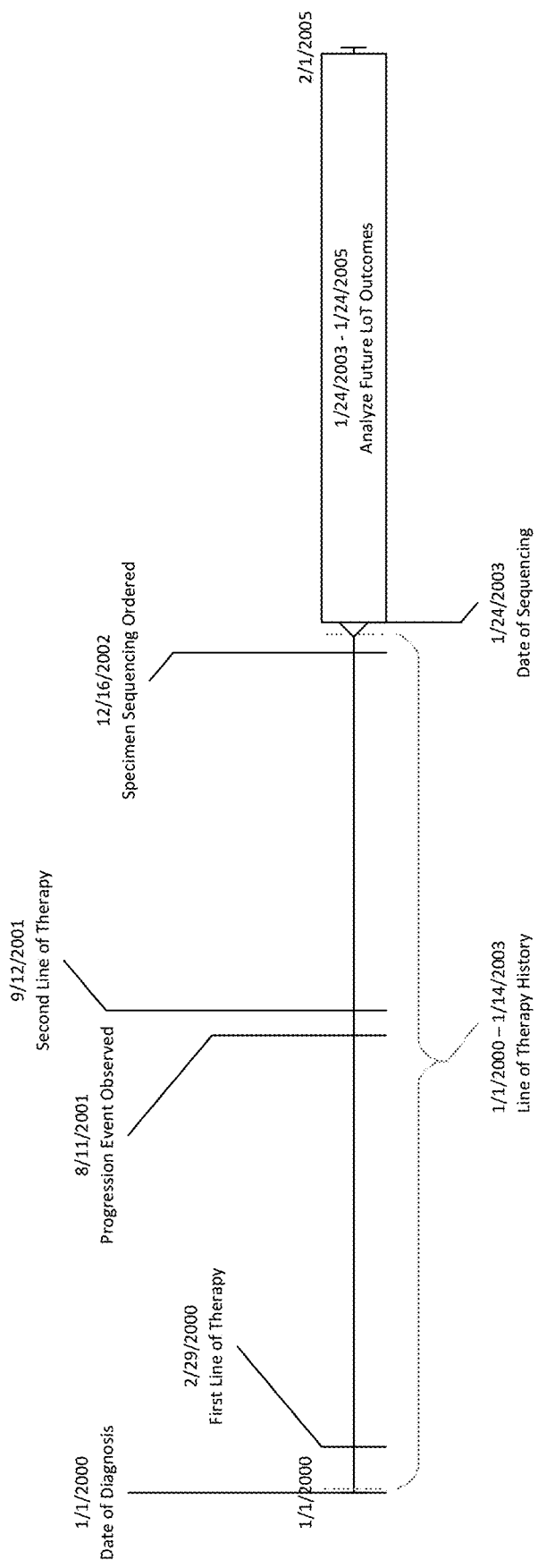
FIG. 17 is an illustration of a structured data representation of a patient timeline after LoT labeling has been performed according to an embodiment.

FIG. 17 is an illustration of a structured data representation of a patient timeline 1700 after LoT labeling has been performed according to an embodiment.

Patient timeline 1700 represents all important interval anchors for a patient record having LoT labels inserted. In this example, a patient receives a primary cancer diagnosis on Jan. 1, 2000, begins a first line of therapy on Feb. 29, 2000, approximately 16 months later a progression event is observed on Aug. 11, 2001 where the progression event is qualified as a treatment internal superseding event, a second line of therapy is administered beginning Sep. 12, 2001, and the patient has a genetic sequencing performed on Dec. 16, 2002, likely due to a progression event such as metastasis of a tumor to another organ site. As of the date of sequencing, the timeline is available to the treating physician, for example, thorough web portal 160A-N. The physician may then utilize the portal to view future LoT outcomes based on similar cohorts of patients and personalize the patients next LoT to improve the likelihood of a positive response. Other analytics include evaluation of other treatments, procedures than those labeled as LoTs, evaluation of genetic variants in the outcome of treatments, identification of a level of risk for the patient to metastasize or progress at any time during treatment, and other analytics to personalize the treatment of the patient and improve positive outcomes.

Figure 18:
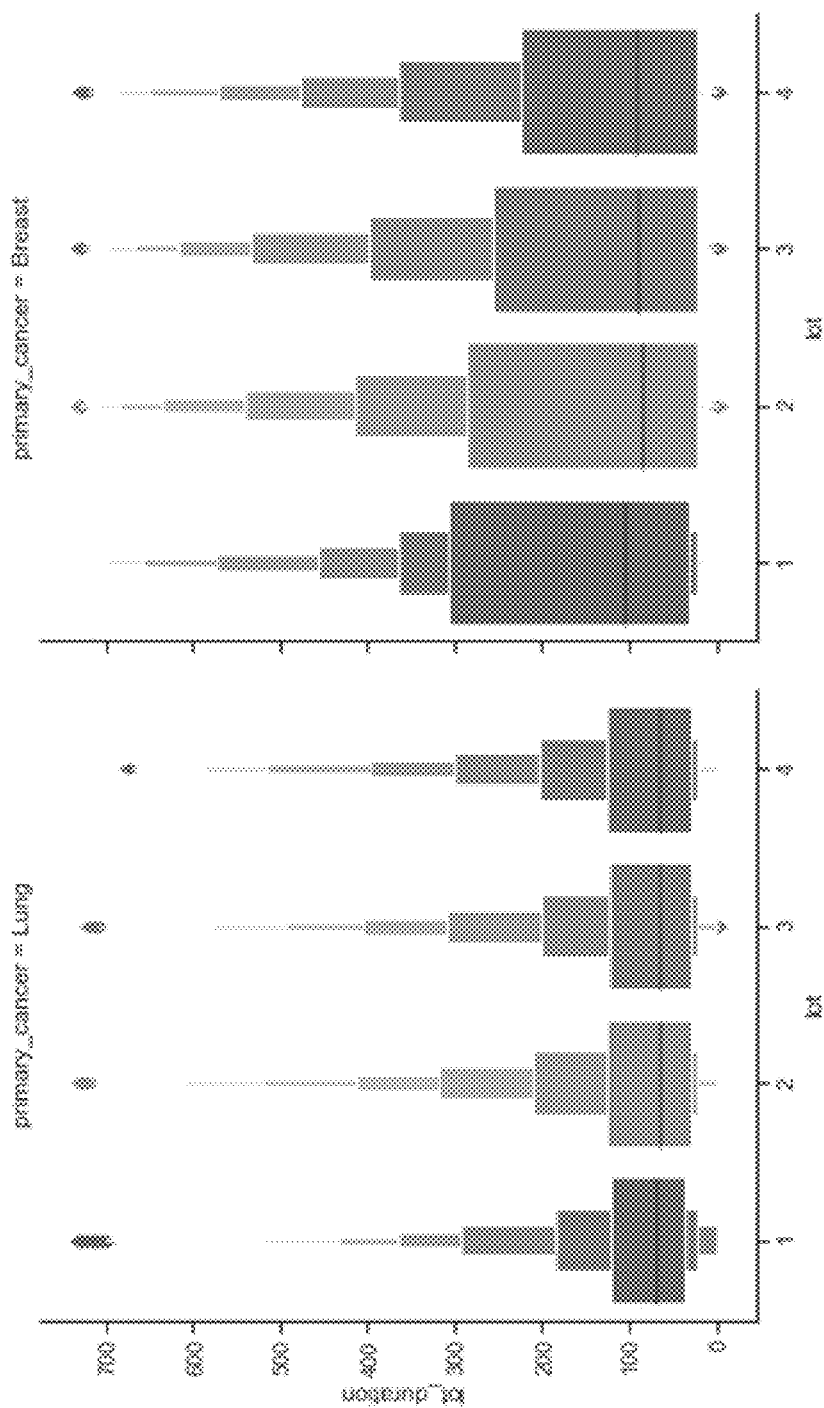
FIG. 18 is a boxenplot illustration of the average duration of LoTs identified from a cohort of patients in a lung cancer cohort and a breast cancer cohort.

FIG. 18 is a boxenplot illustration of the average duration of LoTs 1800 identified from a cohort of patients in a lung cancer cohort and a breast cancer cohort.

As referenced above, cancer specific intervals may be learned from the training of the artificial intelligence engine on a plurality of patients. Once such learning relates to the average duration of treatments so that correct dates may be imputed and that intervals are appropriately sized to provide meaningful potential LoT selections for the model to label from. In one example, Lung cancer patients may experience a majority of treatment intervals at approximately 70 days with few extending beyond 120 days. Analysis of LoTs 1-4 shows that there is very little variation across each successive line of therapy in a lung cancer diagnosis. Therefore, a lung cancer interval threshold may be approximately 70 days to 120 days and not change depending on the LoT interval being evaluated. However, in a breast cancer diagnosis, the majority of treatment intervals sit around 100 days with a first LoT taking as long as 300 days, second LoT taking as long as 290 days, third LoT taking as long as 260 days, and a fourth LoT taking as long as 210 days. Analytics for breast cancer identify that the thresholds for medication durations and treatment intervals are 2-3 times longer than those of lung cancer.

Figure 19:
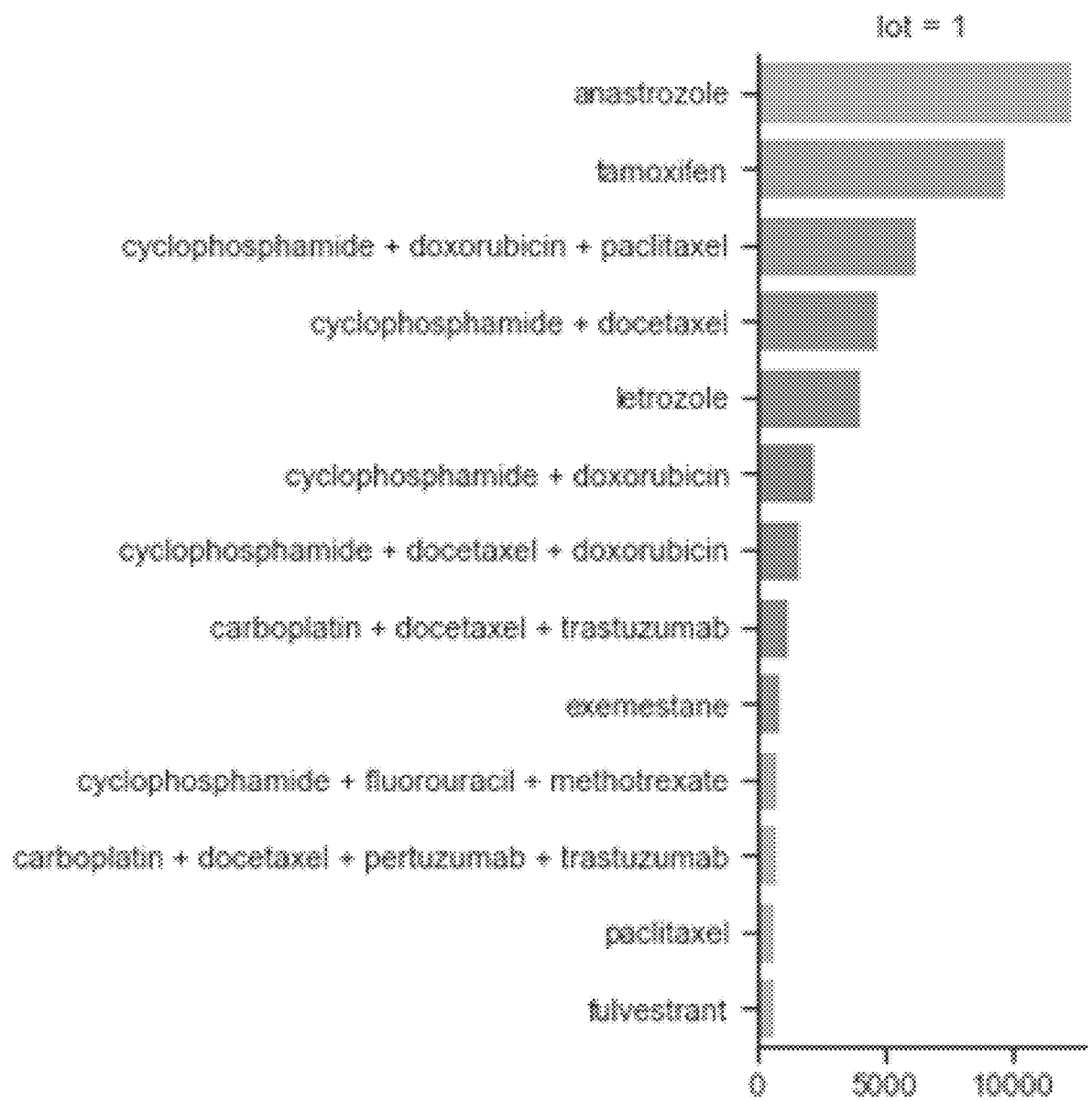
FIG. 19 is an illustration of LoT frequencies based on a first LoT for breast cancer medications administered to patients.

FIG. 19 is an illustration of LoT frequencies 1900 based on a first LoT for breast cancer medications administered to patients.

Based upon a model generated via unsupervised learning, a majority of breast cancer patients will start with a first line of therapy of anastrozole, tamoxifen, or AC-T (the drugs doxorubicin hydrochloride (Adriamycin) and cyclophosphamide, followed by treatment with paclitaxel (Taxol)). While there appear to be great variance across first LoT selection for breast cancer patients, FIG. 20 represents a second LoT frequency distribution for breast cancer patients.

Figure 20:
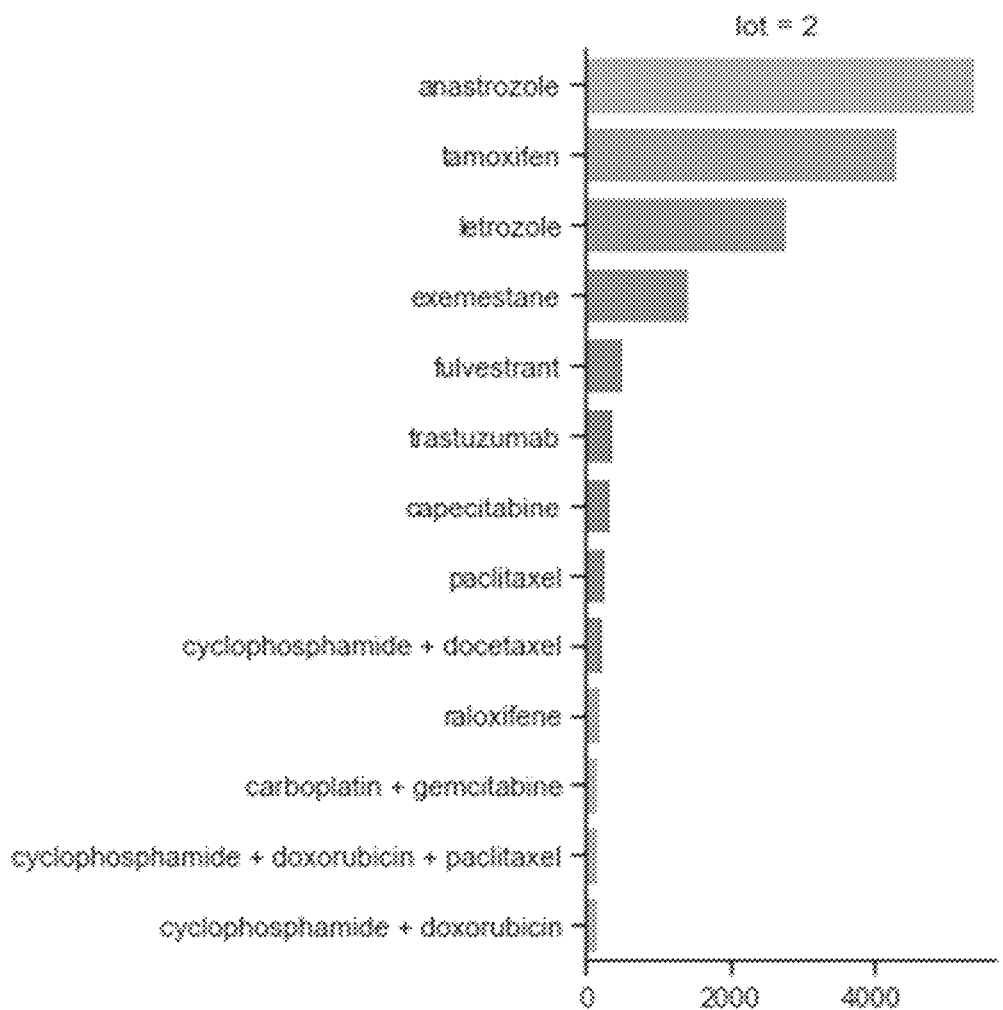
FIG. 20 is an illustration of LoT frequencies based on a second LoT for breast cancer medications administered to patients.

FIG. 20 is an illustration of LoT frequencies 2000 based on a second LoT for breast cancer medications administered to patients.

Based upon a model generated via unsupervised learning, a majority of breast cancer patients will follow their first line of therapy of FIG. 19 with a second line of therapy of anastrozole, tamoxifen, letrozole. Similarly, it may be noted that AC-T regimen is never prescribed as a second LoT for patients and therefore makes sense that it does not appear in the learned labeling space for second lines of therapy. While there is less variance across second LoT selection for breast cancer patients, this is to be expected as maintenance therapies are generally prescribed treatments at the second line of therapy.

Figure 21:
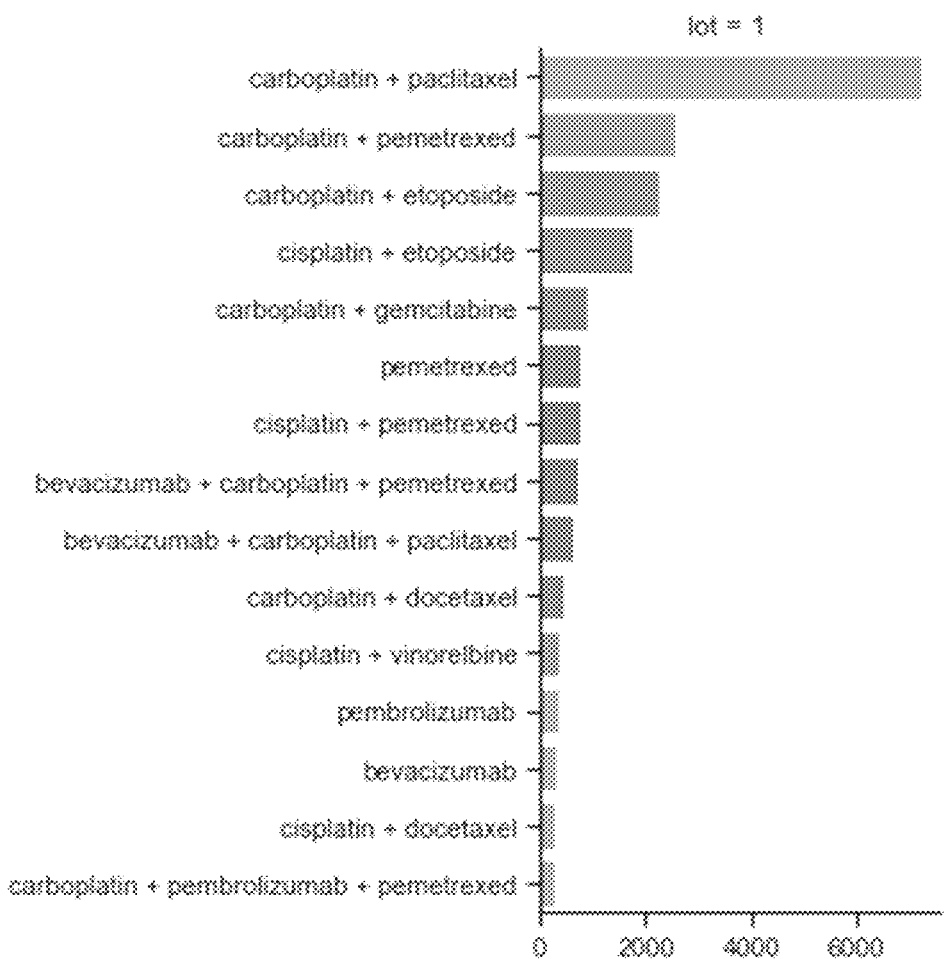
FIG. 21 is an illustration of LoT frequencies based on a first LoT for non-small cell lung cancer (NSCLC) medications administered to patients.

FIG. 21 is an illustration of LoT frequencies 2100 based on a first LoT for non-small cell lung cancer (NSCLC) medications administered to patients.

Based upon a model generated via unsupervised learning, a majority of NSCLC patients start with carboplatin and paclifaxel with some patients starting with carboplatin and either pemetrexed or etoposide. Another point of accuracy includes that none of the NSCLC patients start with a targeted therapy, such as those listed in FIG. 22.

Figure 22:
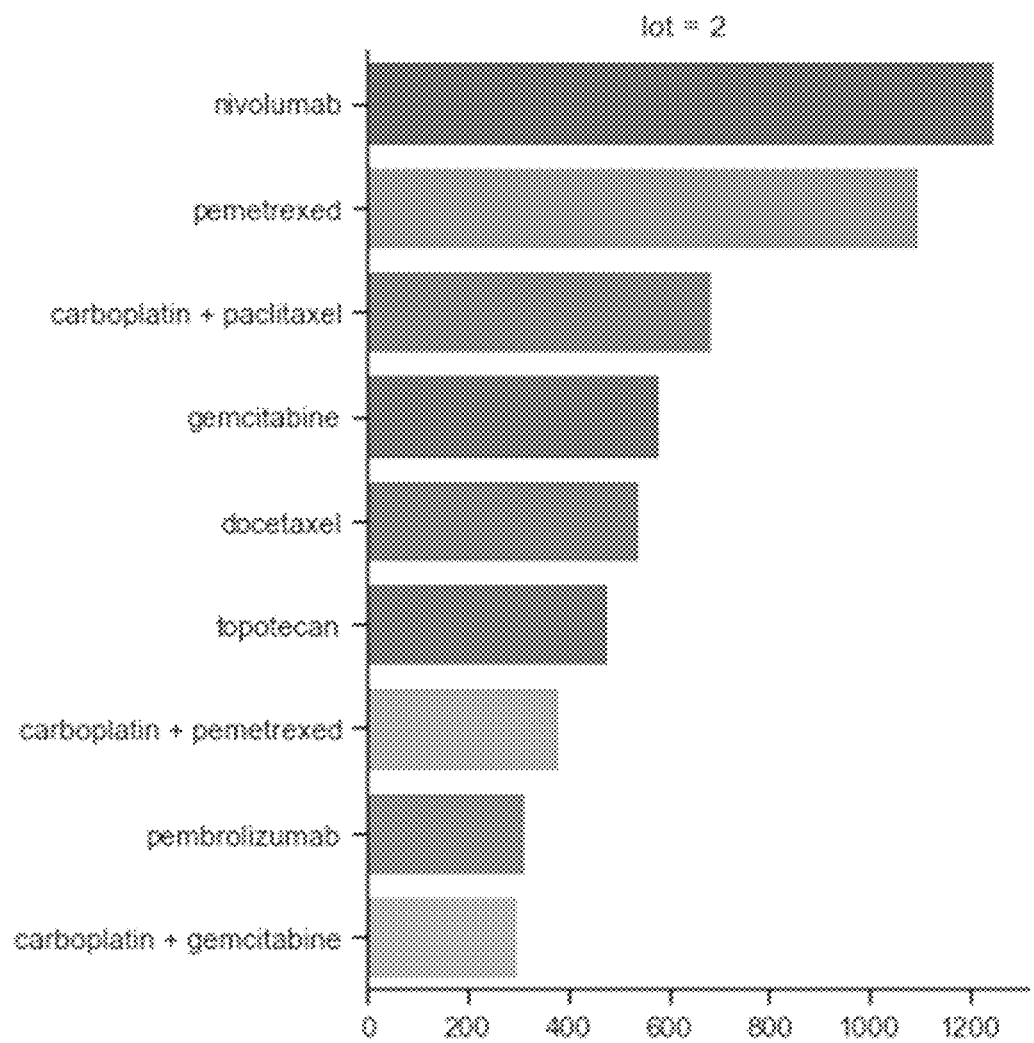
FIG. 22 is an illustration of LoT frequencies based on a second LoT for non-small cell lung cancer medications administered to patients.

FIG. 22 is an illustration of LoT frequencies 2200 based on a second LoT for non-small cell lung cancer medications administered to patients.

Based upon a model generated via unsupervised learning, a majority of NSCLC cancer patients will follow their first line of therapy of FIG. 21 with a second line of therapy of nivolumab or pemetrexed while a fairly even distribution will attempt targeted therepies of gemcitabine, docetaxel, or topotecan as the second LoT.

FIGS. 19-22 illustrate the frequency of occurrence of specific LoT across all patients in their respective primary diagnosis cohorts. While the illustrative examples were limited to breast and lung cancers, the methods and systems disclosed herein may be applied to any cancer diagnosis without departing from the embodiments described herein. Further, the rankings for intervals and potential lines of therapy may be directly derived from the likelihoods based on the frequencies. For example, if a first LoT occurs in 50% of patients as a first LoT, it may be directly given a likelihood of 50% when a respective treatment interval corresponds to it during LoT labeling. Additionally, an artificial intelligence engine may generator further likelihood estimations based upon the frequency of LoT succeeding one another. For example, if a first LoT of carboplatin and paclitaxel is followed by a second LoT of nivolumab 80% of the time, and both carboplatin and paclitaxel and nivolumab are in consecutive treatment intervals, the likelihood of a first LoT being carboplatin and paclitaxel and a second line of therapy being nivolumab will be scaled higher than if the record included only a first line of carboplatin and paclitaxel or only a second line of nivolumab.

Figure 23:
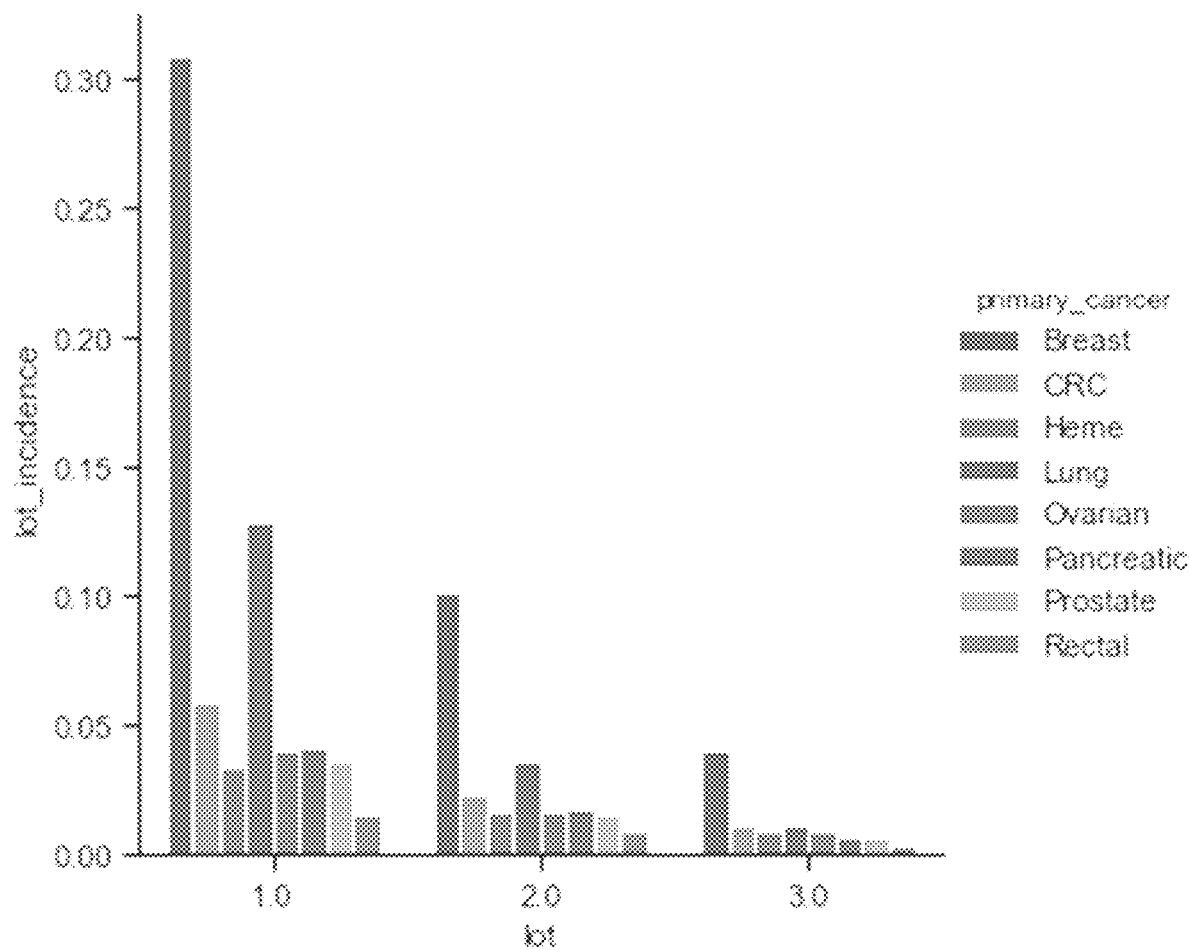
FIG. 23 is a bar chart illustration of the proportion of patients for each primary cancer that were assigned to a cohort including at least one of an enumerated LoT.

FIG. 23 is a bar chart illustration 2300 of the proportion of patients for each primary cancer that were assigned to a cohort including at least one of an enumerated LoT.

In this example, breast cancer patients are distributed such that 70% have a first LoT labeled, 15% have a second LoT labeled, and only 5% have a third LoT labeled. Conversely, for a primary diagnosis of colorectal cancer (CRC), only 60% have a first LoT labeled, 15% have a second LoT labeled, and 5% have a third LoT labeled. Patients without a respective label may be evaluated by hand to identify what label, if any, may be applied.

Figure 24:
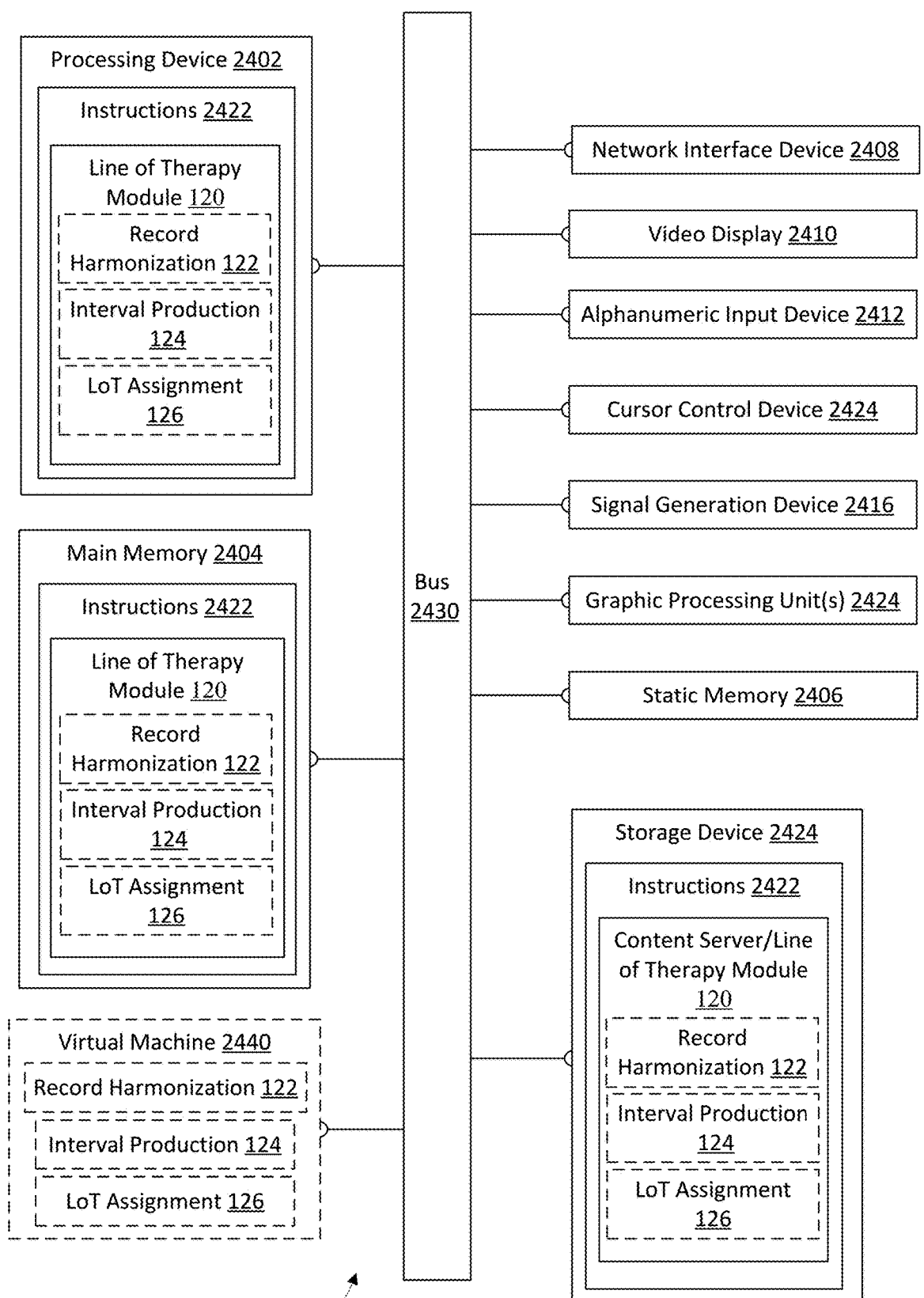
FIG. 24 is an illustration of a block diagram of an implementation of a computer system in which some implementations of the disclosure may operate.

FIG. 24 is an illustration of an example machine of a computer system 2400 within which a set of instructions, for causing the machine to perform any one or more of the methodologies discussed herein, may be executed. In alternative implementations, the machine may be connected (such as networked) to other machines in a LAN, an intranet, an extranet, and/or the Internet.

The machine may operate in the capacity of a server or a client machine in client-server network environment, as a peer machine in a peer-to-peer (or distributed) network environment, or as a server or a client machine in a cloud computing infrastructure or environment. The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 2400 includes a processing device 2402, a main memory 2404 (such as read-only memory (ROM), flash memory, dynamic random access memory (DRAM) such as synchronous DRAM (SDRAM) or DRAM, etc.), a static memory 2406 (such as flash memory, static random access memory (SRAM), etc.), and a data storage device 2418, which communicate with each other via a bus 2430.

Processing device 2402 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 2402 may also be one or more special-purpose processing devices such as an application specific integrated circuit (ASIC), a field programmable gate array (FPGA), a digital signal processor (DSP), network processor, or the like. The processing device 2402 is configured to execute instructions 2422 for performing the operations and steps discussed herein.

The computer system 2400 may further include a network interface device 2408 for connecting to the LAN, intranet, internet, and/or the extranet. The computer system 2400 also may include a video display unit 2410 (such as a liquid crystal display (LCD) or a cathode ray tube (CRT)), an alphanumeric input device 2412 (such as a keyboard), a cursor control device 2414 (such as a mouse), a signal generation device 2416 (such as a speaker), and a graphic processing unit 2424 (such as a graphics card).

The data storage device 2418 may be a machine-readable storage medium 2428 (also known as a computer-readable medium) on which is stored one or more sets of instructions or software 2422 embodying any one or more of the methodologies or functions described herein. The instructions 2422 may also reside, completely or at least partially, within the main memory 2404 and/or within the processing device 2402 during execution thereof by the computer system 2400, the main memory 2404 and the processing device 2402 also constituting machine-readable storage media.

In one implementation, the instructions 2422 include instructions for a Line of Therapy module (such as the Line of Therapy module 120 of FIG. 1) and/or a software library containing methods that function as a Line of Therapy module. The instructions 2422 may further include instructions for a Record Harmonization module 122, Interval production module 124, and Lot Assignment module 126. (such as the Record Harmonization module 122, Interval production module 124, and Lot Assignment module 126 of FIG. 1) While the machine-readable storage medium 2428 is shown in an example implementation to be a single medium, the term "machine-readable storage medium" should be taken to include a single medium or multiple media (such as a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media. The term "machine-readable storage medium" shall accordingly exclude transitory storage mediums such as signals unless otherwise specified by identifying the machine readable storage medium as a transitory storage medium or transitory machine-readable storage medium.

In another implementation, a virtual machine 2440 may include a module for executing instructions for a Record Harmonization module 122, Interval production module 124, and Lot Assignment module 126. In computing, a virtual machine (VM) is an emulation of a computer system. Virtual machines are based on computer architectures and provide functionality of a physical computer. Their implementations may involve specialized hardware, software, or a combination of hardware and software.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "providing" or "calculating" or "determining" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise one or more general purpose computers selectively activated or reconfigured by a computer program stored in the computer(s). Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct a more specialized apparatus to perform the method. The structure for a variety of these systems will appear as set forth in the description below. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (such as a computer). For example, a machine-readable (such as computer-readable) medium includes a machine (such as a computer) readable storage medium such as a read only memory ("ROM"), random access memory ("RAM"), magnetic disk storage media, optical storage media, flash memory devices, etc.

In the foregoing specification, implementations of the disclosure have been described with reference to specific example implementations thereof. It will be evident that various modifications may be made thereto without departing from the broader spirit and scope of implementations of the disclosure as set forth in the following claims. The specification and drawings are, accordingly, to be regarded in an illustrative sense rather than a restrictive sense.

The invention claimed is:

1. A method for labeling one or more medications concurrently administered to a patient as a line of therapy, the method comprising:
deriving, via an artificial intelligence engine trained on a plurality of patient histories, a plurality of curated fields from non-curated digital records, wherein the non-curated digital records comprise a plurality of different record types or a plurality of records from different sources, and wherein deriving curated fields comprises combining related portions of the non-curated digital records and determining that other portions of the non-curated digital records are unrelated to the related portions;
identifying medical records of the patient from a plurality of digital records, the digital records including curated records and subsequently curated records, wherein the subsequently curated records comprise the derived plurality of curated fields, and wherein a subset of the medical records reflect medical history of the patient with respect to one or more treatments after a disease state diagnosis of the patient;
creating, from the subset of medical records, a plurality of treatment intervals comprising at least one medication administered to the patient and a time interval, wherein a given time interval is associable with more than one treatment interval;
associating medications of the one or more treatments with a respective treatment interval when the administration of the medication falls within the time interval;
extending the time interval of a respective treatment interval to include an earlier or later time interval of another treatment when the another treatment of the one or more treatments falls outside the time interval but within an extension period and wherein an interval superseding event does not take place during the extended time interval;
identifying, via an unsupervised artificial intelligence engine, one or more potential lines of therapy from the plurality of treatment intervals, wherein each potential line of therapy comprises one or more of the plurality of treatment intervals and a maximum likelihood estimation that the one or more of the plurality of treatment intervals of the potential line of therapy is a line of therapy; and
labeling, via the unsupervised artificial intelligence engine, the potential line of therapy having the highest maximum likelihood estimation as the line of therapy.

2. The method of claim 1, further comprising:
labeling, via the unsupervised artificial intelligence engine, additional potential lines of therapy during successive time intervals as an incrementally numbered line of therapy from the potential lines of therapy occurring chronologically after each preceding line of therapy and having the respective highest maximum likelihood estimation of the potential lines of therapy in each successive time interval.

3. The method of claim 2, further comprising:
labeling, via the unsupervised artificial intelligence engine, respective incrementally numbered lines of therapies for a plurality of patients;
identifying a plurality of cohorts of patients; and
reporting the incrementally numbered lines of therapies for each of the plurality of cohorts of patients.

4. The method of claim 3, further comprising:
reporting institution-wide and physician-specific compliance to standardized treatment guidelines.

5. The method of claim 3, further comprising:
reporting changes to lines of therapies over time based at least in part on the respective time intervals of each line of therapy.

6. The method of claim 3, further comprising:
reporting analytics on therapeutic impact differences between a first cohort of patients and a second cohort of patients, wherein a cohort identifies patients as having one or more similar dates of treatment, lines of therapy, diagnosis, outcomes, geographic locations, treating physicians, treating institutions, genomic markers, or clinical characteristics.

7. The method of claim 6, further comprising:
reporting analytics on progression-free survival between the first cohort and second cohort.

8. The method of claim 3, further comprising:
generating a progression-free survival curve for a first cohort of patients having at least one labeled line of therapy in common;
generating a progression-free survival curve for a second cohort of patients having at least one other labeled line of therapy in common; and
displaying the progression-free survival curve for the first cohort on a survival graph and the second cohort on the same survival graph.

9. The method of claim 8, wherein a labeled line of therapy includes one or more of:
medication name, treatment roll-up class, dosage, or method of administration.

10. The method of claim 1, further comprising:
generating a report, the report comprising each line of therapy labeled for the patient and the respective time interval.

11. The method of claim 1, wherein disease state diagnoses includes cancer, cardiology, depression, mental health, diabetes, infectious disease, epilepsy, dermatology, and autoimmune diseases.

12. The method of claim 1, wherein the disease state diagnosis is cancer.

13. The method of claim 1, wherein the plurality of digital records comprises one or more EHR medical records and one or more curated medical records.

14. The method of claim 13, wherein a curated medical record is an image of a record not included in the one or more EHR medical records.

15. The method of claim 13, further comprising:
optical character recognizing, and encoding the curated medical record into a structured format.

16. The method of claim 1, further comprising:
identifying, by a treatment identifier, a treatment that was administered to the patient and an administration date on which the treatment was administered.

17. The method of claim 1, wherein a treatment includes one or more of:
administration of a medication, a drug, a molecule, or a chemical,
implantation of a medical device,
use of a medical device,
use of a biotherapy, a virotherapy, a phage therapy, a phytotherapy, a gene therapy, an epigenetic therapy, a protein therapy, an enzyme replacement therapy, a hormone therapy, a cell therapy, an immunotherapy, an antibody therapy, a nutrition therapy, an electromagnetic radiation therapy, or a radiation therapy,
a surgical procedure, or
a radiosurgery.

18. A system for labeling one or more medications concurrently administered to a patient as a line of therapy, comprising:
at least one computer having at least one processor programmed to:
derive, via an artificial interface engine trained on a plurality of patient histories, a plurality of curated fields from non-curated digital records, wherein the non-curated digital records comprise a plurality of different record types or a plurality of records from different sources, and wherein deriving curated fields comprises combining related portions of the non-curated digital records and determining that other portions of the non-curated digital records are unrelated to the related portions;
identify medical records of the patient from a plurality of digital records, the digital records including curated records and subsequently curated records, wherein the subsequently curated records comprise the derived plurality of curated fields, and wherein a subset of the medical records reflect medical history of the patient with respect to one or more treatments after a disease state diagnosis of the patient;
create, from the subset of medical records, a plurality of treatment intervals comprising at least one medication administered to the patient and a time interval, wherein a given time interval is associable with more than one treatment interval;
associate medications of the one or more treatments with a respective treatment interval when the administration of the medication falls within the time interval; and
extend the time interval of a respective treatment interval to include an earlier or later time interval of another treatment when the another treatment of the one or more treatments falls outside the time interval but within an extension period and wherein an interval superseding event does not take place during the extended time interval;
the at least one computer including an unsupervised artificial intelligence engine programmed to:
identify one or more potential lines of therapy from the plurality of treatment intervals, wherein each potential line of therapy comprises one or more of the plurality of treatment intervals and a maximum likelihood estimation that the one or more of the plurality of treatment intervals of the potential line of therapy is a line of therapy; and
label the potential line of therapy having the highest maximum likelihood estimation as the line of therapy.

19. The system of claim 18, wherein the unsupervised artificial intelligence engine is programmed to label additional potential lines of therapy during successive time intervals as an incrementally numbered line of therapy from the potential lines of therapy occurring chronologically after each preceding line of therapy and having the respective highest maximum likelihood estimation of the potential lines of therapy in each successive time interval.

20. The system of claim 19, wherein the unsupervised artificial intelligence engine is programmed to:
label respective incrementally numbered lines of therapies for a plurality of patients;
identify a plurality of cohorts of patients; and
report the incrementally numbered lines of therapies for each of the plurality of cohorts of patients.

21. The system of claim 20, the at least one computer further programmed to:
report institution-wide and physician-specific compliance to standardized treatment guidelines.

22. The system of claim 20, wherein the at least one computer is programmed to:
report changes to lines of therapies over time based at least in part on the respective time intervals of each line of therapy.

23. The system of claim 20, the at least one computer further programmed to:
report analytics on therapeutic impact differences between a first cohort of patients and a second cohort of patients, wherein a cohort identifies patients as having one or more similar dates of treatment, lines of therapy, diagnosis, outcomes, geographic locations, treating physicians, treating institutions, genomic markers, or clinical characteristics.

24. The system of claim 23, the at least one computer further programmed to:
report analytics on progression-free survival between the first cohort and second cohort.

25. The system of claim 20, the at least one computer further programmed to:
generate a progression-free survival curve for a first cohort of patients having at least one labeled line of therapy in common;
generate a progression-free survival curve for a second cohort of patients having at least one other labeled line of therapy in common; and
display the progression-free survival curve for the first cohort on a survival graph and the second cohort on the same survival graph.

26. The system of claim 25, wherein a labeled line of therapy includes one or more of:
medication name, treatment roll-up class, dosage, or method of administration.

27. The system of claim 18, wherein disease state diagnoses includes cancer, cardiology, depression, mental health, diabetes, infectious disease, epilepsy, dermatology, and autoimmune diseases.

28. The system of claim 18, wherein the plurality of digital records comprises one or more EHR medical records and one or more curated medical records.

29. The system of claim 28, the at least one computer further programmed to:
optical character recognize, and encode the curated medical record into a structured format.

30. The system of claim 18, wherein a treatment includes one or more of:
- administration of a medication, a drug, a molecule, or a chemical,
- implantation of a medical device,
- use of a medical device,
- use of a biotherapy, a virotherapy, a phage therapy, a phytotherapy, a gene therapy, an epigenetic therapy, a protein therapy, an enzyme replacement therapy, a hormone therapy, a cell therapy, an immunotherapy, an antibody therapy, a nutrition therapy, an electromagnetic radiation therapy, or a radiation therapy,
- a surgical procedure, or
- a radiosurgery.

* * * * *